United States Patent
Man et al.

(10) Patent No.: US 10,604,510 B2
(45) Date of Patent: Mar. 31, 2020

(54) SOLID FORMS COMPRISING (1E, 4E)-2-AMINO-N,N-DIPROPYL-8-(4-(PYRROLIDINE-1-CARBONYL)PHENYL)-3H-BENZO[B]AZEPINE-4-CARBOXAMI COMPOSITIONS THEREOF, AND USES THEREOF

(71) Applicant: Celgene Corporation, Summit, NJ (US)

(72) Inventors: Hon-Wah Man, Princeton, NJ (US); Timothy D. Fitzpatrick, Kirkland, WA (US); Anthony Frank, Easton, PA (US); Ying Li, Millburn, NJ (US); Xiaoling Lu, Whippany, NJ (US); Marie G. Beauchamps, Randolph, NJ (US); Antonio C. Ferretti, Summit, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/570,191

(22) Filed: Sep. 13, 2019

(65) Prior Publication Data
US 2020/0002316 A1 Jan. 2, 2020

Related U.S. Application Data

(63) Continuation of application No. 15/537,331, filed as application No. PCT/US2015/065755 on Dec. 15, 2015.

(60) Provisional application No. 62/092,764, filed on Dec. 16, 2014.

(51) Int. Cl.
C07D 223/16 (2006.01)
C07D 403/10 (2006.01)
A61P 35/00 (2006.01)

(52) U.S. Cl.
CPC ............ *C07D 403/10* (2013.01); *A61P 35/00* (2018.01); *C07B 2200/13* (2013.01)

(58) Field of Classification Search
CPC .................................................. C07D 223/16
See application file for complete search history.

(56) References Cited

U.S. PATENT DOCUMENTS

| | | | |
|---|---|---|---|
| 8,304,407 B2 | 11/2012 | Doherty et al. | |
| 8,314,090 B2 | 11/2012 | Howbert et al. | |
| 9,216,192 B2 | 12/2015 | Howbert et al. | |
| 2005/0191614 A1 | 9/2005 | Cima et al. | |
| 2012/0082658 A1 | 4/2012 | Hershberg | |
| 2019/0100512 A1 | 4/2019 | Man | |

FOREIGN PATENT DOCUMENTS

WO  WO 2010/054215 A1  5/2010

OTHER PUBLICATIONS

Balbach S et al: "Pharmaceutical evaluation of early development candidates: 'The 100 mg approach'", International Journal of Pharmaceutics, 2004, vol. 275, pp. 1-12.
Barrett et al., "A novel TLR-8 agonist attenuates nasal symptoms/congestion in both dog and human allergen challenge studies", Journal of Inflammation, 2013.
Byrn et al. "Pharmaceutical Solids: A Strategic Approach to Regulatory Considerations", Pharmaceutical Research, 1995, vol. 12, No. 7, p. 945-954.
Singhal D et al: "Drug Polymorphism and Dosage Form Design: A practical perspective", Advanced Drug Delivery Reviews, 2004, vol. 56, p. 335-347.
Kawaguchi Y. et al. "Drug and crystal polymorphism", Journal of Human Environmental Engineering, 2002, vol. 4, p. 310-317. (in Japanese).
Yamano, M. "Approach to Crystal Polymorph in Process Research of New Drug", Journal of Synthetic Organic Chemistry, 2007, vol. 65, No. 9, p. 907-913. (in Japanese).
Notification No. 568 of Pharmaceutical Evaluation Division, Pharmaceutical and Food Safety Bureau, Ministry of Health, Labor and Welfare, 2001, 45 pages. (in Japanese).
"Crystalization of Polymorphs and Pseudo-polymorphs and Its Control", Pharm Stage, 2007, vol. 6, No. 10, p. 48-53. (in Japanese).
"API form screening and selection in drug discovery stage", Pharm Stage, 2007, vol. 6, No. 10, p. 20-25 (in Japanese).
Japanese Office Action issued for Japanese Patent Application No. 2017-532617, dated Jun. 13, 2019.
"Polymorphism in Pharmaceutical Solids", Drugs and the Pharmaceutical Sciences, A Series of Textbooks and Monographs, Brittain, H.G. ed., Chapter 1, vol. 192, 654 pages.

*Primary Examiner* — Bruck Kifle
(74) *Attorney, Agent, or Firm* — Cooley LLP; Heidi A. Erlacher; Chun L. Yu

(57) ABSTRACT

Provided herein are compositions including the crystalline forms of (1E, 4E)-2-amino-N,N-dipropyl-8-(4-(pyrrolidine-1-carbonyl)phenyl)-3H-benzo[b]azepine-4-carboxamide ("Compound A"), methods of making the crystalline forms, and methods of using the crystalline forms for the treatment of diseases, including, for example, cancer.

13 Claims, 50 Drawing Sheets

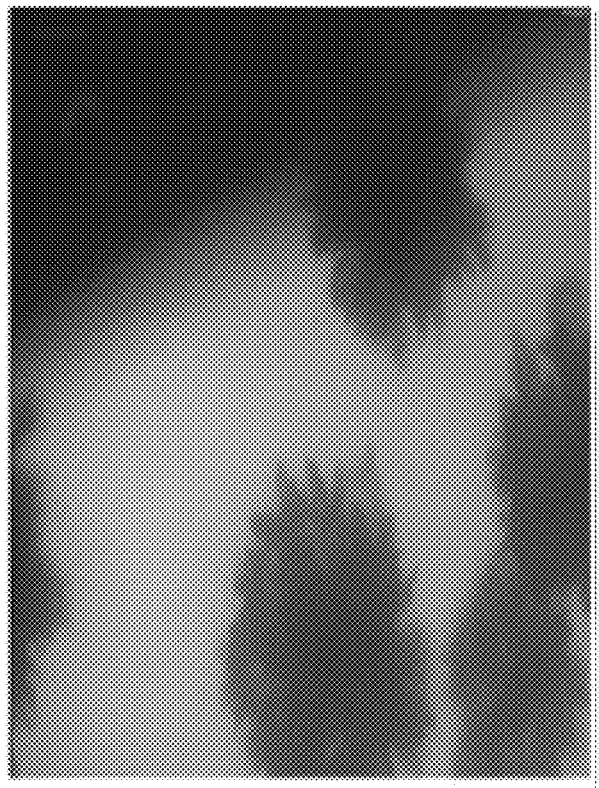 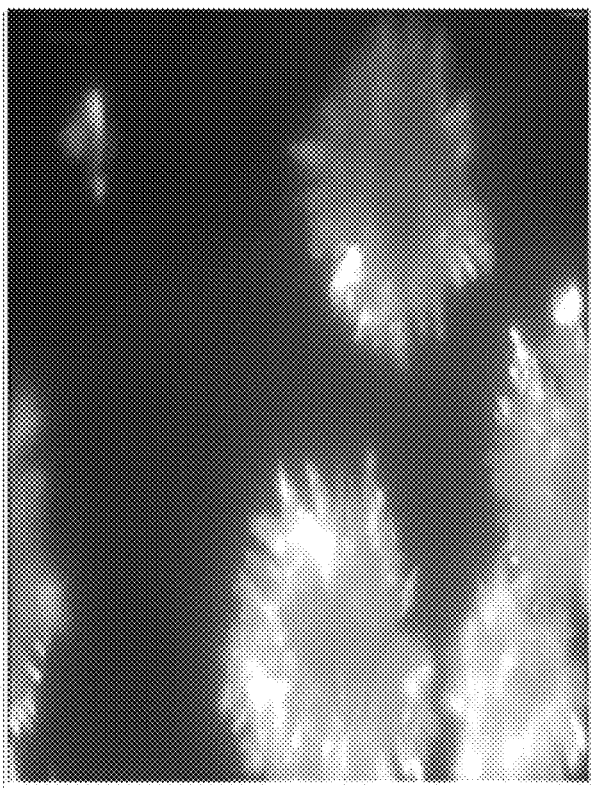
FIG. 17A
FIG. 17B

SOLID FORMS COMPRISING (1E, 4E)-2-AMINO-N,N-DIPROPYL-8-(4-(PYRROLIDINE-1-CARBONYL)PHENYL)-3H-BENZO[B]AZEPINE-4-CARBOXAMI COMPOSITIONS THEREOF, AND USES THEREOF

This application is a continuation of U.S. application Ser. No. 15/537,331, filed Jun. 16, 2017, which is a national stage application, filed under 35 U.S.C. § 371, of International Application No. PCT/US2015/065755, filed Dec. 15, 2015, which claims priority to and the benefit of U.S. Provisional Patent Application No. 62/092,764, filed Dec. 16, 2014, the contents of each of which are hereby incorporated by reference in their entireties and for all purposes.

FIELD

Provided herein are compositions of the crystalline forms of (1E, 4E)-2-amino-N,N-dipropyl-8-(4-(pyrrolidine-1-carbonyl)phenyl)-3H-benzo[b]azepine-4-carboxamide ("Compound A"), methods of making the crystalline forms, and methods of using the crystalline forms for the treatment of diseases, including, for example, cancer.

BACKGROUND

There is an enormous variety of cancers which are described in detail in the medical literature. Examples include cancers of the lung, colon, liver, kidneys, bladder, ovaries, prostate, breast, head and neck, brain, blood and intestine. The incidence of cancer continues to climb as the general population ages, as new cancers develop, and as susceptible populations (e.g., people infected with AIDS or excessively exposed to sunlight) grow. To that end, there is a need in the art for additional molecular targets for effective anti-cancer therapies.

Despite availability of a variety of anti-cancer and chemotherapeutic agents, many of these therapies have drawbacks. Stockdale, Medicine, vol. 3, Rubenstein and Federman, eds., ch. 12, sect. 10, 1998. For example, many chemotherapeutic agents are toxic, and chemotherapy causes significant, and often acute dangerous side effects including severe nausea, bone marrow depression, and immunosuppression. In fact, even with administration of combinations of chemotherapeutic agents, many tumor cells are resistant or develop resistance to such chemotherapeutic agents. Further, it is well recognized that specific polymorphic crystalline forms of therapeutic agents, including anti-cancer agents are effective while other forms of the same compound may have reduced or little-to-no activity. Thus, identification of polymorphic forms offers improved activity of anti-cancer and chemotherapeutic agents.

The available options for the treatment of cancer are limited. Toll-like receptors (TLRs) are a class of critical transmembrane proteins with known involvement in the regulation of the innate immune system. TLRs are also implicated in the onset and progression of many cancers. TLRs modulate specific signaling molecules, including NFκB, and represent a potential target for anti-cancer agents in the treatment of cancer. A tremendous demand therefore exists for new methods and compositions that can be used to treat patients with cancer. Described herein are solutions to these and other problems in the art.

BRIEF SUMMARY

Provided herein are crystalline forms of the compound having formula (I).

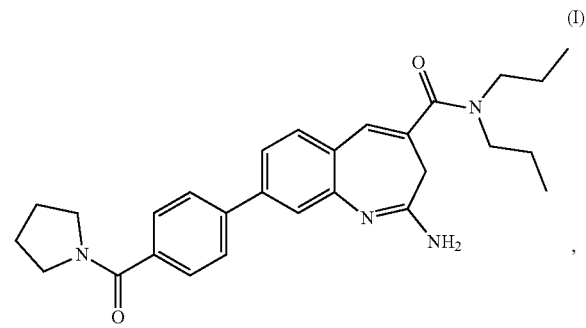 [SMILES: CCCN(CCC)C(=O)C1=Cc2ccc(-c3ccc(C(=O)N4CCCC4)cc3)cc2N=C(N)C1]

(I)

((1E, 4E)-2-amino-N,N-dipropyl-8-(4-(pyrrolidine-1-carbonyl)phenyl)-3H-benzo[b]azepine-4-carboxamide ("Compound A")). The crystalline form can be an unsolvated or solvated crystalline form of the compound of formula (I).

Also provided herein are compositions including the crystalline forms of the compound of formula (I) described herein, methods of making the crystalline forms, and methods of using the crystalline forms for the treatment of diseases, including, for example, cancer.

Further provided herein are methods of agonizing a Toll-like receptor using the crystalline forms of the compound of formula (I) described herein. In one aspect the method includes agonizing a Toll-like receptor (TLR8) by contacting TLR8 with an effective amount of a crystalline form of the compound formula (I) described herein, wherein the effective amount agonizes the TLR8.

Also provided herein are methods of treating cancer using crystalline forms of the compound of formula (I) described herein. In one aspect, the method includes treating cancer by administering a therapeutically effective amount of a crystalline form of the compound formula (I) described herein to a subject in need thereof, thereby treating the cancer. Further, the crystalline forms of the compound of formula (I) and pharmaceutical compositions comprising the same can be used for methods of treating cancer.

BRIEF DESCRIPTION OF THE DRAWINGS

FIG. 17A illustrates the microscopy picture of form D (Table 2 experiment B1_1) showing hedgehog-like crystal agglomerates using crossed polarization filters. FIG. 17B illustrates the microscopy picture of form D (Table 2 experiment B1_1) showing hedgehog-like crystal agglomerates without using polarization. The bar indicates approximately 250 µm.

DETAILED DESCRIPTION

Figure 1:
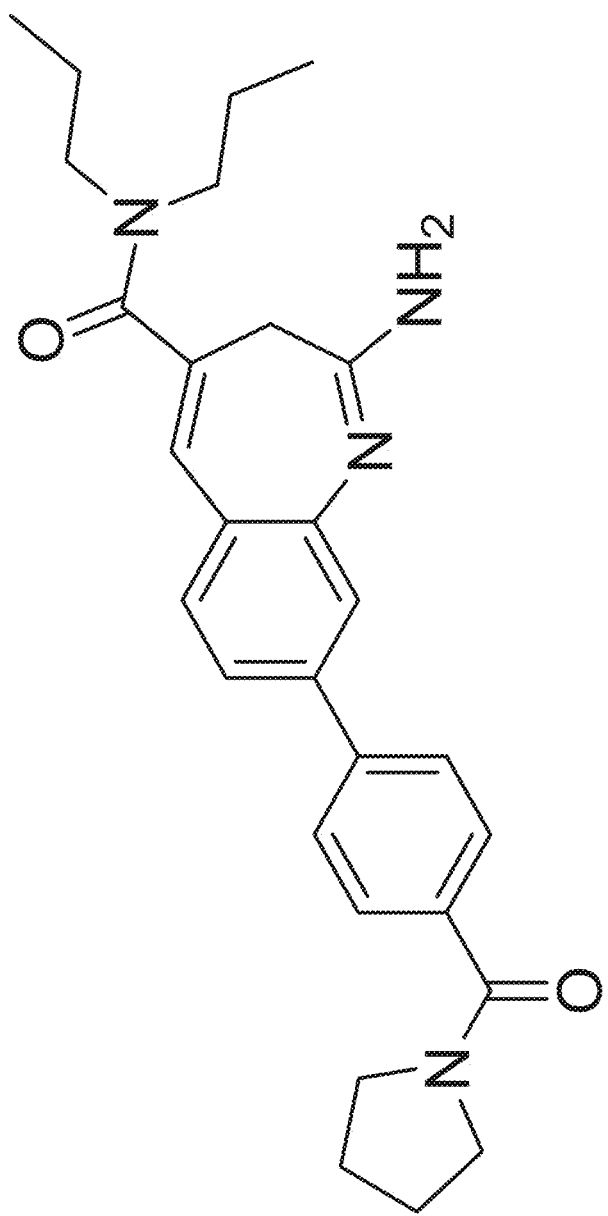
FIG. 1. Illustrates the structure of Compound A
Figure 2:
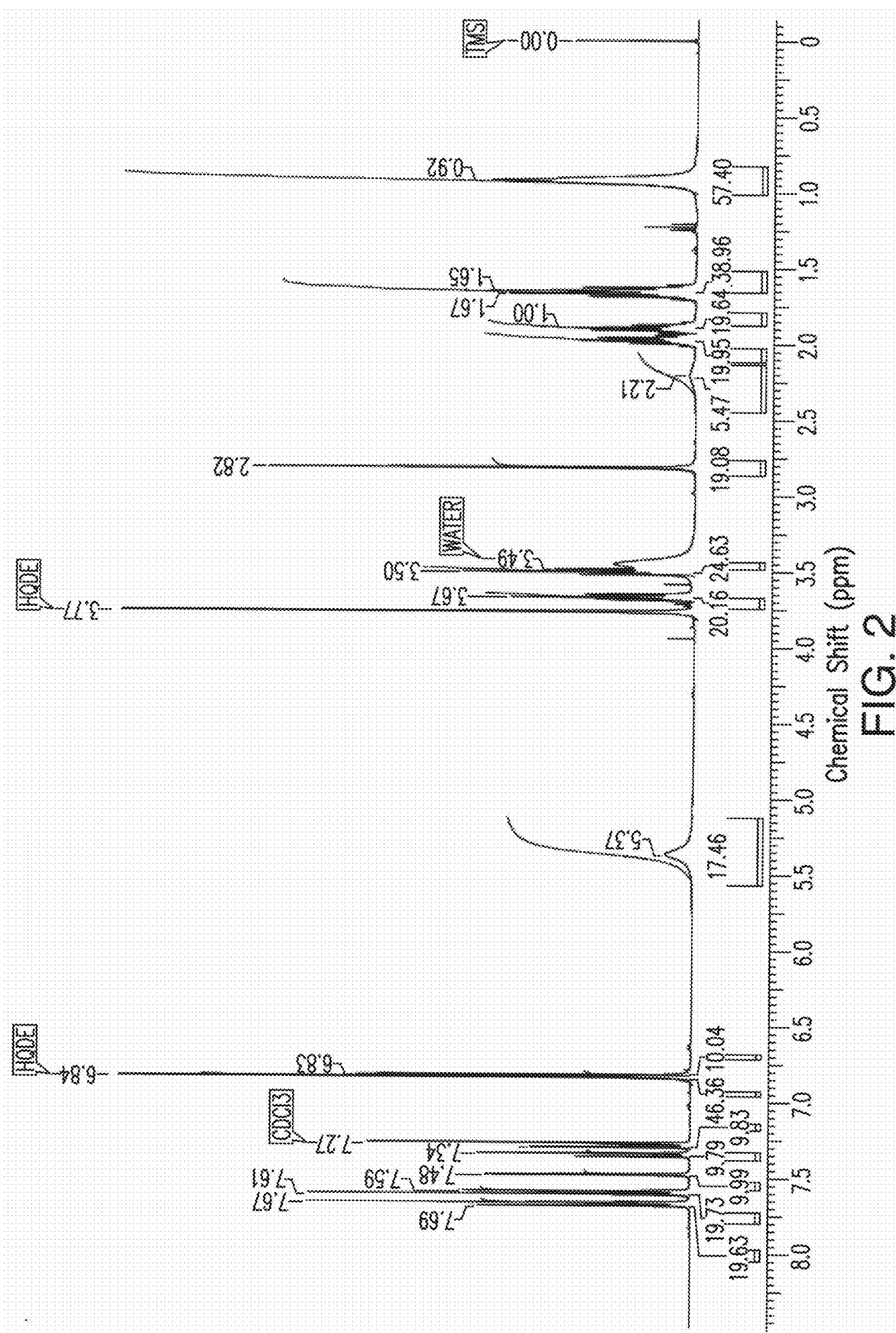
FIG. 2. Illustrates the $^1$H NMR spectrum of assay determination of starting material. The internal standard is hydrochinone dimethylether (HQDE).

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The terms "(1E, 4E)-2-amino-N,N-dipropyl-8-(4-(pyrrolidine-1-carbonyl)phenyl)-3H-benzo[b]azepine-4-carboxamide" and "Compound A" refer to a compound having the structure:

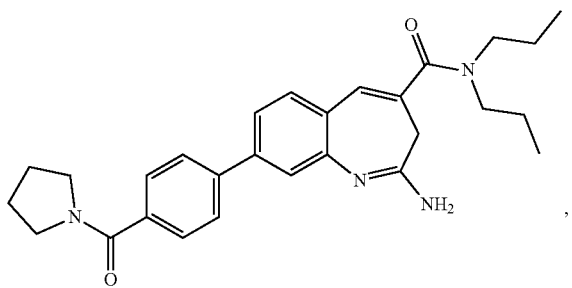 [SMILES: CCCN(CCC)C(=O)C1=Cc2ccc(-c3ccc(C(=O)N4CCCC4)cc3)cc2N=C(N)C1]

as disclosed in U.S. Patent Application No. 2012/0082658, the entirety of which is incorporated herein by reference.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when including one polymorph than when including another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, some solid-state transitions may result in lack of potency or, at the other extreme, toxicity. In addition, the physical properties may be important in processing (e.g. one polymorph might be more likely to form solvates or might be difficult to filter and wash free of impurities, and particle shape and size distribution might be different between polymorphs).

As used herein and unless otherwise specified, the terms "solvate" and "solvated," refer to a crystal form of a substance formed from the association of one or more solvent molecules to a compound provided herein. The term "solvate" includes "hydrates" (e.g., a mono-hydrate, dihydrate, trihydrate, tetrahydrate and the like, compound described herein where the solvent includes water). A hydrate includes a compound provided herein or a salt thereof that further includes a stoichiometric or non-stoichiometric amount of water bound by non-covalent intermolecular forces. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the terms "amorphous," and "amorphous form," and related terms used herein, refer that the substance, component or product in question is not substantially crystalline as determined by X-ray diffraction. The term "amorphous form" describes a disordered solid form, i.e., a solid form lacking long range crystalline order. In embodiments, an amorphous form of a substance may be substantially free of other amorphous forms and/or crystal forms. In embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In embodiments, an amorphous form of a substance may be physically and/or chemically pure. In embodiments, an amorphous form of a substance is about 99%, 98%, 97%, 96%, 95%, 94%, 93%, 92%, 91% or 90% physically and/or chemically pure.

Techniques for characterizing crystal forms and amorphous forms include those known and described in the art, such as, but not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample including more than one solid phase. Other methods useful for analyzing powder diffraction data include unit cell indexing, which allows one of skill in the art to determine unit cell parameters from a sample including crystalline powder.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable acid addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

A "pharmaceutically acceptable excipient," comprises a substance that aids the administration of an active agent to a subject or modifies the absorption by a subject upon administration. A pharmaceutically acceptable excipient typically has no significant adverse toxicological effect on the patient. Examples of pharmaceutically acceptable excipients include, but are not limited to, water, NaCl (including salt solutions), normal saline solutions, sucrose, glucose, binders, fillers, disintegrants, lubricants, coatings, sweeteners, flavors, alcohols, oils, gelatins, carbohydrates such as lactose, amylose or starch, fatty acid esters, hydroxymethylcellulose, polyvinyl pyrrolidine, and colors, and the like. One of skill in the art will recognize that other pharmaceutical excipients known in the art are useful in the present invention.

As used herein, "administer" or "administration" refers to the act of physically delivering a substance as it exists outside the body into a patient. Administration includes all forms known in the art for delivering therapeutic agents, including but not limited to oral, topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal). When a disease, disorder or condition, or a symptom thereof, is treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

As used herein the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

The terms "patient," "subject," "patient in need thereof," and "subject in need thereof" are herein used interchangeably and refer to a living organism suffering from or prone to a disease or condition that can be treated by administration of a composition described herein. Non-limiting examples of organisms include humans, other mammals, bovines, rats, mice, dogs, monkeys, goat, sheep, cows, deer, and other non-mammalian animals. In specific embodiments, a patient is human.

The term "cancer" is used in accordance with its plain ordinary meaning and refers to all types of neoplasms and malignant or benign tumors found in mammals. "Cancer" as used herein refers to leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas. In preferred embodiments, the cancer is colon carcinoma, ovarian cancer, breast cancer, head and neck cancer, renal cancer, bladder cancer, hepatocellular cancer, or lymphoma.

"Anti-cancer agent" is used in accordance with its plain and ordinary meaning and refers to a composition (e.g., a chemotherapeutic agent) that inhibits the growth or proliferation of cells. An anti-cancer agent may be an agent approved by the FDA or similar regulatory agency of a country other than the USA, for treating cancer.

An "effective amount" is an amount sufficient to accomplish a stated purpose (e.g., achieve the effect for which it is administered, treat, manage, or prevent a disease, reduce enzyme activity, increase enzyme activity, or reduce one or more symptoms of a disease or condition). The term "therapeutically effective amount" of a compound refers to the amount of the compound that, when administered, is sufficient to treat, manage or prevent one or more of the symptoms of a disease, disorder, or condition being treated. The term also refers to the amount of the compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician. The term encompasses an amount of the compound that improves overall therapy, reduces, or avoids symptoms or causes of a disease, disorder, or condition, or enhances the therapeutic efficacy of another therapeutic agent.

Crystalline Forms:

Provided herein are crystalline forms of a compound having the formula

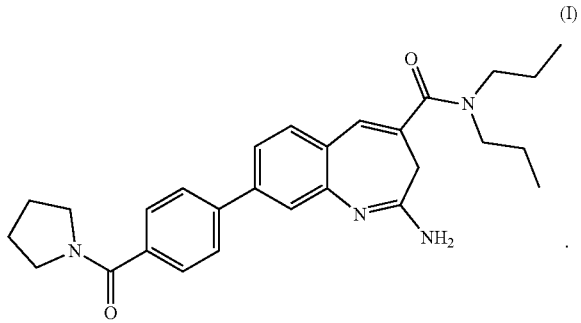 [SMILES: CCCN(CCC)C(=O)C1=Cc2ccc(-c3ccc(C(=O)N4CCCC4)cc3)cc2N=C(N)C1]

(I)

The crystalline form can be an unsolvated crystalline form (e.g., a crystal form substantially without solvent) or a solvated crystalline form. The crystalline form of the compound of formula (I) can be obtained using techniques known in the art, including but not limited to, evaporative screening, cooling and precipitation screening, or slurry screening. Crystals of the crystalline forms of the compound of formula (I) can be obtained from solvents and techniques set forth in, for example, Table 1, Table 2, or Table 3. The crystalline form can be an unsolvated crystalline form. The crystalline form can be a solvated form. The crystalline form can include a form described herein within the Examples set forth below (e.g., Form A, Form B, Form C, Form D, Form E, Form F, Form G, Form H, Form I, or Form J). Thus, in embodiments, the crystalline form described herein can be referred to by its present solvation state (i.e., solvated or unsolvated), by its alphanumeric Form name, or a combination thereof. The crystalline form, can, in embodiments, be an unsolvated crystalline form corresponding to Form A, Form C, Form G, or Form H. The crystalline form, can, in embodiments, be a solvated crystalline form corresponding to Form B, Form D, Form E, Form F, or Form I.

The crystalline form of the compound of formula (I) can be characterized by X-ray powder diffraction (XRPD). The crystalline form of the compound of formula (I) can be characterized by a XRPD pattern that includes angle 2θ peaks (i.e., degrees 2θ) at about 11.9±0.3, 16.4±0.3, 18.5±0.3, 20.9±0.3, 21.2±0.3, 21.6±0.3, 23.0±0.3, 23.5±0.3, 24.2±0.3, and 27.4±0.3. All values for angle 2θ peaks set forth herein (e.g., angle 2θ values for Form A, Form B, Form C, Form D, Form E, Form F, Form G, Form H, Form I, or Form J) are obtained by using a Cu Kα radiation source (1.54 Å). Further, the angle 2θ values described herein should be understood to include variances associated with X-ray diffraction spectroscopy. The XRPD pattern of the crystalline form of the compound of formula (I) can further include angle 2θ peaks at about 8.7±0.3, 9.2±0.3, 10.8±0.3, 14.8±0.3, 15.5±0.3, 17.7±0.3, 19.9±0.3, 20.4±0.3, 22.0±0.3, 22.4±0.3, 25.9±0.3, 26.3±0.3, 26.8±0.3, 27.0±0.3, 28.0±0.3, 28.9±0.3, and 29.8±0.3.

In some embodiments, the crystalline form of the compound of formula (I) is characterized by a XRPD pattern that includes angle 2θ peaks at about 8.7±0.3, 9.2±0.3, 10.8±0.3, 11.9±0.3, 14.8±0.3, 15.5±0.3, 16.4±0.3, 17.7±0.3, 18.5±0.3, 19.9±0.3, 20.4±0.3, 20.9±0.3, 21.2±0.3, 21.6±0.3, 22.0±0.3, 22.4±0.3, 23.0±0.3, 23.5±0.3, 24.2±0.3, 25.9±0.3, 26.3±0.3, 26.8±0.3, 27.0±0.3, 27.4±0.3, 28.0±0.3, 28.9±0.3, and 29.8±0.3.

In some embodiments, the crystalline form of the compound of formula (I) is characterized by a XRPD pattern that includes angle 2θ peaks (i.e., degrees 2θ) at about 11.9±0.2, 16.4±0.2, 18.5±0.2, 20.9±0.2, 21.2±0.2, 21.6±0.2, 23.0±0.2, 23.5±0.2, 24.2±0.2, and 27.4±0.2. The XRPD pattern of the crystalline form of the compound of formula (I) can further include angle 2θ peaks at about 8.7±0.2, 9.2±0.2, 10.8±0.2, 14.8±0.2, 15.5±0.2, 17.7±0.2, 19.9±0.2, 20.4±0.2, 22.0±0.2, 22.4±0.2, 25.9±0.2, 26.3±0.2, 26.8±0.2, 27.0±0.2, 28.0±0.2, 28.9±0.2, and 29.8±0.2.

In some embodiments, the crystalline form of the compound of formula (I) is characterized by a XRPD pattern that includes angle 2θ peaks at about 8.7±0.2, 9.2±0.2, 10.8±0.2, 11.9±0.2, 14.8±0.2, 15.5±0.2, 16.4±0.2, 17.7±0.2, 18.5±0.2, 19.9±0.2, 20.4±0.2, 20.9±0.2, 21.2±0.2, 21.6±0.2, 22.0±0.2, 22.4±0.2, 23.0±0.2, 23.5±0.2, 24.2±0.2, 25.9±0.2, 26.3±0.2, 26.8±0.2, 27.0±0.2, 27.4±0.2, 28.0±0.2, 28.9±0.2, and 29.8±0.2.

In some embodiments, the crystalline form of the compound of formula (I) is characterized by a XRPD pattern that includes angle 2θ peaks (i.e., degrees 2θ) at about 11.9±0.1, 16.4±0.1, 18.5±0.1, 20.9±0.1, 21.2±0.1, 21.6±0.1, 23.0±0.1, 23.5±0.1, 24.2±0.1, and 27.4±0.1. The XRPD pattern of the crystalline form of the compound of formula (I) can further include angle 2θ peaks at about 8.7±0.1, 9.2±0.1, 10.8±0.1, 14.8±0.1, 15.5±0.1, 17.7±0.1, 19.9±0.1, 20.4±0.1, 22.0±0.1, 22.4±0.1, 25.9±0.1, 26.3±0.1, 26.8±0.1, 27.0±0.1, 28.0±0.1, 28.9±0.1, and 29.8±0.1.

In some embodiments, the crystalline form of the compound of formula (I) is characterized by a XRPD pattern that includes angle 2θ peaks at about 8.7±0.1, 9.2±0.1, 10.8±0.1, 11.9±0.1, 14.8±0.1, 15.5±0.1, 16.4±0.1, 17.7±0.1, 18.5±0.1, 19.9±0.1, 20.4±0.1, 20.9±0.1, 21.2±0.1, 21.6±0.1, 22.0±0.1, 22.4±0.1, 23.0±0.1, 23.5±0.1, 24.2±0.1, 25.9±0.1, 26.3±0.1, 26.8±0.1, 27.0±0.1, 27.4±0.1, 28.0±0.1, 28.9±0.1, and 29.8±0.1.

In some embodiments, the crystalline form of the compound of formula (I) is characterized by a XRPD pattern that includes angle 2θ peaks (i.e., degrees 2θ) at about 11.9, 16.4, 18.5, 20.9, 21.2, 21.6, 23.0, 23.5, 24.2, and 27.4. The XRPD pattern of the crystalline form of the compound of formula (I) can further include angle 2θ peaks at about 8.7, 9.2, 10.8, 14.8, 15.5, 17.7, 19.9, 20.4, 22.0, 22.4, 25.9, 26.3, 26.8, 27.0, 28.0, 28.9, and 29.8.

In some embodiments, the crystalline form of the compound of formula (I) is characterized by a XRPD pattern that includes angle 2θ peaks at about 8.7, 9.2, 10.8, 11.9, 14.8, 15.5, 16.4, 17.7, 18.5, 19.9, 20.4, 20.9, 21.2, 21.6, 22.0, 22.4, 23.0, 23.5, 24.2, 25.9, 26.3, 26.8, 27.0, 27.4, 28.0, 28.9, and 29.8.

Figure 42:
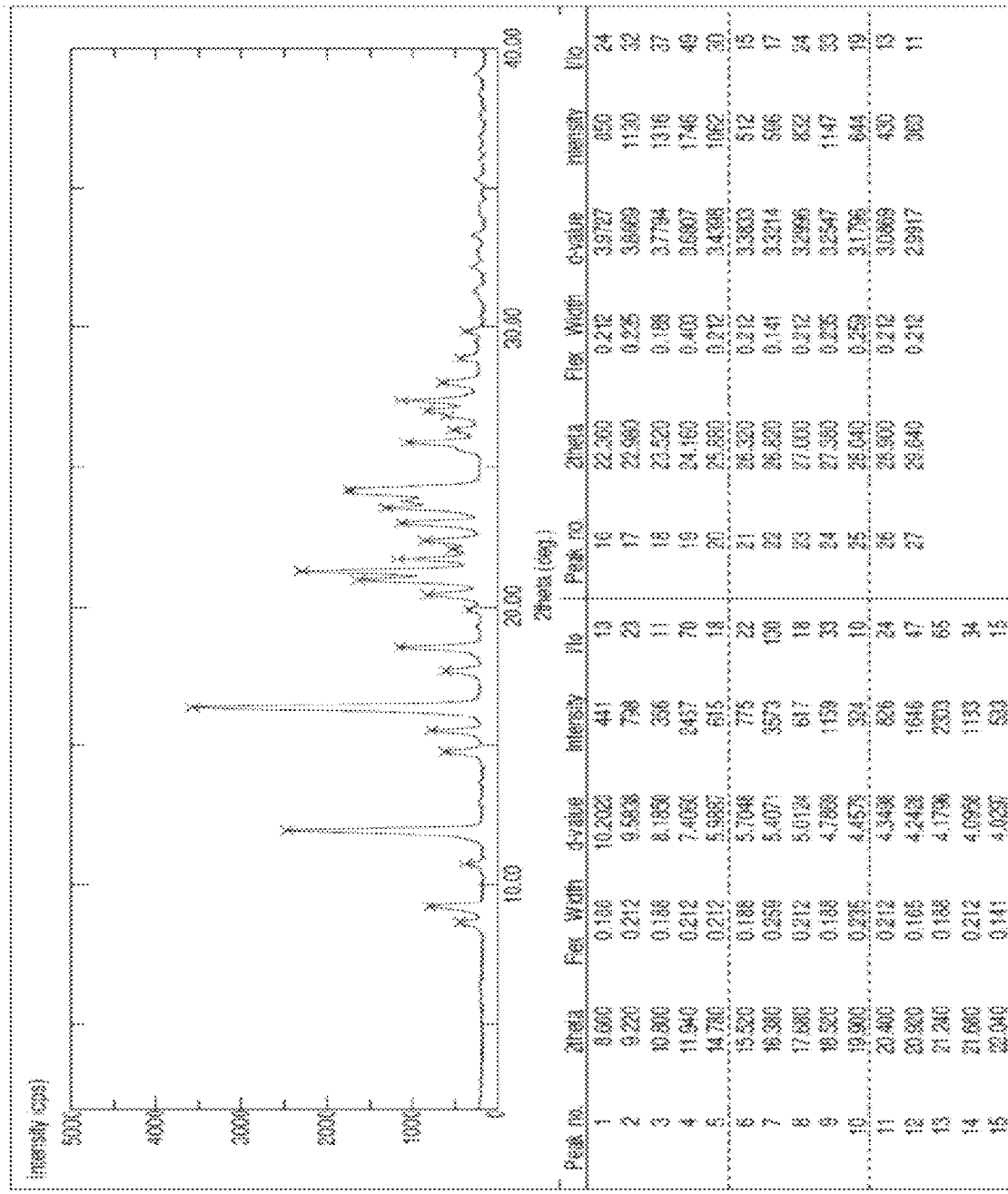
FIG. 42. Illustrates the XRPD of form A.

In certain embodiments, the crystalline form of the compound of formula (I) is characterized by a XRPD pattern corresponding substantially to FIG. 42.

In some embodiments, the crystalline form of the compound of formula (I) is characterized by a XRPD pattern that includes d spacings at about 7.40±0.3, 5.40±0.3, 4.78±0.3, 4.24±0.3, 4.17±0.3, 4.09±0.3, 3.86±0.3, 3.77±0.3, 3.68±0.3, 3.25±0.3. The d spacing values described herein should be understood to include variances associated with X-ray diffraction spectroscopy. All values for d spacings set forth herein (e.g., d spacings for Form A, Form B, Form C, Form D, Form E, Form F, Form G, Form H, Form I, or Form J) are obtained by using a Cu Kα radiation source (1.54 Å). The XRPD pattern of the crystalline form of the compound of formula (I) can further include d spacings at about 10.20±0.3, 9.58±0.3, 8.18±0.3, 5.98±0.3, 5.70±0.3, 5.01±0.3, 4.45±0.3, 4.34±0.3, 4.02±0.3, 3.97±0.3, 3.43±0.3, 3.38±0.3, 3.32±0.3, 3.29±0.3, 3.17±0.3, 3.08±0.3, and 2.99±0.3.

In some embodiments, the crystalline form of the compound of formula (I) is characterized by a XRPD pattern that includes d spacings at about 10.20±0.3, 7.40±0.3, 9.58±0.3, 8.18±0.3, 5.98±0.3, 5.70±0.3, 5.40±0.3, 5.01±0.3, 4.78±0.3, 4.45±0.3, 4.34±0.3, 4.24±0.3, 4.17±0.3, 4.09±0.3, 4.02±0.3, 3.97±0.3, 3.86±0.3, 3.77±0.3, 3.68±0.3, 3.43±0.3, 3.38±0.3, 3.32±0.3, 3.29±0.3, 3.25±0.3, 3.17±0.3, 3.08±0.3, and 2.99±0.3.

In some embodiments, the crystalline form of the compound of formula (I) is characterized by a XRPD pattern that includes d spacings at about 7.40±0.2, 5.40±0.2, 4.78±0.2, 4.24±0.2, 4.17±0.2, 4.09±0.2, 3.86±0.2, 3.77±0.2, 3.68±0.2, 3.25±0.2. The XRPD pattern of the crystalline form of the compound of formula (I) can further include d spacings at about 10.20±0.2, 9.58±0.2, 8.18±0.2, 5.98±0.2, 5.70±0.2, 5.01±0.2, 4.45±0.2, 4.34±0.2, 4.02±0.2, 3.97±0.2, 3.43±0.2, 3.38±0.2, 3.32±0.2, 3.29±0.2, 3.17±0.2, 3.08±0.2, and 2.99±0.2.

In some embodiments, the crystalline form of the compound of formula (I) is characterized by a XRPD pattern that includes d spacings at about 10.20±0.2, 7.40±0.2, 9.58±0.2, 8.18±0.2, 5.98±0.2, 5.70±0.2, 5.40±0.2, 5.01±0.2, 4.78±0.2, 4.45±0.2, 4.34±0.2, 4.24±0.2, 4.17±0.2, 4.09±0.2, 4.02±0.2, 3.97±0.2, 3.86±0.2, 3.77±0.2, 3.68±0.2, 3.43±0.2, 3.38±0.2, 3.32±0.2, 3.29±0.2, 3.25±0.2, 3.17±0.2, 3.08±0.2, and 2.99±0.2.

In some embodiments, the crystalline form of the compound of formula (I) is characterized by a XRPD pattern that includes d spacings at about 7.40±0.1, 5.40±0.1, 4.78±0.1, 4.24±0.1, 4.17±0.1, 4.09±0.1, 3.86±0.1, 3.77±0.1, 3.68±0.1, 3.25±0.1. The XRPD pattern of the crystalline form of the compound of formula (I) can further included spacings at about 10.20±0.1, 9.58±0.1, 8.18±0.1, 5.98±0.1, 5.70±0.1, 5.01±0.1, 4.45±0.1, 4.34±0.1, 4.02±0.1, 3.97±0.1, 3.43±0.1, 3.38±0.1, 3.32±0.1, 3.29±0.1, 3.17±0.1, 3.08±0.1, and 2.99±0.1.

In some embodiments, the crystalline form of the compound of formula (I) is characterized by a XRPD pattern that includes d spacings at about 10.20±0.1, 7.40±0.1, 9.58±0.1, 8.18±0.1, 5.98±0.1, 5.70±0.1, 5.40±0.1, 5.01±0.1, 4.78±0.1, 4.45±0.1, 4.34±0.1, 4.24±0.1, 4.17±0.1, 4.09±0.1, 4.02±0.1, 3.97±0.1, 3.86±0.1, 3.77±0.1, 3.68±0.1, 3.43±0.1, 3.38±0.1, 3.32±0.1, 3.29±0.1, 3.25±0.1, 3.17±0.1, 3.08±0.1, and 2.99±0.1.

In some embodiments, the crystalline form of the compound of formula (I) is characterized by a XRPD pattern that includes d spacings at about 7.40, 5.40, 4.78, 4.24, 4.17, 4.09, 3.86, 3.77, 3.68, 3.25. The XRPD pattern of the crystalline form of the compound of formula (I) can further included spacings at about 10.20, 9.58, 8.18, 5.98, 5.70, 5.01, 4.45, 4.34, 4.02, 3.97, 3.43, 3.38, 3.32, 3.29, 3.17, 3.08, and 2.99.

In some embodiments, the crystalline form of the compound of formula (I) is characterized by a XRPD pattern that includes d spacings at about 10.20, 7.40, 9.58, 8.18, 5.98, 5.70, 5.40, 5.01, 4.78, 4.45, 4.34, 4.24, 4.17, 4.09, 4.02, 3.97, 3.86, 3.77, 3.68, 3.43, 3.38, 3.32, 3.29, 3.25, 3.17, 3.08, and 2.99.

The crystalline form of the compound of formula (I) can be Form A, where Form A is characterized by the XRPD pattern described above or by a XRPD pattern corresponding substantially to FIG. 42.

Melting points set forth herein are determined using DSC and reported as the peak. Crystalline forms described herein of the compound of formula (I) can be can have a melting point of about 200° C. to about 215° C. Crystalline forms described herein of the compound of formula (I) can be can have a melting point of about 200° C. to about 210° C. Crystalline forms described herein of the compound of formula (I) can be can have a melting point of about 200° C. to about 205° C. Crystalline forms described herein of the compound of formula (I) can be can have a melting point of about 200° C. to about 204° C. Crystalline forms described herein of the compound of formula (I) can be can have a melting point of about 200° C. to about 203° C. Crystalline forms described herein of the compound of formula (I) can be can have a melting point of about 200° C. to about 202° C. Crystalline forms described herein of the compound of formula (I) can be can have a melting point of about 202° C. to about 215° C. Crystalline forms described herein of the compound of formula (I) can be can have a melting point of about 202° C. to about 210° C. Crystalline forms described herein of the compound of formula (I) can be can have a melting point of about 202° C. to about 205° C. Crystalline forms described herein of the compound of formula (I) can be can have a melting point of about 205° C. to about 215° C. Crystalline forms described herein of the compound of formula (I) can be can have a melting point of about 205° C. to about 210° C. The Crystalline forms described herein of the compound of formula (I) can be can have a melting point of about 208° C. to about 212° C.

Figure 7:
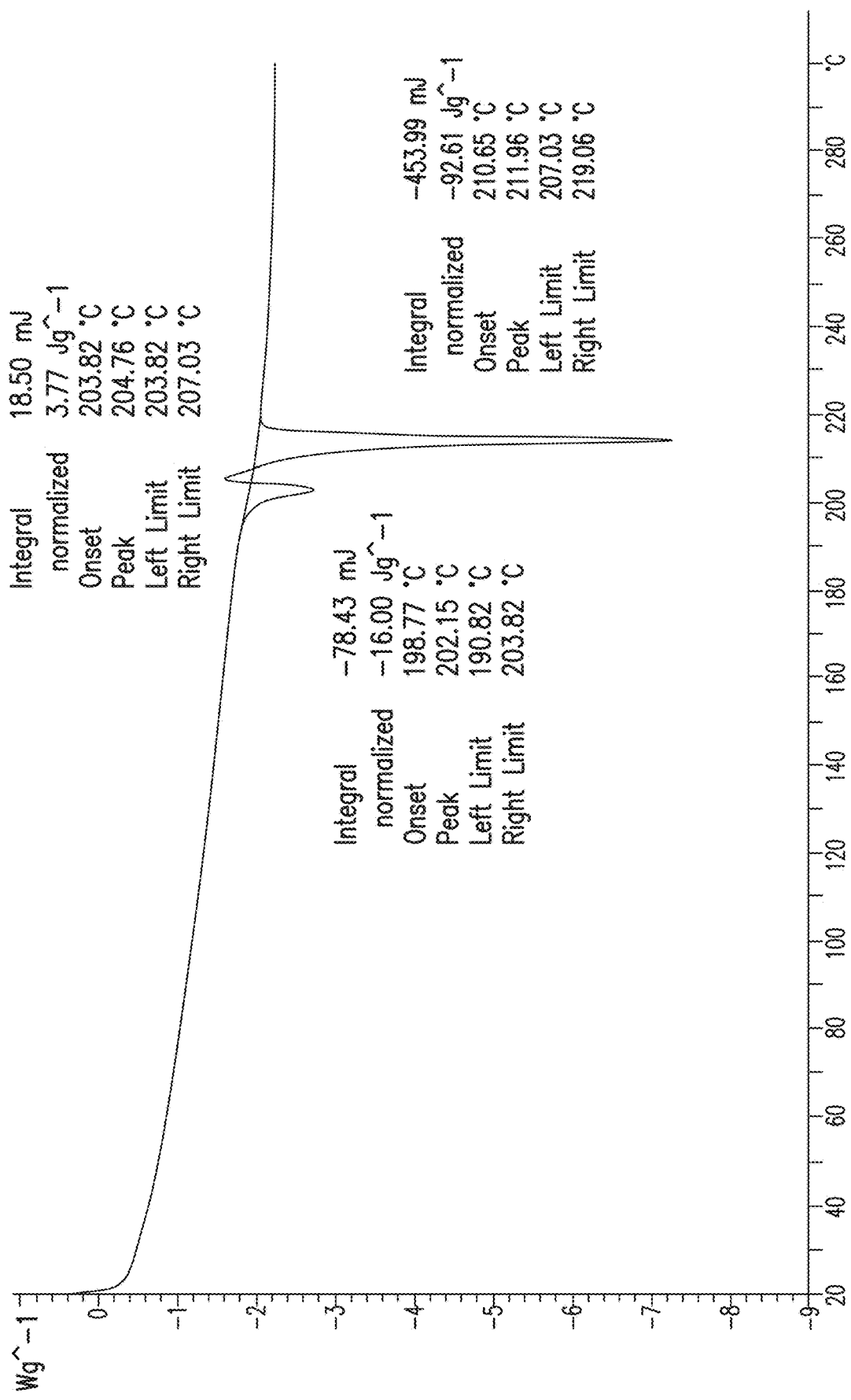
FIG. 7. Illustrates the DSC of crude sample (Form A) with two melting endotherms: 202° C. (peak, Form A) and 212° C. (peak, likely Form G).

The crystalline form of the compound of formula (I) (e.g., Form A) can include an endothermic event with an onset temperature of about 199° C. and about 211° C. as measured by differential scanning calorimetry (DSC). The crystalline form of the compound of formula (I) (e.g., Form A) can be characterized by a DSC plot set forth in FIG. 7. The crystalline form of the compound of formula (I) can have a melting point of about 202° C. The crystalline form of the compound of formula (I) can be Form A, where Form A has a melting point of about 202° C.

The crystalline forms of the compound of formula (I) described herein can be further characterized by TGA as described herein. In embodiments, the crystalline form of the compound of formula (I) (e.g., Form A) can have a mass loss of about 0.28% when heated from about 25° C. to about 180° C. as measured by TGA. The crystalline form of the compound of formula (I) can be stable between about 0° C. to about 60° C. Form A can be stable between about 0° C. to about 60° C.

In some embodiments, the crystalline form of the compound of formula (I) is characterized by a XRPD pattern that includes angle 2θ peaks (i.e., degrees 2θ) at about 10.7±0.3, 15.2±0.3, 15.5±0.3, 17.5±0.3, 18.6±0.3, 19.7±0.3, 20.9±0.3, 21.8±0.3, 24.2±0.3, 24.7±0.3, and 26.4±0.3. The XRPD pattern of the crystalline form of the compound of formula (I) can further include angle 2θ peaks at about 6.3±0.3, 12.5±0.3, 15.9±0.3, 16.6±0.3, 18.2±0.3, 18.9±0.3, 22.3±0.3, 22.7±0.3, 23.1±0.3, 24.9±0.3, 25.3±0.3, 26.0±0.3, 27.2±0.3, 29.4±0.3, 30.0±0.3, 30.9±0.3, 31.8±0.3, and 35.4±0.3.

In some embodiments, the crystalline form of the compound of formula (I) is characterized by a XRPD pattern that includes angle 2θ peaks at about 6.3±0.3, 10.7±0.3, 15.2±0.3, 15.5±0.3, 12.5±0.3, 15.9±0.3, 16.6±0.3, 17.5±0.3, 18.2±0.3, 18.6±0.3, 18.9±0.3, 19.7±0.3, 20.9±0.3, 21.8±0.3, 22.3±0.3, 22.7±0.3, 23.1±0.3, 24.2±0.3, 24.7±0.3, 24.9±0.3, 25.3±0.3, 26.0±0.3, 26.4±0.3, 27.2±0.3, 29.4±0.3, 30.0±0.3, 30.9±0.3, 31.8±0.3, and 35.4±0.3.

In some embodiments, the crystalline form of the compound of formula (I) is characterized by a XRPD pattern that includes angle 2θ peaks (i.e., degrees 2θ) at about 10.7±0.2, 15.2±0.2, 15.5±0.2, 17.5±0.2, 18.6±0.2, 19.7±0.2, 20.9±0.2, 21.8±0.2, 24.2±0.2, 24.7±0.2, and 26.4±0.2. The XRPD pattern of the crystalline form of the compound of formula (I) can further include angle 2θ peaks at about 6.3±0.2, 12.5±0.2, 15.9±0.2, 16.6±0.2, 18.2±0.2, 18.9±0.2, 22.3±0.2, 22.7±0.2, 23.1±0.2, 24.9±0.2, 25.3±0.2, 26.0±0.2, 27.2±0.2, 29.4±0.2, 30.0±0.2, 30.9±0.2, 31.8±0.2, and 35.4±0.2.

In some embodiments, the crystalline form of the compound of formula (I) is characterized by a XRPD pattern that includes angle 2θ peaks at about 6.3±0.2, 10.7±0.2, 15.2±0.2, 15.5±0.2, 12.5±0.2, 15.9±0.2, 16.6±0.2, 17.5±0.2, 18.2±0.2, 18.6±0.2, 18.9±0.2, 19.7±0.2, 20.9±0.2, 21.8±0.2, 22.3±0.2, 22.7±0.2, 23.1±0.2, 24.2±0.2, 24.7±0.2, 24.9±0.2, 25.3±0.2, 26.0±0.2, 26.4±0.2, 27.2±0.2, 29.4±0.2, 30.0±0.2, 30.9±0.2, 31.8±0.2, and 35.4±0.2.

In some embodiments, the crystalline form of the compound of formula (I) is characterized by a XRPD pattern that includes angle 2θ peaks (i.e., degrees 2θ) at about 10.7±0.1, 15.2±0.1, 15.5±0.1, 17.5±0.1, 18.6±0.1, 19.7±0.1, 20.9±0.1, 21.8±0.1, 24.2±0.1, 24.7±0.1, and 26.4±0.1. The XRPD pattern of the crystalline form of the compound of formula (I) can further include angle 2θ peaks at about 6.3±0.1, 12.5±0.1, 15.9±0.1, 16.6±0.1, 18.2±0.1, 18.9±0.1, 22.3±0.1, 22.7±0.1, 23.1±0.1, 24.9±0.1, 25.3±0.1, 26.0±0.1, 27.2±0.1, 29.4±0.1, 30.0±0.1, 30.9±0.1, 31.8±0.1, and 35.4±0.2.

In some embodiments, the crystalline form of the compound of formula (I) is characterized by a XRPD pattern that includes angle 2θ peaks at about 6.3±0.1, 10.7±0.1, 15.2±0.1, 15.5±0.1, 12.5±0.1, 15.9±0.1, 16.6±0.1, 17.5±0.1, 18.2±0.1, 18.6±0.1, 18.9±0.1, 19.7±0.1, 20.9±0.1, 21.8±0.1, 22.3±0.1, 22.7±0.1, 23.1±0.1, 24.2±0.1, 24.7±0.1, 24.9±0.1, 25.3±0.1, 26.0±0.1, 26.4±0.1, 27.2±0.1, 29.4±0.1, 30.0±0.1, 30.9±0.1, 31.8±0.1, and 35.4±0.1.

In some embodiments, the crystalline form of the compound of formula (I) is characterized by a XRPD pattern that includes angle 2θ peaks (i.e., degrees 2θ) at about 10.7, 15.2, 15.5, 17.5, 18.6, 19.7, 20.9, 21.8, 24.2, 24.7, and 26.4. The XRPD pattern of the crystalline form of the compound of formula (I) can further include angle 2θ peaks at about 6.3, 12.5, 15.9, 16.6, 18.2, 18.9, 22.3, 22.7, 23.1, 24.9, 25.3, 26.0, 27.2, 29.4, 30.0, 30.9, 31.8, and 35.4.

In some embodiments, the crystalline form of the compound of formula (I) is characterized by a XRPD pattern that includes angle 2θ peaks at about 6.3, 10.7, 15.2, 15.5, 12.5, 15.9, 16.6, 17.5, 18.2, 18.6, 18.9, 19.7, 20.9, 21.8, 22.3, 22.7, 23.1, 24.2, 24.7, 24.9, 25.3, 26.0, 26.4, 27.2, 29.4, 30.0, 30.9, 31.8, and 35.4.

Figure 43:
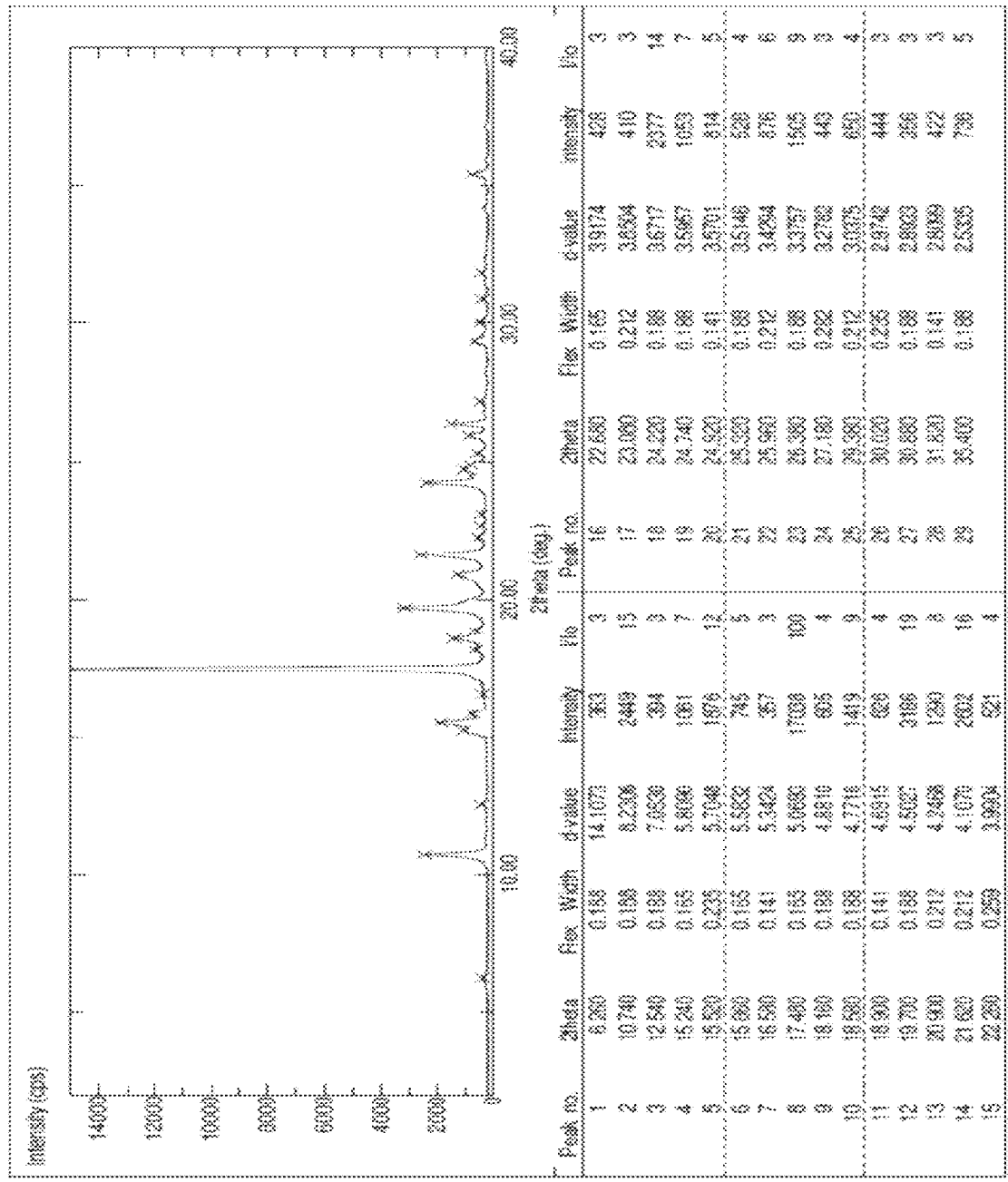
FIG. 43. Illustrates the XRPD of form B.

In certain embodiments, the crystalline form of the compound of formula (I) is characterized by a XRPD pattern corresponding substantially to FIG. 43.

In some embodiments, the crystalline form of the compound of formula (I) is characterized by a XRPD pattern that includes d spacings at about 8.23±0.3, 5.80±0.3, 5.70±0.3, 5.06±0.3, 4.77±0.3, 4.50±0.3, 4.24±0.3, 4.10±0.3, 3.67±0.3, 3.59±0.3, and 3.37±0.3. The XRPD pattern of the crystalline form of the compound of formula (I) can be further characterized by d spacings at about 14.10±0.3, 7.05±0.3, 5.58±0.3, 5.34±0.3, 4.88±0.3, 4.69±0.3, 3.99±0.3, 3.91±0.3, 3.85±0.3, 3.57±0.3, 3.51±0.3, 3.42±0.3, 3.27±0.3, 3.03±0.3, 2.97±0.3, 2.89±0.3, 2.80±0.3, and 2.53±0.3.

In some embodiments, the crystalline form of the compound of formula (I) is characterized by a XRPD pattern that includes d spacings at about 14.10±0.3, 8.23±0.3, 7.05±0.3, 5.80±0.3, 5.70±0.3, 5.58±0.3, 5.34±0.3, 5.06±0.3, 4.88±0.3, 4.77±0.3, 4.69±0.3, 4.50±0.3, 4.24±0.3, 4.10±0.3, 3.99±0.3, 3.91±0.3, 3.85±0.3, 3.67±0.3, 3.59±0.3, 3.57±0.3, 3.51±0.3, 3.42±0.3, 3.37±0.3, 3.27±0.3, 3.03±0.3, 2.97±0.3, 2.89±0.3, 2.80±0.3, and 2.53±0.3.

In some embodiments, the crystalline form of the compound of formula (I) is characterized by a XRPD pattern that includes d spacings at about 8.23±0.2, 5.80±0.2, 5.70±0.2, 5.06±0.2, 4.77±0.2, 4.50±0.2, 4.24±0.2, 4.10±0.2, 3.67±0.2, 3.59±0.2, and 3.37±0.2. The XRPD pattern of the crystalline form of the compound of formula (I) can be further characterized by d spacings at about 14.10±0.2, 7.05±0.2, 5.58±0.2, 5.34±0.2, 4.88±0.2, 4.69±0.2, 3.99±0.2, 3.91±0.2, 3.85±0.2, 3.57±0.2, 3.51±0.2, 3.42±0.2, 3.27±0.2, 3.03±0.2, 2.97±0.2, 2.89±0.2, 2.80±0.2, and 2.53±0.2.

In some embodiments, the crystalline form of the compound of formula (I) is characterized by a XRPD pattern that includes d spacings at about 14.10±0.2, 8.23±0.2, 7.05±0.2, 5.80±0.2, 5.70±0.2, 5.58±0.2, 5.34±0.2, 5.06±0.2, 4.88±0.2, 4.77±0.2, 4.69±0.2, 4.50±0.2, 4.24±0.2, 4.10±0.2, 3.99±0.2, 3.91±0.2, 3.85±0.2, 3.67±0.2, 3.59±0.2, 3.57±0.2, 3.51±0.2, 3.42±0.2, 3.37±0.2, 3.27±0.2, 3.03±0.2, 2.97±0.2, 2.89±0.2, 2.80±0.2, and 2.53±0.2.

In some embodiments, the crystalline form of the compound of formula (I) is characterized by a XRPD pattern that includes d spacings at about 8.23±0.1, 5.80±0.1, 5.70±0.1, 5.06±0.1, 4.77±0.1, 4.50±0.1, 4.24±0.1, 4.10±0.1, 3.67±0.1, 3.59±0.1, and 3.37±0.1. The XRPD pattern of the crystalline form of the compound of formula (I) can be further characterized by d spacings at about 14.10±0.1, 7.05±0.1, 5.58±0.1, 5.34±0.1, 4.88±0.1, 4.69±0.1, 3.99±0.1, 3.91±0.1, 3.85±0.1, 3.57±0.1, 3.51±0.1, 3.42±0.1, 3.27±0.1, 3.03±0.1, 2.97±0.1, 2.89±0.1, 2.80±0.1, and 2.53±0.1.

In some embodiments, the crystalline form of the compound of formula (I) is characterized by a XRPD pattern that includes d spacings at about 14.10±0.1, 8.23±0.1, 7.05±0.1, 5.80±0.1, 5.70±0.1, 5.58±0.1, 5.34±0.1, 5.06±0.1, 4.88±0.1, 4.77±0.1, 4.69±0.1, 4.50±0.1, 4.24±0.1, 4.10±0.1, 3.99±0.1, 3.91±0.1, 3.85±0.1, 3.67±0.1, 3.59±0.1, 3.57±0.1, 3.51±0.1, 3.42±0.1, 3.37±0.1, 3.27±0.1, 3.03±0.1, 2.97±0.1, 2.89±0.1, 2.80±0.1, and 2.53±0.1.

In some embodiments, the crystalline form of the compound of formula (I) is characterized by a XRPD pattern that includes d spacings at about 8.23, 5.80, 5.70, 5.06, 4.77, 4.50, 4.24, 4.10, 3.67, 3.59, and 3.37. The XRPD pattern of the crystalline form of the compound of formula (I) can be further characterized by d spacings at about 14.10, 7.05, 5.58, 5.34, 4.88, 4.69, 3.99, 3.91, 3.85, 3.57, 3.51, 3.42, 3.27, 3.03, 2.97, 2.89, 2.80, and 2.53.

In some embodiments, the crystalline form of the compound of formula (I) is characterized by a XRPD pattern that includes d spacings at about 14.10, 8.23, 7.05, 5.80, 5.70, 5.58, 5.34, 5.06, 4.88, 4.77, 4.69, 4.50, 4.24, 4.10, 3.99, 3.91, 3.85, 3.67, 3.59, 3.57, 3.51, 3.42, 3.37, 3.27, 3.03, 2.97, 2.89, 2.80, and 2.53.

The crystalline form of the compound of formula (I) can be Form B, where Form B is characterized by the XRPD pattern described above or by FIG. 43.

Figure 11:
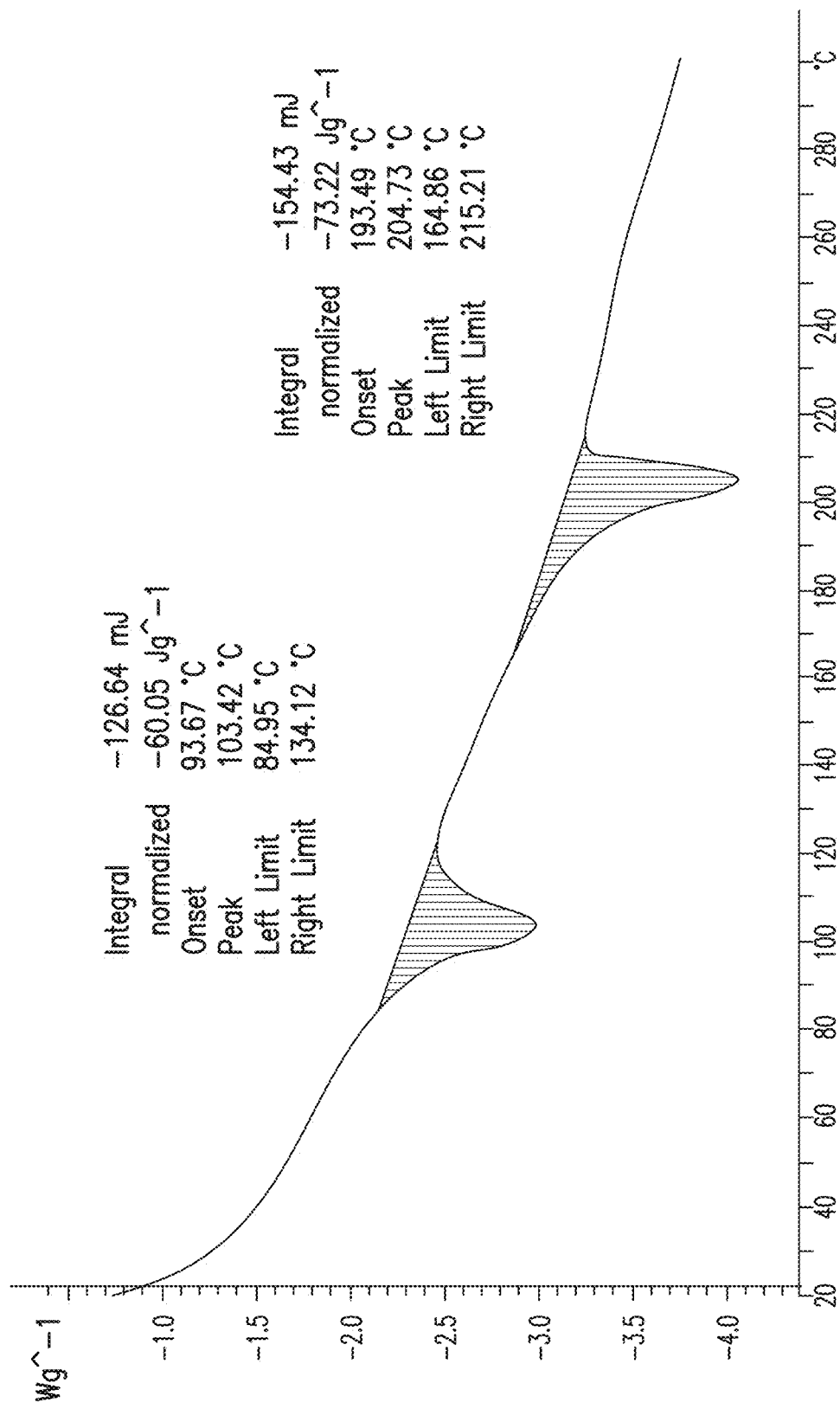
FIG. 11. Illustrates the DSC of form B (Table 1 experiment A1_10) with two endotherms. The endotherm of about 100° C. likely corresponds to dioxane release.

The crystalline form of the compound of formula (I) (e.g., Form B) can include an endothermic event with an onset temperature of about 94° C. and about 193° C. as determined by DSC. The crystalline form of the compound of formula (I) (e.g., Form B) can be characterized by a DSC plot set forth in FIG. 11. The crystalline form of the compound of formula (I) can have a melting point of about 204° C. The crystalline form of the compound of formula (I) can be Form B, where Form B has a melting point of about 204° C.

Form B can have a mass loss of about 12% when heated from about 80° C. to about 140° C. Form B can be a solvated crystalline form, where Form B is a 1,4-dioxane solvate.

In some embodiments, the crystalline form of the compound of formula (I) includes angle 2θ peaks (i.e., degrees 2θ) at about 11.0±0.3, 14.9±0.3, 18.0±0.3, 19.1±0.3, 21.0±0.3, and 22.8±0.3. The XRPD pattern of the crystalline form of the compound of formula (I) can further include angle 2θ peaks at about 5.6±0.3, 8.9±0.3, 9.6±0.3, 10.6±0.3, 13.5±0.3, 14.4±0.3, 15.3±0.3, 16.1±0.3, 16.9±0.3, 17.2±0.3, 20.3±0.3, 21.7±0.3, 22.1±0.3, 23.5±0.3, 23.9±0.3, 24.7±0.3, 26.8±0.3, 27.3±0.3, and 29.1±0.3.

In some embodiments, the crystalline form of the compound of formula (I) is characterized by a XRPD pattern that includes angle 2θ peaks at about 5.6±0.3, 8.9±0.3, 9.6±0.3, 10.6±0.3, 11.0±0.3, 13.5±0.3, 14.4±0.3, 14.9±0.3, 15.3±0.3, 16.1±0.3, 16.9±0.3, 17.2±0.3, 18.0±0.3, 19.1±0.3, 20.3±0.3, 21.0±0.3 21.7±0.3, 22.1±0.3, 22.8±0.3, 23.5±0.3, 23.9±0.3, 24.7±0.3, 26.8±0.3, 27.3±0.3, and 29.1±0.3.

In some embodiments, the crystalline form of the compound of formula (I) includes angle 2θ peaks (i.e., degrees 2θ) at about 11.0±0.2, 14.9±0.2, 18.0±0.2, 19.1±0.2, 21.0±0.2, and 22.8±0.2. The XRPD pattern of the crystalline form of the compound of formula (I) can further include angle 2θ peaks at about 5.6±0.2, 8.9±0.2, 9.6±0.2, 10.6±0.2, 13.5±0.2, 14.4±0.2, 15.3±0.2, 16.1±0.2, 16.9±0.2, 17.2±0.2, 20.3±0.2, 21.7±0.2, 22.1±0.2, 23.5±0.2, 23.9±0.2, 24.7±0.2, 26.8±0.2, 27.3±0.2, and 29.1±0.2.

In some embodiments, the crystalline form of the compound of formula (I) is characterized by a XRPD pattern that includes angle 2θ peaks at about 5.6±0.2, 8.9±0.2, 9.6±0.2, 10.6±0.2, 11.0±0.2, 13.5±0.2, 14.4±0.2, 14.9±0.2, 15.3±0.2, 16.1±0.2, 16.9±0.2, 17.2±0.2, 18.0±0.2, 19.1±0.2, 20.3±0.2, 21.0±0.2 21.7±0.2, 22.1±0.2, 22.8±0.2, 23.5±0.2, 23.9±0.2, 24.7±0.2, 26.8±0.2, 27.3±0.2, and 29.1±0.2.

In some embodiments, the crystalline form of the compound of formula (I) includes angle 2θ peaks (i.e., degrees 2θ) at about 11.0±0.1, 14.9±0.1, 18.0±0.1, 19.1±0.1, 21.0±0.1, and 22.8±0.1. The XRPD pattern of the crystalline form of the compound of formula (I) can further include angle 2θ peaks at about 5.6±0.1, 8.9±0.1, 9.6±0.1, 10.6±0.1, 13.5±0.1, 14.4±0.1, 15.3±0.1, 16.1±0.1, 16.9±0.1, 17.2±0.1, 20.3±0.1, 21.7±0.1, 22.1±0.1, 23.5±0.1, 23.9±0.1, 24.7±0.1, 26.8±0.1, 27.3±0.1, and 29.1±0.1.

In some embodiments, the crystalline form of the compound of formula (I) is characterized by a XRPD pattern that includes angle 2θ peaks at about 5.6±0.1, 8.9±0.1, 9.6±0.1, 10.6±0.1, 11.0±0.1, 13.5±0.1, 14.4±0.1, 14.9±0.1, 15.3±0.1, 16.1±0.1, 16.9±0.1, 17.2±0.1, 18.0±0.1, 19.1±0.1, 20.3±0.1, 21.0±0.1, 21.7±0.1, 22.1±0.1, 22.8±0.1, 23.5±0.1, 23.9±0.1, 24.7±0.1, 26.8±0.1, 27.3±0.1, and 29.1±0.1.

In some embodiments, the crystalline form of the compound of formula (I) includes angle 2θ peaks (i.e., degrees 2θ) at about 11.0, 14.9, 18.0, 19.1, 21.0, and 22.8. The XRPD pattern of the crystalline form of the compound of formula (I) can further include angle 2θ peaks at about 5.6, 8.9, 9.6, 10.6, 13.5, 14.4, 15.3, 16.1, 16.9, 17.2, 20.3, 21.7, 22.1, 23.5, 23.9, 24.7, 26.8, 27.3, and 29.1.

In some embodiments, the crystalline form of the compound of formula (I) is characterized by a XRPD pattern that includes angle 2θ peaks at about 5.6, 8.9, 9.6, 10.6, 11.0, 13.5, 14.4, 14.9, 15.3, 16.1, 16.9, 17.2, 18.0, 19.1, 20.3, 21.0, 21.7, 22.1, 22.8, 23.5, 23.9, 24.7, 26.8, 27.3, and 29.

Figure 44:
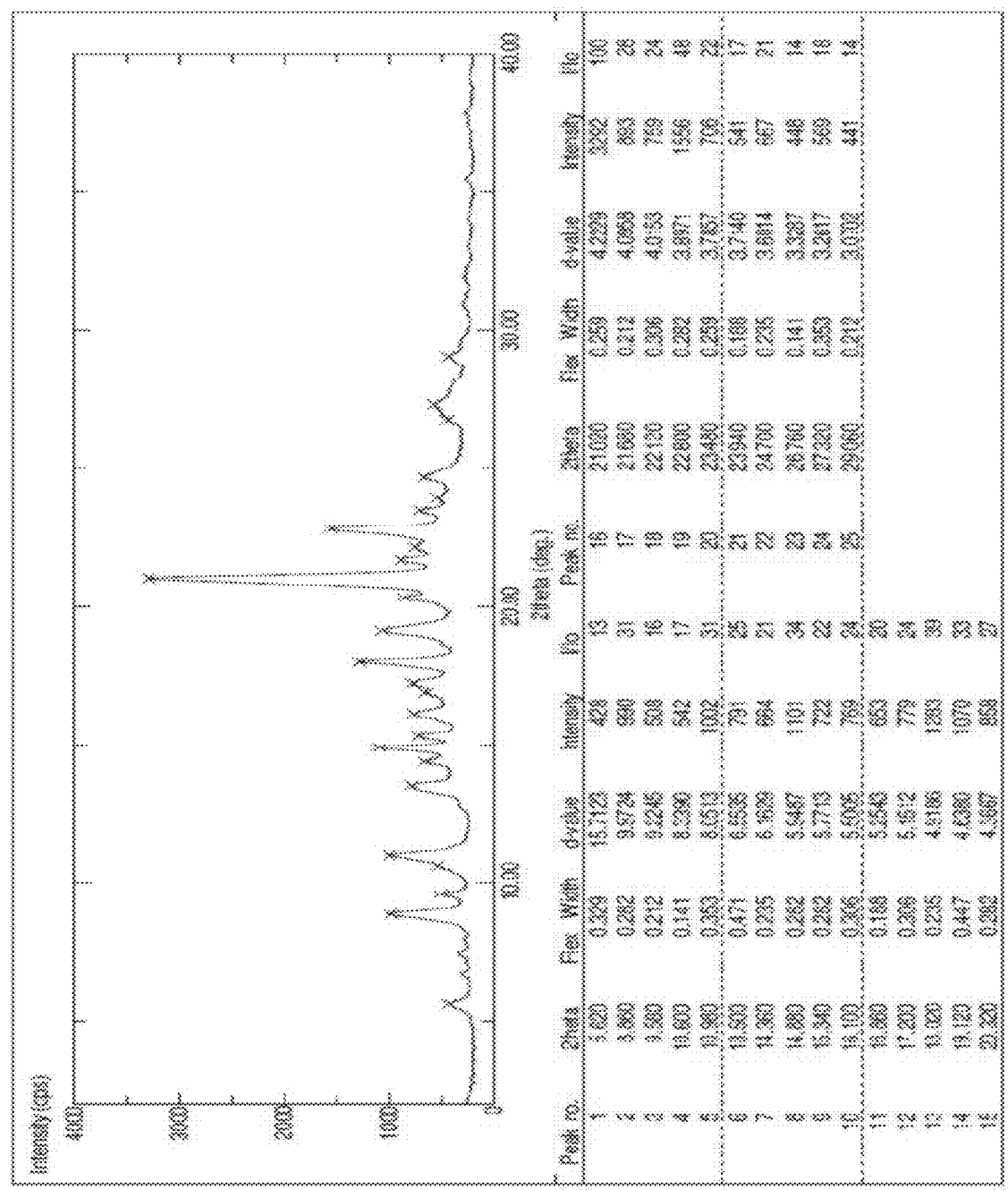
FIG. 44. Illustrates the XRPD of form C.

In certain embodiments, the crystalline form of the compound of formula (I) is characterized by a XRPD pattern corresponding substantially to FIG. 44.

In some embodiments, the crystalline form of the compound of formula (I) is characterized by a XRPD pattern that includes d spacings at about 8.05±0.3, 5.94±0.3, 4.91±0.3, 4.63±0.3, 4.22±0.3, and 3.89±0.3. The XRPD pattern of the crystalline form of the compound of formula (I) can be further characterized by d spacings at about 15.71±0.3, 9.97±0.3, 9.22±0.3, 8.33±0.3, 6.55±0.3, 6.16±0.3, 5.77±0.3, 5.50±0.3, 5.25±0.3, 5.15±0.3, 4.36±0.3, 4.09±0.3, 4.01±0.3, 3.78±0.3, 3.71±0.3, 3.60±0.3, 3.32±0.3, 3.26±0.3, and 3.07±0.3.

In some embodiments, the crystalline form of the compound of formula (I) is characterized by a XRPD pattern that includes d spacings at about 15.71±0.3, 9.97±0.3, 9.22±0.3, 8.33±0.3, 8.05±0.3, 6.55±0.3, 6.16±0.3, 5.94±0.3, 5.77±0.3, 5.50±0.3, 5.25±0.3, 5.15±0.3, 4.91±0.3, 4.63±0.3, 4.36±0.3, 4.22±0.3, 4.09±0.3, 4.01±0.3, 3.89±0.3, 3.78±0.3, 3.71±0.3, 3.60±0.3, 3.32±0.3, 3.26±0.3, and 3.07±0.3.

In some embodiments, the crystalline form of the compound of formula (I) is characterized by a XRPD pattern that includes d spacings at about 8.05±0.2, 5.94±0.2, 4.91±0.2, 4.63±0.2, 4.22±0.2, and 3.89±0.2. The XRPD pattern of the crystalline form of the compound of formula (I) can be further characterized by d spacings at about 15.71±0.2, 9.97±0.2, 9.22±0.2, 8.33±0.2, 6.55±0.2, 6.16±0.2, 5.77±0.2, 5.50±0.2, 5.25±0.2, 5.15±0.2, 4.36±0.2, 4.09±0.2, 4.01±0.2, 3.78±0.2, 3.71±0.2, 3.60±0.2, 3.32±0.2, 3.26±0.2, and 3.07±0.2.

In some embodiments, the crystalline form of the compound of formula (I) is characterized by a XRPD pattern that includes d spacings at about 15.71±0.2, 9.97±0.2, 9.22±0.2, 8.33±0.2, 8.05±0.2, 6.55±0.2, 6.16±0.2, 5.94±0.2, 5.77±0.2, 5.50±0.2, 5.25±0.2, 5.15±0.2, 4.91±0.2, 4.63±0.2, 4.36±0.2, 4.22±0.2, 4.09±0.2, 4.01±0.2, 3.89±0.2, 3.78±0.2, 3.71±0.2, 3.60±0.2, 3.32±0.2, 3.26±0.2, and 3.07±0.2.

In some embodiments, the crystalline form of the compound of formula (I) is characterized by a XRPD pattern that includes d spacings at about 8.05±0.1, 5.94±0.1, 4.91±0.1, 4.63±0.1, 4.22±0.1, and 3.89±0.1. The XRPD pattern of the crystalline form of the compound of formula (I) can be further characterized by d spacings at about 15.71±0.1, 9.97±0.1, 9.22±0.1, 8.33±0.1, 6.55±0.1, 6.16±0.1, 5.77±0.1, 5.50±0.1, 5.25±0.1, 5.15±0.1, 4.36±0.1, 4.09±0.1, 4.01±0.1, 3.78±0.1, 3.71±0.1, 3.60±0.1, 3.32±0.1, 3.26±0.1, and 3.07±0.1.

In some embodiments, the crystalline form of the compound of formula (I) is characterized by a XRPD pattern that includes d spacings at about 15.71±0.1, 9.97±0.1, 9.22±0.1, 8.33±0.1, 8.05±0.1, 6.55±0.1, 6.16±0.1, 5.94±0.1, 5.77±0.1, 5.50±0.1, 5.25±0.1, 5.15±0.1, 4.91±0.1, 4.63±0.1, 4.36±0.1, 4.22±0.1, 4.09±0.1, 4.01±0.1, 3.89±0.1, 3.78±0.1, 3.71±0.1, 3.60±0.1, 3.32±0.1, 3.26±0.1, and 3.07±0.1.

In some embodiments, the crystalline form of the compound of formula (I) is characterized by a XRPD pattern that includes d spacings at about 8.05, 5.94, 4.91, 4.63, 4.22, and 3.89. The XRPD pattern of the crystalline form of the compound of formula (I) can be further characterized by d spacings at about 15.71, 9.97, 9.22, 8.33, 6.55, 6.16, 5.77, 5.50, 5.25, 5.15, 4.36, 4.09, 4.01, 3.78, 3.71, 3.60, 3.32, 3.26, and 3.07.

In some embodiments, the crystalline form of the compound of formula (I) is characterized by a XRPD pattern that includes d spacings at about 15.71±0.2, 9.97±0.2, 9.22±0.2, 8.33±0.2, 8.05±0.2, 6.55±0.2, 6.16±0.2, 5.94±0.2, 5.77±0.2, 5.50±0.2, 5.25±0.2, 5.15±0.2, 4.91±0.2, 4.63±0.2, 4.36±0.2, 4.22±0.2, 4.09±0.2, 4.01±0.2, 3.89±0.2, 3.78±0.2, 3.71±0.2, 3.60±0.2, 3.32±0.2, 3.26±0.2, and 3.07±0.2.

The crystalline form of the compound of formula (I) can be Form C, where Form C is characterized by the XRPD pattern described above or by FIG. 44.

Figure 16:
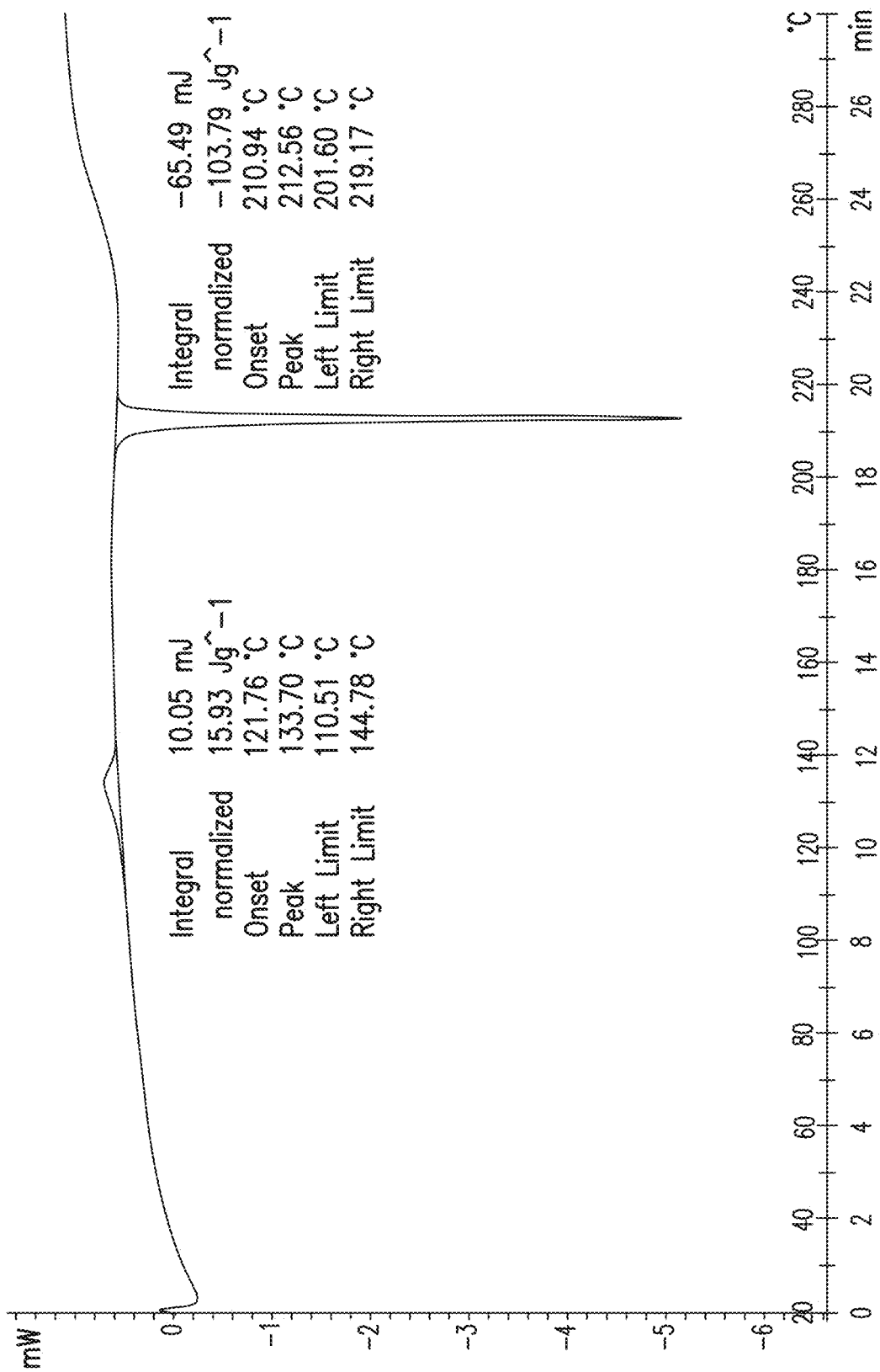
FIG. 16. Illustrates the DSC of form C (pure).

The crystalline form of the compound of formula (I) (e.g., Form C) can include an endothermic event et temperature of about 211° C. as determined by DSC. The crystalline form of the compound of formula (I) (e.g., Form C) can be characterized by a DSC plot set forth in FIG. 16. The crystalline form of the compound of formula (I) can have a melting point of about 213° C. The crystalline form of the compound of formula (I) can be Form C, where Form C has a melting point of about 213° C.

In some embodiments, the crystalline form of the compound of formula (I) is characterized by a XRPD pattern that includes angle 2θ peaks (i.e., degrees 2θ) at about 15.6±0.2, 22.0±0.2, and 23.7±0.2. The XRPD pattern of the crystalline form of the compound of formula (I) can further include angle 2θ peaks at about 6.6±0.2, 7.8±0.2, 9.0±0.2, 10.6±0.2, 13.7±0.2, 14.7±0.2, 16.3±0.2, 17.1±0.2, 18.1±0.2, 18.2±0.2, 18.8±0.2, 19.1±0.2, 19.7±0.2, 20.7±0.2, 21.2±0.2, 22.5±0.2, 25.0±0.2, 26.6±0.2, 27.6±0.2, and 28.7±0.2.

In some embodiments, the crystalline form of the compound of formula (I) is characterized by a XRPD pattern that includes angle 2θ peaks at about 6.6±0.2, 7.8±0.2, 9.0±0.2, 10.6±0.2, 13.7±0.2, 14.7±0.2, 15.6±0.2, 16.3±0.2, 17.1±0.2, 18.1±0.2, 18.2±0.2, 18.8±0.2, 19.1±0.2, 19.7±0.2, 20.7±0.2, 21.2±0.2, 22.0±0.2, 22.5±0.2, 23.7±0.2, 25.0±0.2, 26.6±0.2, 27.6±0.2, and 28.7±0.2.

In some embodiments, the crystalline form of the compound of formula (I) is characterized by a XRPD pattern that includes angle 2θ peaks (i.e., degrees 2θ) at about 15.6±0.1, 22.0±0.1, and 23.7±0.1. The XRPD pattern of the crystalline form of the compound of formula (I) can further include angle 2θ peaks at about 6.6±0.1, 7.8±0.1, 9.0±0.1, 10.6±0.1, 13.7±0.1, 14.7±0.1, 16.3±0.1, 17.1±0.1, 18.1±0.1, 18.2±0.1, 18.8±0.1, 19.1±0.1, 19.7±0.1, 20.7±0.1, 21.2±0.1, 22.5±0.1, 25.0±0.1, 26.6±0.1, 27.6±0.1, and 28.7±0.1.

In some embodiments, the crystalline form of the compound of formula (I) is characterized by a XRPD pattern that includes angle 2θ peaks at about 6.6±0.1, 7.8±0.1, 9.0±0.1, 10.6±0.1, 13.7±0.1, 14.7±0.1, 15.6±0.1, 16.3±0.1, 17.1±0.1, 18.1±0.1, 18.2±0.1, 18.8±0.1, 19.1±0.1, 19.7±0.1, 20.7±0.1, 21.2±0.1, 22.0±0.1, 22.5±0.1, 23.7±0.1, 25.0±0.1, 26.6±0.1, 27.6±0.1, and 28.7±0.1.

In some embodiments, the crystalline form of the compound of formula (I) is characterized by a XRPD pattern that includes angle 2θ peaks (i.e., degrees 2θ) at about 15.6, 22.0, and 23.7. The XRPD pattern of the crystalline form of the compound of formula (I) can further include angle 2θ peaks at about 6.6, 7.8, 9.0, 10.6, 13.7, 14.7, 16.3, 17.1, 18.1, 18.2, 18.8, 19.1, 19.7, 20.7, 21.2, 22.5, 25.0, 26.6, 27.6, and 28.7.

In some embodiments, the crystalline form of the compound of formula (I) is characterized by a XRPD pattern that includes angle 2θ peaks at about 6.6, 7.8, 9.0, 10.6, 13.7, 14.7, 15.6, 16.3, 17.1, 18.1, 18.2, 18.8, 19.1, 19.7, 20.7, 21.2, 22.0, 22.5, 23.7, 25.0, 26.6, 27.6, and 28.7.

Figure 45:
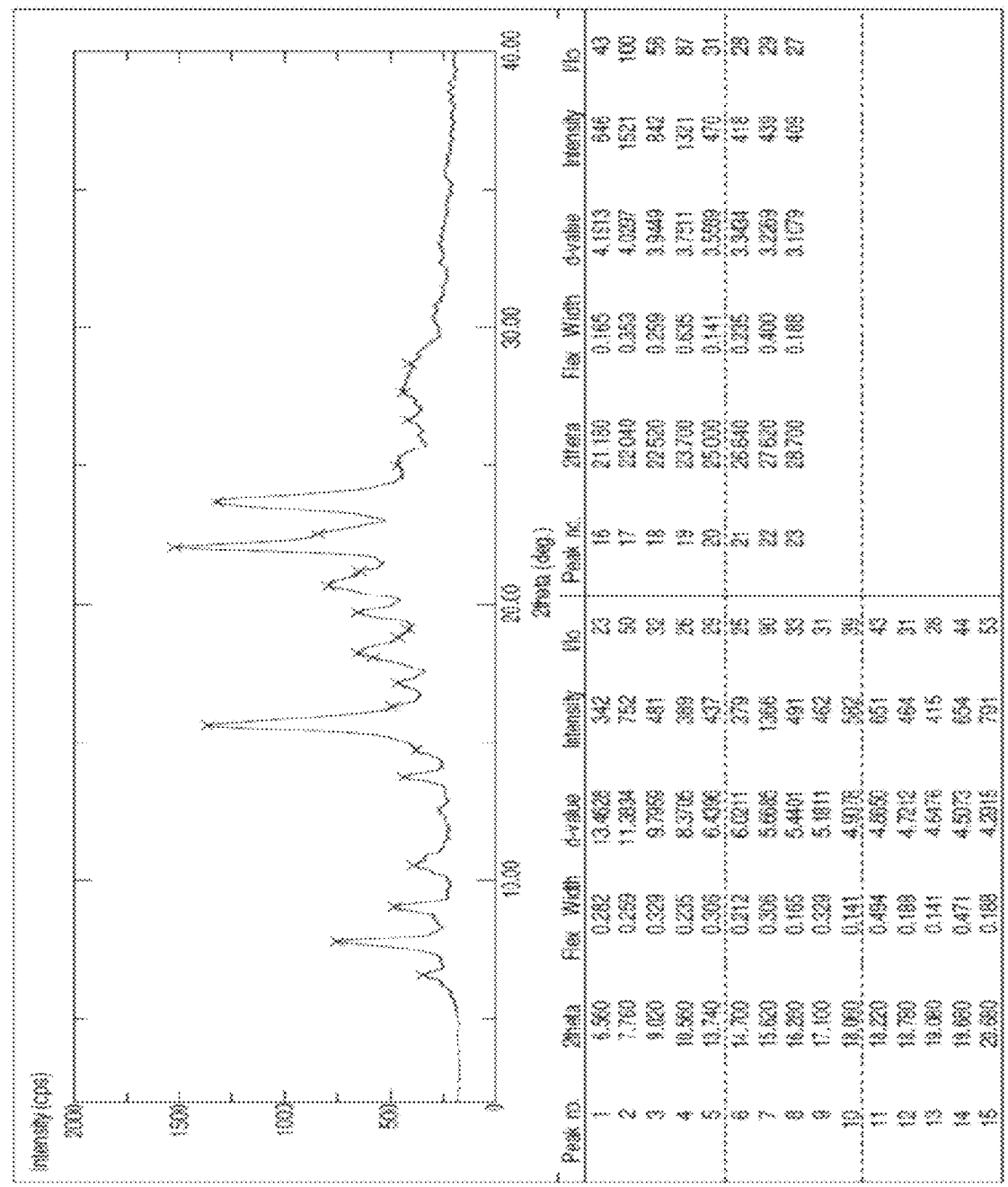
FIG. 45. Illustrates the XRPD of form D.

In certain embodiments, the crystalline form of the compound of formula (I) is characterized by a XRPD pattern corresponding substantially to FIG. 45.

In some embodiments, the crystalline form of the compound of formula (I) is characterized by a XRPD pattern that includes d spacings at about 5.66±0.3, 4.02±0.3, and 3.75±0.3. The XRPD pattern of the crystalline form of the compound of formula (I) can be further characterized by d spacings at about 13.46±0.3, 11.38±0.3, 9.79±0.3, 8.37±0.3, 6.43±0.3, 6.02±0.3, 5.44±0.3, 5.18±0.3, 4.90±0.3, 4.86±0.3, 4.72±0.3, 4.64±0.3, 4.50±0.3, 4.29±0.3, 4.19±0.3, 3.94±0.3, 3.55±0.3, 3.34±0.3, 3.22±0.3, and 3.10±0.3.

In some embodiments, the crystalline form of the compound of formula (I) is characterized by a XRPD pattern that includes d spacings at about 13.46±0.3, 11.38±0.3, 9.79±0.3, 8.37±0.3, 6.43±0.3, 6.02±0.3, 5.66±0.3, 5.44±0.3, 5.18±0.3, 4.90±0.3, 4.86±0.3, 4.72±0.3, 4.64±0.3, 4.50±0.3, 4.29±0.3, 4.19±0.3, 4.02±0.3, 3.94±0.3, 3.75±0.3, 3.55±0.3, 3.34±0.3, 3.22±0.3, and 3.10±0.3.

In some embodiments, the crystalline form of the compound of formula (I) is characterized by a XRPD pattern that includes d spacings at about 5.66±0.2, 4.02±0.2, and 3.75±0.2. The XRPD pattern of the crystalline form of the compound of formula (I) can be further characterized by d spacings at about 13.46±0.2, 11.38±0.2, 9.79±0.2, 8.37±0.2, 6.43±0.2, 6.02±0.2, 5.44±0.2, 5.18±0.2, 4.90±0.2, 4.86±0.2, 4.72±0.2, 4.64±0.2, 4.50±0.2, 4.29±0.2, 4.19±0.2, 3.94±0.2, 3.55±0.2, 3.34±0.2, 3.22±0.2, and 3.10±0.2.

In some embodiments, the crystalline form of the compound of formula (I) is characterized by a XRPD pattern that includes d spacings at about 13.46±0.2, 11.38±0.2, 9.79±0.2, 8.37±0.2, 6.43±0.2, 6.02±0.2, 5.66±0.2, 5.44±0.2, 5.18±0.2, 4.90±0.2, 4.86±0.2, 4.72±0.2, 4.64±0.2, 4.50±0.2, 4.29±0.2, 4.19±0.2, 4.02±0.2, 3.94±0.2, 3.75±0.2, 3.55±0.2, 3.34±0.2, 3.22±0.2, and 3.10±0.2.

In some embodiments, the crystalline form of the compound of formula (I) is characterized by a XRPD pattern that includes d spacings at about 5.66±0.1, 4.02±0.1, and 3.75±0.1. The XRPD pattern of the crystalline form of the compound of formula (I) can be further characterized by d spacings at about 13.46±0.1, 11.38±0.1, 9.79±0.1, 8.37±0.1, 6.43±0.1, 6.02±0.1, 5.44±0.1, 5.18±0.1, 4.90±0.1, 4.86±0.1, 4.72±0.1, 4.64±0.1, 4.50±0.1, 4.29±0.1, 4.19±0.1, 3.94±0.1, 3.55±0.1, 3.34±0.1, 3.22±0.1, and 3.10±0.1.

In some embodiments, the crystalline form of the compound of formula (I) is characterized by a XRPD pattern that includes d spacings at about 13.46±0.1, 11.38±0.1, 9.79±0.1, 8.37±0.1, 6.43±0.1, 6.02±0.1, 5.66±0.1, 5.44±0.1, 5.18±0.1, 4.90±0.1, 4.86±0.1, 4.72±0.1, 4.64±0.1, 4.50±0.1, 4.29±0.1, 4.19±0.1, 4.02±0.1, 3.94±0.1, 3.75±0.1, 3.55±0.1, 3.34±0.1, 3.22±0.1, and 3.10±0.1.

In some embodiments, the crystalline form of the compound of formula (I) is characterized by a XRPD pattern that includes d spacings at about 5.66, 4.02, and 3.75. The XRPD pattern of the crystalline form of the compound of formula (I) can be further characterized by d spacings at about 13.46, 11.38, 9.79, 8.37, 6.43, 6.02, 5.44, 5.18, 4.90, 4.86, 4.72, 4.64, 4.50, 4.29, 4.19, 3.94, 3.55, 3.34, 3.22, and 3.10.

In some embodiments, the crystalline form of the compound of formula (I) is characterized by a XRPD pattern that includes d spacings at about 13.46, 11.38, 9.79, 8.37, 6.43, 6.02, 5.66, 5.44, 5.18, 4.90, 4.86, 4.72, 4.64, 4.50, 4.29, 4.19, 4.02, 3.94, 3.75, 3.55, 3.34, 3.22, and 3.10.

The crystalline form of the compound of formula (I) can be Form D, where Form D is characterized by the XRPD pattern described above or by FIG. 45.

Figure 19:
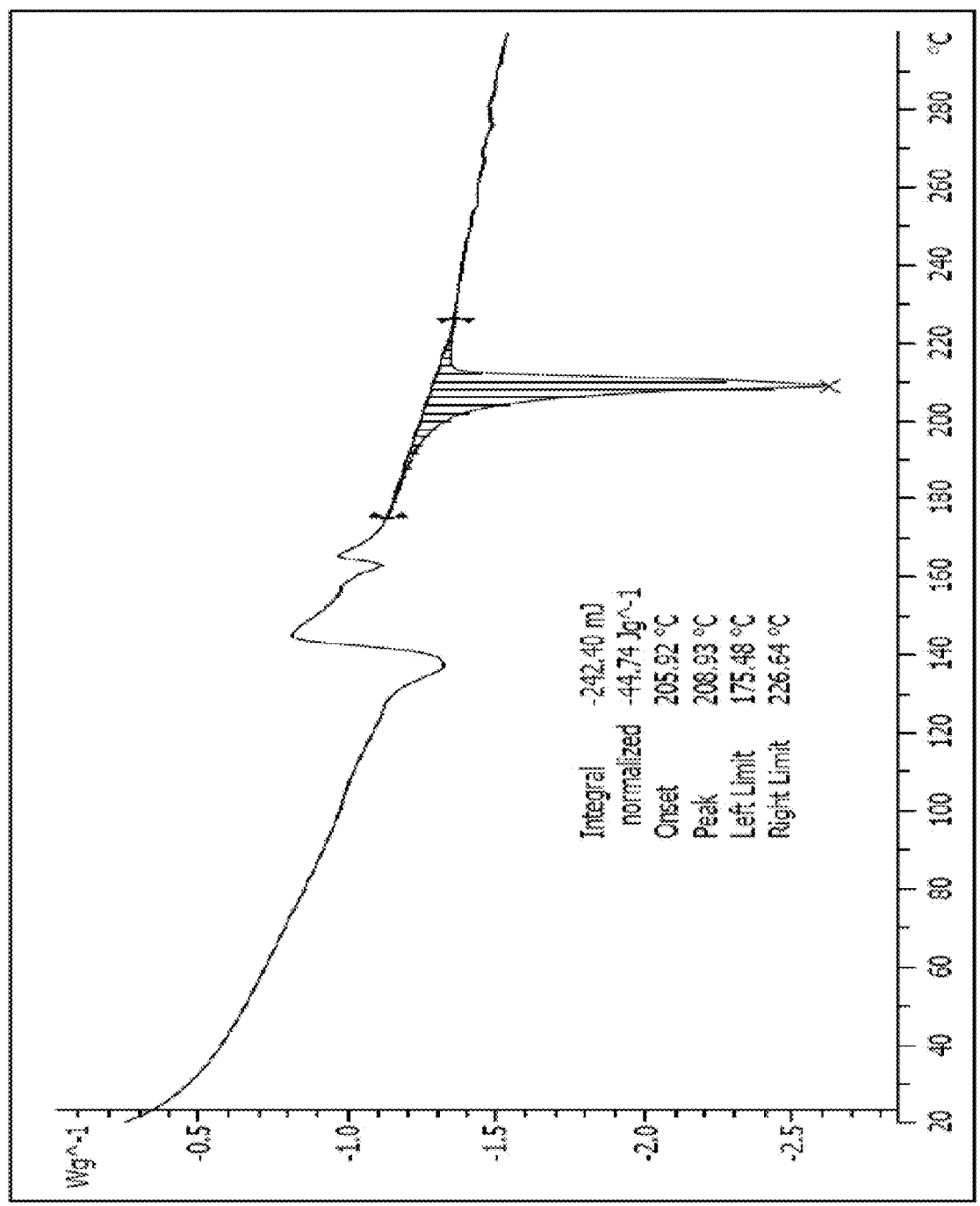
FIG. 19. Illustrates the DSC of form D (Table 3 experiment C3_2) with two endotherm/exotherm combinations at about 140° C. and about 160° C. (both not integrated) and a melting endotherm at about 209° C. (peak).

The crystalline form of the compound of formula (I) (e.g., Form D) can include an endothermic event with an onset temperature of about 205° C. as determined by DSC. The crystalline form of the compound of formula (I) can be characterized by a DSC plot set forth in FIG. 19. The crystalline form of the compound of formula (I) can have a melting point of about 209° C. The crystalline form of the compound of formula (I) can be Form D, where Form D has a melting point of about 209° C.

The crystalline form of the compound of formula (I) (e.g., Form D) can have a mass loss of about 13% when heated from about 35° C. to about 153° C. Form D can be a solvated crystalline form, where Form D is a dichloromethane solvate.

In some embodiments, the crystalline form of the compound of formula (I) can be characterized by a XRPD pattern that includes angle 2θ peaks (i.e., degrees 2θ) at about 8.8±0.3, 17.7±0.3, and 21.4±0.3. The XRPD pattern of the crystalline form of the compound of formula (I) can further include angle 2θ peaks at about 5.4±0.3, 9.3±0.3, 12.1±0.3, 13.4±0.3, 13.8±0.3, 18.0±0.3, 16.5±0.3, 18.3±0.3, 18.9±0.3, 19.5±0.3, 22.2±0.3, 22.6±0.3, 22.9±0.3, 23.3±0.3, 23.5±0.3, 24.4±0.3, 26.2±0.3, 26.8±0.3, 27.8±0.3, and 29.3±0.3.

In some embodiments, the crystalline form of the compound of formula (I) is characterized by a XRPD pattern that includes angle 2θ peaks at about 5.4±0.3, 8.8±0.3, 9.3±0.3, 12.1±0.3, 13.4±0.3, 13.8±0.3, 17.7±0.3, 18.0±0.3, 16.5±0.3, 18.3±0.3, 18.9±0.3, 19.5±0.3, 21.4±0.3, 22.2±0.3, 22.6±0.3, 22.9±0.3, 23.3±0.3, 23.5±0.3, 24.4±0.3, 26.2±0.3, 26.8±0.3, 27.8±0.3, and 29.3±0.3.

In some embodiments, the crystalline form of the compound of formula (I) is characterized by a XRPD pattern that includes angle 2θ peaks (i.e., degrees 2θ) at about 8.8±0.2, 17.7±0.2, and 21.4±0.2. The XRPD pattern of the crystalline form of the compound of formula (I) can further include angle 2θ peaks at about 5.4±0.2, 9.3±0.2, 12.1±0.2, 13.4±0.2, 13.8±0.2, 18.0±0.2, 16.5±0.2, 18.3±0.2, 18.9±0.2, 19.5±0.2, 22.2±0.2, 22.6±0.2, 22.9±0.2, 23.3±0.2, 23.5±0.2, 24.4±0.2, 26.2±0.2, 26.8±0.2, 27.8±0.2, and 29.3±0.2.

In some embodiments, the crystalline form of the compound of formula (I) is characterized by a XRPD pattern that includes angle 2θ peaks at about 5.4±0.2, 8.8±0.2, 9.3±0.2, 12.1±0.2, 13.4±0.2, 13.8±0.2, 17.7±0.2, 18.0±0.2, 16.5±0.2, 18.3±0.2, 18.9±0.2, 19.5±0.2, 21.4±0.2, 22.2±0.2, 22.6±0.2, 22.9±0.2, 23.3±0.2, 23.5±0.2, 24.4±0.2, 26.2±0.2, 26.8±0.2, 27.8±0.2, and 29.3±0.2.

In some embodiments, the crystalline form of the compound of formula (I) is characterized by a XRPD pattern that includes angle 2θ peaks (i.e., degrees 2θ) at about 8.8±0.1, 17.7±0.1, and 21.4±0.1. The XRPD pattern of the crystalline form of the compound of formula (I) can further include angle 2θ peaks at about 5.4±0.1, 9.3±0.1, 12.1±0.1, 13.4±0.1, 13.8±0.1, 18.0±0.1, 16.5±0.1, 18.3±0.1, 18.9±0.1, 19.5±0.1, 22.2±0.1, 22.6±0.1, 22.9±0.1, 23.3±0.1, 23.5±0.1, 24.4±0.1, 26.2±0.1, 26.8±0.1, 27.8±0.1, and 29.3±0.1.

In some embodiments, the crystalline form of the compound of formula (I) is characterized by a XRPD pattern that includes angle 2θ peaks at about 5.4±0.1, 8.8±0.1, 9.3±0.1, 12.1±0.1, 13.4±0.1, 13.8±0.1, 17.7±0.1, 18.0±0.1, 16.5±0.1, 18.3±0.1, 18.9±0.1, 19.5±0.1, 21.4±0.1, 22.2±0.1, 22.6±0.1, 22.9±0.1, 23.3±0.1, 23.5±0.1, 24.4±0.1, 26.2±0.1, 26.8±0.1, 27.8±0.1, and 29.3±0.1.

In some embodiments, the crystalline form of the compound of formula (I) is characterized by a XRPD pattern that includes angle 2θ peaks (i.e., degrees 2θ) at about 8.8, 17.7, and 21.4. The XRPD pattern of the crystalline form of the compound of formula (I) can further include angle 2θ peaks at about 5.4, 9.3, 12.1, 13.4, 13.8, 18.0, 16.5, 18.3, 18.9, 19.5, 22.2, 22.6, 22.9, 23.3, 23.5, 24.4, 26.2, 26.8, 27.8, and 29.3.

In some embodiments, the crystalline form of the compound of formula (I) is characterized by a XRPD pattern that includes angle 2θ peaks at about 5.4, 8.8, 9.3, 12.1, 13.4, 13.8, 17.7, 18.0, 16.5, 18.3, 18.9, 19.5, 21.4, 22.2, 22.6, 22.9, 23.3, 23.5, 24.4, 26.2, 26.8, 27.8, and 29.3.

Figure 46:
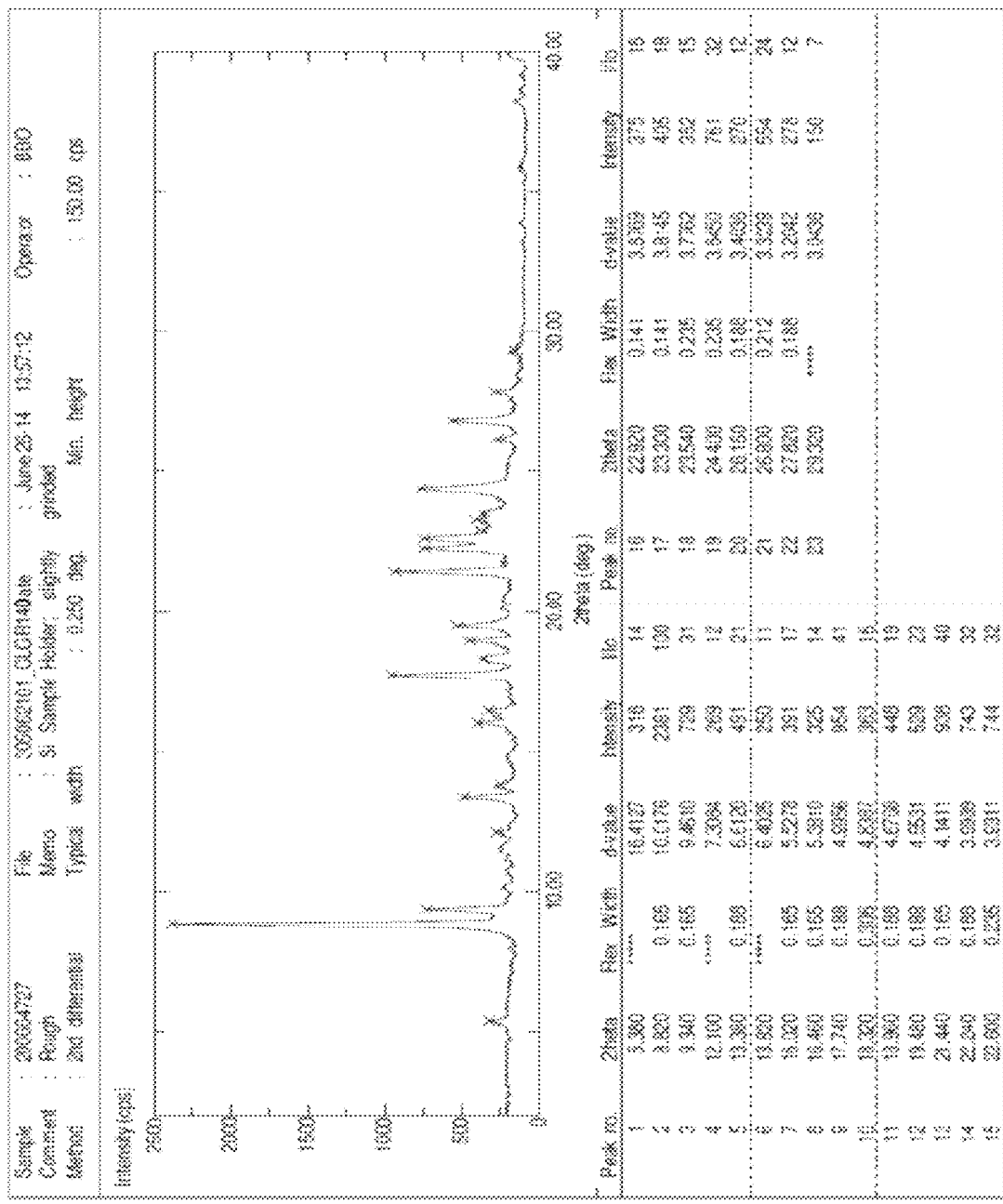
FIG. 46. Illustrates the XRPD of form E.

In certain embodiments, the crystalline form of the compound of formula (I) is characterized by a XRPD pattern corresponding substantially to FIG. 46.

In some embodiments, the crystalline form of the compound of formula (I) is characterized by a XRPD pattern that includes d spacings at about 10.01±0.3, 4.99±0.3, and 4.14±0.3. The XRPD pattern of the crystalline form of the compound of formula (I) can be further characterized by d spacings at about 16.41±0.3, 9.46±0.3, 7.30±0.3, 6.61±0.3, 6.40±0.3, 5.52±0.3, 5.38±0.3, 4.83±0.3, 4.67±0.3, 4.55±0.3, 3.99±0.3, 3.93, ±0.3 3.87±0.3, 3.81±0.3, 3.77±0.3, 3.64±0.3, 3.40±0.3, 3.32±0.3, and 3.04±0.3.

In some embodiments, the crystalline form of the compound of formula (I) is characterized by a XRPD pattern that includes d spacings at about 16.41±0.3, 10.01±0.3, 9.46±0.3, 7.30±0.3, 6.61±0.3, 6.40±0.3, 5.52±0.3, 5.38±0.3, 4.99±0.3, 4.83±0.3, 4.67±0.3, 4.55±0.3, 4.14±0.3, 3.99±0.3, 3.93, ±0.3 3.87±0.3, 3.81±0.3, 3.77±0.3, 3.64±0.3, 3.40±0.3, 3.32±0.3, and 3.04±0.3.

In some embodiments, the crystalline form of the compound of formula (I) is characterized by a XRPD pattern that includes d spacings at about 10.01±0.2, 4.99±0.2, and 4.14±0.2. The XRPD pattern of the crystalline form of the compound of formula (I) can be further characterized by d spacings at about 16.41±0.2, 9.46±0.2, 7.30±0.2, 6.61±0.2, 6.40±0.2, 5.52±0.2, 5.38±0.2, 4.83±0.2, 4.67±0.2, 4.55±0.2, 3.99±0.2, 3.93, ±0.2 3.87±0.2, 3.81±0.2, 3.77±0.2, 3.64±0.2, 3.40±0.2, 3.32±0.2, and 3.04±0.2.

In some embodiments, the crystalline form of the compound of formula (I) is characterized by a XRPD pattern that includes d spacings at about 16.41±0.2, 10.01±0.2, 9.46±0.2, 7.30±0.2, 6.61±0.2, 6.40±0.2, 5.52±0.2, 5.38±0.2, 4.99±0.2, 4.83±0.2, 4.67±0.2, 4.55±0.2, 4.14±0.2, 3.99±0.2, 3.93, ±0.2 3.87±0.2, 3.81±0.2, 3.77±0.2, 3.64±0.2, 3.40±0.2, 3.32±0.2, and 3.04±0.2.

In some embodiments, the crystalline form of the compound of formula (I) is characterized by a XRPD pattern that includes d spacings at about 10.01±0.1, 4.99±0.1, and 4.14±0.1. The XRPD pattern of the crystalline form of the compound of formula (I) can be further characterized by d spacings at about 16.41±0.1, 9.46±0.1, 7.30±0.1, 6.61±0.1, 6.40±0.1, 5.52±0.1, 5.38±0.1, 4.83±0.1, 4.67±0.1, 4.55±0.1, 3.99±0.1, 3.93, ±0.1 3.87±0.1, 3.81±0.1, 3.77±0.1, 3.64±0.1, 3.40±0.1, 3.32±0.1, and 3.04±0.1.

In some embodiments, the crystalline form of the compound of formula (I) is characterized by a XRPD pattern that includes d spacings at about 16.41±0.1, 10.01±0.1, 9.46±0.1, 7.30±0.1, 6.61±0.1, 6.40±0.1, 5.52±0.1, 5.38±0.1, 4.99±0.1, 4.83±0.1, 4.67±0.1, 4.55±0.1, 4.14±0.1, 3.99±0.1, 3.93,±0.1 3.87±0.1, 3.81±0.1, 3.77±0.1, 3.64±0.1, 3.40±0.1, 3.32±0.1, and 3.04±0.1.

In some embodiments, the crystalline form of the compound of formula (I) is characterized by a XRPD pattern that includes d spacings at about 10.01, 4.99, and 4.14. The XRPD pattern of the crystalline form of the compound of formula (I) can be further characterized by d spacings at about 16.41, 9.46, 7.30, 6.61, 6.40, 5.52, 5.38, 4.83, 4.67, 4.55, 3.99, 3.93, 3.87, 3.81, 3.77, 3.64, 3.40, 3.32, and 3.04.

In some embodiments, the crystalline form of the compound of formula (I) is characterized by a XRPD pattern that includes d spacings at about 16.41, 10.01, 9.46, 7.30, 6.61, 6.40, 5.52, 5.38, 4.99, 4.83, 4.67, 4.55, 4.14, 3.99, 3.93, 3.87, 3.81, 3.77, 3.64, 3.40, 3.32, and 3.04.

The crystalline form of the compound of formula (I) can be Form E, where Form E is characterized by the XRPD pattern described above or by FIG. 46.

Form E can be a solvated crystalline form, where Form E is a chlorobenzene solvate.

In some embodiments, the crystalline form of the compound of formula (I) is characterized by a XRPD pattern that includes angle 2θ peaks (i.e., degrees 2θ) at about 4.6±0.3, 4.8±0.3, 15.3±0.3, 16.6±0.3, 18.1±0.3, and 22.9±0.3. The XRPD pattern of the crystalline form of the compound of formula (I) can further include angle 2θ peaks at about 7.3±0.3, 8.1±0.3, 9.7±0.3, 11.0±0.3, 12.2±0.3, 13.8±0.3, 14.8±0.3, 16.1±0.3, 17.5±0.3, 17.9±0.3, 18.5±0.3, 19.8±0.3, 20.2±0.3, 20.8±0.3, 21.5±0.3, 22.2±0.3, 23.4±0.3, 24.0±0.3, 24.8±0.3, 25.2±0.3, 25.8±0.3, 27.5±0.3, 27.9±0.3, and 31.9±0.3.

In some embodiments, the crystalline form of the compound of formula (I) is characterized by a XRPD pattern that includes angle 2θ peaks at about 4.6±0.3, 4.8±0.3, 7.3±0.3, 8.1±0.3, 9.7±0.3, 11.0±0.3, 12.2±0.3, 13.8±0.3, 14.8±0.3, 15.3±0.3, 16.1±0.3, 16.6±0.3, 17.5±0.3, 17.9±0.3, 18.1±0.3, 18.5±0.3, 19.8±0.3, 20.2±0.3, 20.8±0.3, 21.5±0.3, 22.2±0.3, 22.9±0.3, 23.4±0.3, 24.0±0.3, 24.8±0.3, 25.2±0.3, 25.8±0.3, 27.5±0.3, 27.9±0.3, and 31.9±0.3.

In some embodiments, the crystalline form of the compound of formula (I) is characterized by a XRPD pattern that includes angle 2θ peaks (i.e., degrees 2θ) at about 4.6±0.2, 4.8±0.2, 15.3±0.2, 16.6±0.2, 18.1±0.2, and 22.9±0.2. The XRPD pattern of the crystalline form of the compound of formula (I) can further include angle 2θ peaks at about 7.3±0.2, 8.1±0.2, 9.7±0.2, 11.0±0.2, 12.2±0.2, 13.8±0.2, 14.8±0.2, 16.1±0.2, 17.5±0.2, 17.9±0.2, 18.5±0.2, 19.8±0.2, 20.2±0.2, 20.8±0.2, 21.5±0.2, 22.2±0.2, 23.4±0.2, 24.0±0.2, 24.8±0.2, 25.2±0.2, 25.8±0.2, 27.5±0.2, 27.9±0.2, and 31.9±0.2.

In some embodiments, the crystalline form of the compound of formula (I) is characterized by a XRPD pattern that includes angle 2θ peaks at about 4.6±0.2, 4.8±0.2, 7.3±0.2, 8.1±0.2, 9.7±0.2, 11.0±0.2, 12.2±0.2, 13.8±0.2, 14.8±0.2, 15.3±0.2, 16.1±0.2, 16.6±0.2, 17.5±0.2, 17.9±0.2, 18.1±0.2, 18.5±0.2, 19.8±0.2, 20.2±0.2, 20.8±0.2, 21.5±0.2, 22.2±0.2, 22.9±0.2, 23.4±0.2, 24.0±0.2, 24.8±0.2, 25.2±0.2, 25.8±0.2, 27.5±0.2, 27.9±0.2, and 31.9±0.2.

In some embodiments, the crystalline form of the compound of formula (I) is characterized by a XRPD pattern that includes angle 2θ peaks (i.e., degrees 2θ) at about 4.6±0.1, 4.8±0.1, 15.3±0.1, 16.6±0.1, 18.1±0.1, and 22.9±0.1. The XRPD pattern of the crystalline form of the compound of formula (I) can further include angle 2θ peaks at about 7.3±0.1, 8.1±0.1, 9.7±0.1, 11.0±0.1, 12.2±0.1, 13.8±0.1, 14.8±0.1, 16.1±0.1, 17.5±0.1, 17.9±0.1, 18.5±0.1, 19.8±0.1, 20.2±0.1, 20.8±0.1, 21.5±0.1, 22.2±0.1, 23.4±0.1, 24.0±0.1, 24.8±0.1, 25.2±0.1, 25.8±0.1, 27.5±0.1, 27.9±0.1, and 31.9±0.1.

In some embodiments, the crystalline form of the compound of formula (I) is characterized by a XRPD pattern that includes angle 2θ peaks at about 4.6±0.1, 4.8±0.1, 7.3±0.1, 8.1±0.1, 9.7±0.1, 11.0±0.1, 12.2±0.1, 13.8±0.1, 14.8±0.1, 15.3±0.1, 16.1±0.1, 16.6±0.1, 17.5±0.1, 17.9±0.1, 18.1±0.1, 18.5±0.1, 19.8±0.1, 20.2±0.1, 20.8±0.1, 21.5±0.1, 22.2±0.1, 22.9±0.1, 23.4±0.1, 24.0±0.1, 24.8±0.1, 25.2±0.1, 25.8±0.1, 27.5±0.1, 27.9±0.1, and 31.9±0.1.

In some embodiments, the crystalline form of the compound of formula (I) is characterized by a XRPD pattern that includes angle 2θ peaks (i.e., degrees 2θ) at about 4.6, 4.8, 15.3, 16.6, 18.1, and 22.9. The XRPD pattern of the crystalline form of the compound of formula (I) can further include angle 2θ peaks at about 7.3, 8.1, 9.7, 11.0, 12.2, 13.8, 14.8, 16.1, 17.5, 17.9, 18.5, 19.8, 20.2, 20.8, 21.5, 22.2, 23.4, 24.0, 24.8, 25.2, 25.8, 27.5, 27.9, and 31.9.

In some embodiments, the crystalline form of the compound of formula (I) is characterized by a XRPD pattern that includes angle 2θ peaks at about 4.6±0.2, 4.8±0.2, 7.3±0.2, 8.1±0.2, 9.7±0.2, 11.0±0.2, 12.2±0.2, 13.8±0.2, 14.8±0.2, 15.3±0.2, 16.1±0.2, 16.6±0.2, 17.5±0.2, 17.9±0.2, 18.1±0.2, 18.5±0.2, 19.8±0.2, 20.2±0.2, 20.8±0.2, 21.5±0.2, 22.2±0.2, 22.9±0.2, 23.4±0.2, 24.0±0.2, 24.8±0.2, 25.2±0.2, 25.8±0.2, 27.5±0.2, 27.9±0.2, and 31.9±0.2.

Figure 47:
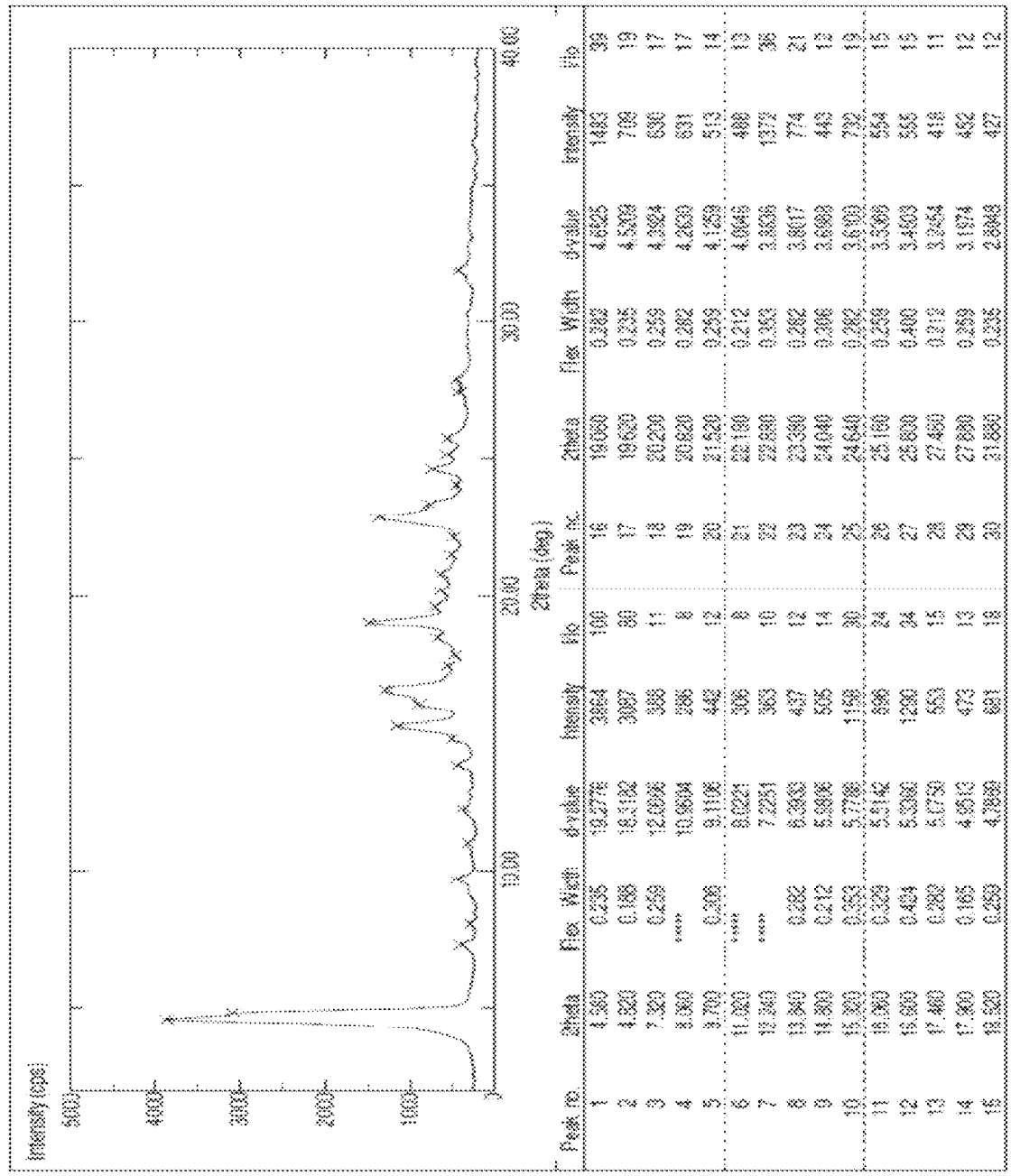
FIG. 47. Illustrates the XRPD of form F.

In certain embodiments, the crystalline form of the compound of formula (I) is characterized by a XRPD pattern corresponding substantially to FIG. 47.

In some embodiments, the crystalline form of the compound of formula (I) is characterized by a XRPD pattern that includes d spacings at about 19.27±0.3, 18.31±0.3, 5.77±0.3, 5.33±0.3, 4.65±0.3, and 3.88±0.3. The XRPD pattern of the crystalline form of the compound of formula (I) can be further characterized by d spacings at about 12.06±0.3, 10.96±0.3, 9.11±0.3, 8.02±0.3, 7.22±0.3, 6.39±0.3, 5.98±0.3, 5.51±0.3, 5.07±0.3, 4.95±0.3, 4.78±0.3, 4.52±0.3, 4.39±0.3, 4.26±0.3, 4.12±0.3, 4.00±0.3, 3.80±0.3, 3.69±0.3, 3.61±0.3, 3.53±0.3, 3.45±0.3, 3.24±0.3, 3.19±0.3, and 2.80±0.3.

In some embodiments, the crystalline form of the compound of formula (I) is characterized by a XRPD pattern that includes d spacings at about 19.27±0.3, 18.31±0.3, 12.06±0.3, 10.96±0.3, 9.11±0.3, 8.02±0.3, 7.22±0.3, 6.39±0.3, 5.98±0.3, 5.77±0.3, 5.51±0.3, 5.33±0.3, 5.07±0.3, 4.95±0.3, 4.78±0.3, 4.65±0.3, 4.52±0.3, 4.39±0.3, 4.26±0.3, 4.12±0.3, 4.00±0.3, 3.88±0.3, 3.80±0.3, 3.69±0.3, 3.61±0.3, 3.53±0.3, 3.45±0.3, 3.24±0.3, 3.19±0.3, and 2.80±0.3.

In some embodiments, the crystalline form of the compound of formula (I) is characterized by a XRPD pattern that includes d spacings at about 19.27±0.2, 18.31±0.2, 5.77±0.2, 5.33±0.2, 4.65±0.2, and 3.88±0.2. The XRPD pattern of the crystalline form of the compound of formula (I) can be further characterized by d spacings at about 12.06±0.2, 10.96±0.2, 9.11±0.2, 8.02±0.2, 7.22±0.2, 6.39±0.2, 5.98±0.2, 5.51±0.2, 5.07±0.2, 4.95±0.2, 4.78±0.2, 4.52±0.2, 4.39±0.2, 4.26±0.2, 4.12±0.2, 4.00±0.2, 3.80±0.2, 3.69±0.2, 3.61±0.2, 3.53±0.2, 3.45±0.2, 3.24±0.2, 3.19±0.2, and 2.80±0.2.

In some embodiments, the crystalline form of the compound of formula (I) is characterized by a XRPD pattern that includes d spacings at about 19.27±0.2, 18.31±0.2, 12.06±0.2, 10.96±0.2, 9.11±0.2, 8.02±0.2, 7.22±0.2, 6.39±0.2, 5.98±0.2, 5.77±0.2, 5.51±0.2, 5.33±0.2, 5.07±0.2, 4.95±0.2, 4.78±0.2, 4.65±0.2, 4.52±0.2, 4.39±0.2, 4.26±0.2, 4.12±0.2, 4.00±0.2, 3.88±0.2, 3.80±0.2, 3.69±0.2, 3.61±0.2, 3.53±0.2, 3.45±0.2, 3.24±0.2, 3.19±0.2, and 2.80±0.2.

In some embodiments, the crystalline form of the compound of formula (I) is characterized by a XRPD pattern that includes d spacings at about 19.27±0.1, 18.31±0.1, 5.77±0.1, 5.33±0.1, 4.65±0.1, and 3.88±0.1. The XRPD pattern of the crystalline form of the compound of formula (I) can be further characterized by d spacings at about 12.06±0.1, 10.96±0.1, 9.11±0.1, 8.02±0.1, 7.22±0.1, 6.39±0.1, 5.98±0.1, 5.51±0.1, 5.07±0.1, 4.95±0.1, 4.78±0.1, 4.52±0.1, 4.39±0.1, 4.26±0.1, 4.12±0.1, 4.00±0.1, 3.80±0.1, 3.69±0.1, 3.61±0.1, 3.53±0.1, 3.45±0.1, 3.24±0.1, 3.19±0.1, and 2.80±0.1.

In some embodiments, the crystalline form of the compound of formula (I) is characterized by a XRPD pattern that includes d spacings at about 19.27±0.1, 18.31±0.1, 12.06±0.1, 10.96±0.1, 9.11±0.1, 8.02±0.1, 7.22±0.1, 6.39±0.1, 5.98±0.1, 5.77±0.1, 5.51±0.1, 5.33±0.1, 5.07±0.1, 4.95±0.1, 4.78±0.1, 4.65±0.1, 4.52±0.1, 4.39±0.1, 4.26±0.1, 4.12±0.1, 4.00±0.1, 3.88±0.1, 3.80±0.1, 3.69±0.1, 3.61±0.1, 3.53±0.1, 3.45±0.1, 3.24±0.1, 3.19±0.1, and 2.80±0.1.

In some embodiments, the crystalline form of the compound of formula (I) is characterized by a XRPD pattern that includes d spacings at about 19.27, 18.31, 5.77, 5.33, 4.65, and 3.88. The XRPD pattern of the crystalline form of the compound of formula (I) can be further characterized by d spacings at about 12.06, 10.96, 9.11, 8.02, 7.22, 6.39, 5.98, 5.51, 5.07, 4.95, 4.78, 4.52, 4.39, 4.26, 4.12, 4.00, 3.80, 3.69, 3.61, 3.53, 3.45, 3.24, 3.19, and 2.80.

In some embodiments, the crystalline form of the compound of formula (I) is characterized by a XRPD pattern that includes d spacings at about 19.27, 18.31, 12.06, 10.96, 9.11, 8.02, 7.22, 6.39, 5.98, 5.77, 5.51, 5.33, 5.07, 4.95, 4.78, 4.65, 4.52, 4.39, 4.26, 4.12, 4.00, 3.88, 3.80, 3.69, 3.61, 3.53, 3.45, 3.24, 3.19, and 2.80.

The crystalline form of the compound of formula (I) can be Form F, where Form F is characterized by the XRPD pattern described above or by FIG. 47.

Figure 24:
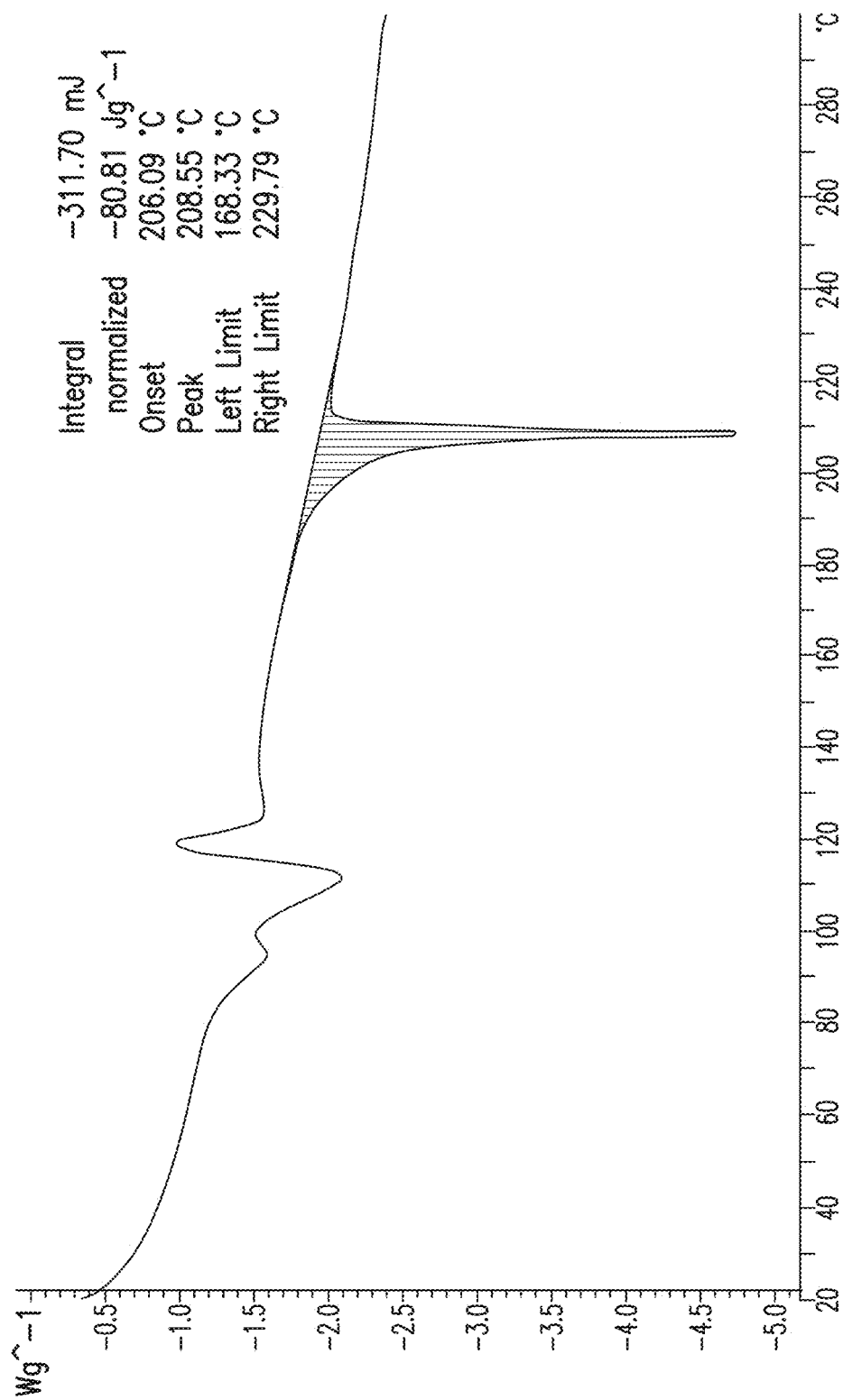
FIG. 24. Illustrates the DSC of form F (Table 1 experiment A1_6) with an endotherm/exotherm combination at about 100° C. (not integrated) and a melting endotherm at about 209° C. (peak).

The crystalline form of the compound of formula (I) (e.g., Form F) can include an endothermic event with an onset temperature of about 206° C. as determined by DSC. The crystalline form of the compound of formula (I) can be characterized by a DSC plot set forth in FIG. 24. The crystalline form of the compound of formula (I) can have a melting point of about 209° C. The crystalline form of the compound of formula (I) can be Form F, where Form F has a melting point of about 209° C.

The crystalline form of the compound of formula (I) (e.g., Form F) can have a mass loss of about 14% when heated from about 40° C. to about 170° C. Form F can be a solvated crystalline form, where Form F is a trifluoroethanol solvate.

In some embodiments, the crystalline form of the compound of formula (I) is characterized by a XRPD pattern that includes angle 2θ peaks (i.e., degrees 2θ) at about 12.0±0.3, 13.4±0.3, 15.7±0.3, 16.4±0.3, 18.4±0.3, 19.5±0.3, 21.5±0.3, 22.4±0.3, 22.8±0.3, 23.5±0.3, and 24.2±0.3. The XRPD pattern of the crystalline form of the compound of formula (I) can further include angle 2θ peaks at about 9.4±0.3, 10.2±0.3, 11.3±0.3, 12.9±0.3, 14.7±0.3, 17.1±0.3, 17.7±0.3, 19.0±0.3, 20.1±0.3, 20.5±0.3, 21.8±0.3, 25.1±0.3, 25.9±0.3, 26.2±0.3, 28.7±0.3, 27.2±0.3, 28.5±0.3, 29.3±0.3, and 33.8±0.3.

T In some embodiments, the crystalline form of the compound of formula (I) is characterized by a XRPD pattern that includes angle 2θ peaks at about 9.4±0.3, 10.2±0.3, 11.3±0.3, 12.0±0.3, 12.9±0.3, 13.4±0.3, 14.7±0.3, 15.7±0.3, 16.4±0.3, 17.1±0.3, 17.7±0.3, 18.4±0.3, 19.0±0.3, 19.5±0.3, 20.1±0.3, 20.5±0.3, 21.5±0.3, 21.8±0.3, 25.1±0.3, 22.4±0.3, 22.8±0.3, 23.5±0.3, 24.2±0.3, 25.9±0.3, 26.2±0.3, 28.7±0.3, 27.2±0.3, 28.5±0.3, 29.3±0.3, and 33.8±0.3.

In some embodiments, the crystalline form of the compound of formula (I) is characterized by a XRPD pattern that includes angle 2θ peaks (i.e., degrees 2θ) at about 12.0±0.2, 13.4±0.2, 15.7±0.2, 16.4±0.2, 18.4±0.2, 19.5±0.2, 21.5±0.2, 22.4±0.2, 22.8±0.2, 23.5±0.2, and 24.2±0.2. The XRPD pattern of the crystalline form of the compound of formula (I) can further include angle 2θ peaks at about 9.4±0.2, 10.2±0.2, 11.3±0.2, 12.9±0.2, 14.7±0.2, 17.1±0.2, 17.7±0.2, 19.0±0.2, 20.1±0.2, 20.5±0.2, 21.8±0.2, 25.1±0.2, 25.9±0.2, 26.2±0.2, 28.7±0.2, 27.2±0.2, 28.5±0.2, 29.3±0.2, and 33.8±0.2.

In some embodiments, the crystalline form of the compound of formula (I) is characterized by a XRPD pattern that includes angle 2θ peaks at about 9.4±0.2, 10.2±0.2, 11.3±0.2, 12.0±0.2, 12.9±0.2, 13.4±0.2, 14.7±0.2, 15.7±0.2, 16.4±0.2, 17.1±0.2, 17.7±0.2, 18.4±0.2, 19.0±0.2, 19.5±0.2, 20.1±0.2, 20.5±0.2, 21.5±0.2, 21.8±0.2, 25.1±0.2, 22.4±0.2, 22.8±0.2, 23.5±0.2, 24.2±0.2, 25.9±0.2, 26.2±0.2, 28.7±0.2, 27.2±0.2, 28.5±0.2, 29.3±0.2, and 33.8±0.2.

In some embodiments, the crystalline form of the compound of formula (I) is characterized by a XRPD pattern that includes angle 2θ peaks (i.e., degrees 2θ) at about 12.0±0.1, 13.4±0.1, 15.7±0.1, 16.4±0.1, 18.4±0.1, 19.5±0.1, 21.5±0.1, 22.4±0.1, 22.8±0.1, 23.5±0.1, and 24.2±0.1. The XRPD pattern of the crystalline form of the compound of formula (I) can further include angle 2θ peaks at about 9.4±0.1, 10.2±0.1, 11.3±0.1, 12.9±0.1, 14.7±0.1, 17.1±0.1, 17.7±0.1, 19.0±0.1, 20.1±0.1, 20.5±0.1, 21.8±0.1, 25.1±0.1, 25.9±0.1, 26.2±0.1, 28.7±0.1, 27.2±0.1, 28.5±0.1, 29.3±0.1, and 33.8±0.1.

In some embodiments, the crystalline form of the compound of formula (I) is characterized by a XRPD pattern that includes angle 2θ peaks at about 9.4±0.1, 10.2±0.1, 11.3±0.1, 12.0±0.1, 12.9±0.1, 13.4±0.1, 14.7±0.1, 15.7±0.1, 16.4±0.1, 17.1±0.1, 17.7±0.1, 18.4±0.1, 19.0±0.1, 19.5±0.1, 20.1±0.1, 20.5±0.1, 21.5±0.1, 21.8±0.1, 25.1±0.1, 22.4±0.1, 22.8±0.1, 23.5±0.1, 24.2±0.1, 25.9±0.1, 26.2±0.1, 28.7±0.1, 27.2±0.1, 28.5±0.1, 29.3±0.1, and 33.8±0.1.

In some embodiments, the crystalline form of the compound of formula (I) is characterized by a XRPD pattern that includes angle 2θ peaks (i.e., degrees 2θ) at about 12.0, 13.4, 15.7, 16.4, 18.4, 19.5, 21.5, 22.4, 22.8, 23.5, and 24.2. The XRPD pattern of the crystalline form of the compound of formula (I) can further include angle 2θ peaks at about 9.4, 10.2, 11.3, 12.9, 14.7, 17.1, 17.7, 19.0, 20.1, 20.5, 21.8, 25.1, 25.9, 26.2, 28.7, 27.2, 28.5, 29.3, and 33.8.

In some embodiments, the crystalline form of the compound of formula (I) is characterized by a XRPD pattern that includes angle 2θ peaks at about 9.4, 10.2, 11.3, 12.0, 12.9, 13.4, 14.7, 15.7, 16.4, 17.1, 17.7, 18.4, 19.0, 19.5, 20.1, 20.5, 21.5, 21.8, 25.1, 22.4, 22.8, 23.5, 24.2, 25.9, 26.2, 28.7, 27.2, 28.5, 29.3, and 33.8.

Figure 48:
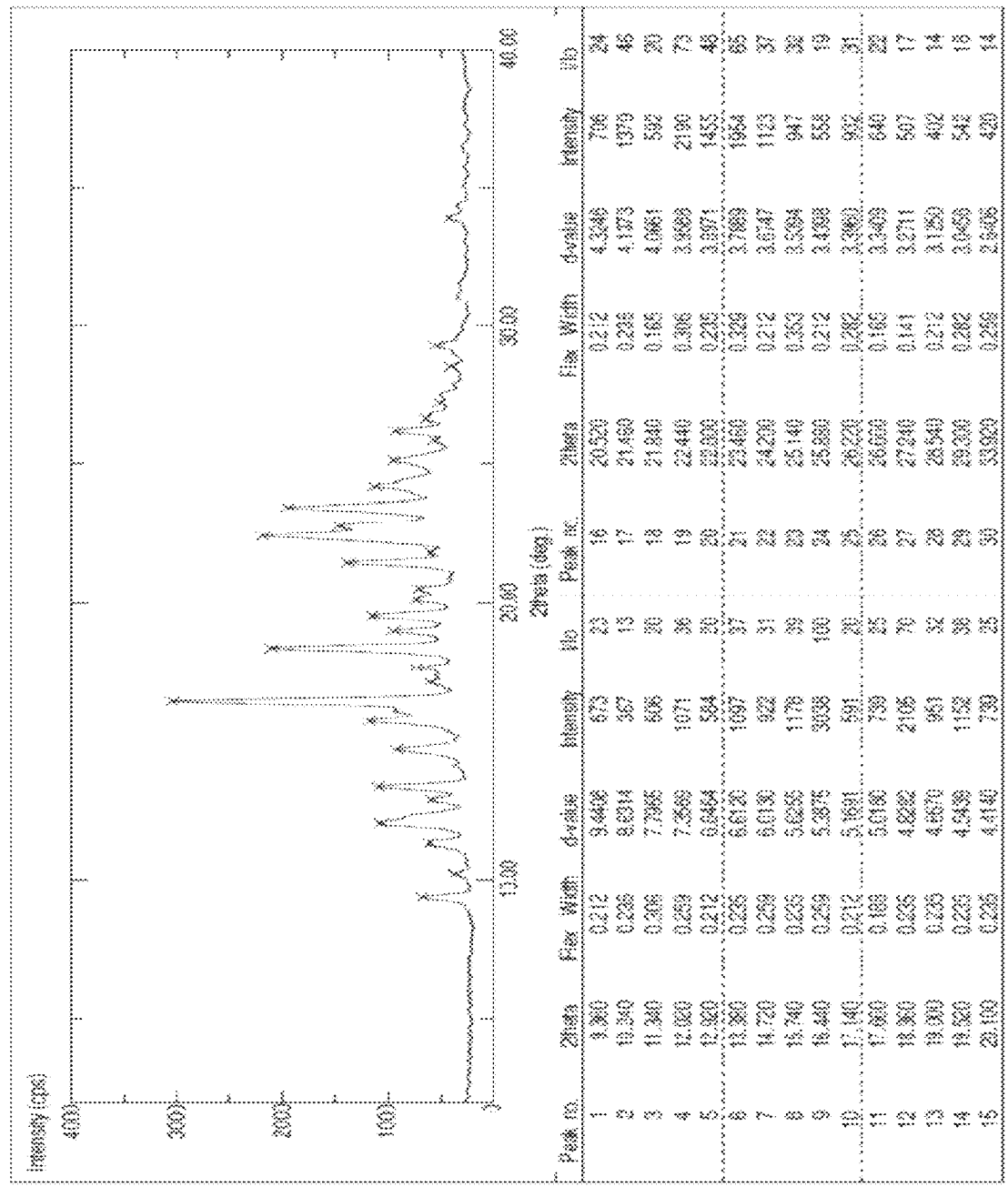
FIG. 48. Illustrates the XRPD of form G.

In certain embodiments, the crystalline form of the compound of formula (I) is characterized by a XRPD pattern corresponding substantially to FIG. 48.

In some embodiments, the crystalline form of the compound of formula (I) is characterized by a XRPD pattern that includes d spacings at about 7.35±0.3, 6.61±0.3, 5.62±0.3, 5.38±0.3, 4.82±0.3, 4.54±0.3, 4.13±0.3, 3.95±0.3, 3.89±0.3, 3.78±0.3, and 3.67±0.3. The XRPD pattern of the crystalline form of the compound of formula (I) can be further characterized by d spacings at about 9.44±0.3, 8.63±0.3, 7.79±0.3, 6.84±0.3, 6.01±0.3, 5.16±0.3, 5.01±0.3, 4.66±0.3, 4.41±0.3, 4.32±0.3, 4.06±0.3, 3.53±0.3, 3.43±0.3, 3.39±0.3, 3.34±0.3, 3.27±0.3, 3.12±0.3, 3.04±0.3, and 2.64±0.3.

In some embodiments, the crystalline form of the compound of formula (I) is characterized by a XRPD pattern that includes d spacings at about 9.44±0.3, 8.63±0.3, 7.79±0.3, 7.35±0.3, 6.84±0.3, 6.61±0.3, 6.01±0.3, 5.62±0.3, 5.38±0.3, 5.16±0.3, 5.01±0.3, 4.82±0.3, 4.66±0.3, 4.54±0.3, 4.41±0.3, 4.32±0.3, 4.13±0.3, 4.06±0.3, 3.95±0.3, 3.89±0.3, 3.78±0.3, 3.67±0.3, 3.53±0.3, 3.43±0.3, 3.39±0.3, 3.34±0.3, 3.27±0.3, 3.12±0.3, 3.04±0.3, and 2.64±0.3.

In some embodiments, the crystalline form of the compound of formula (I) is characterized by a XRPD pattern that includes d spacings at about 7.35±0.2, 6.61±0.2, 5.62±0.2, 5.38±0.2, 4.82±0.2, 4.54±0.2, 4.13±0.2, 3.95±0.2, 3.89±0.2, 3.78±0.2, and 3.67±0.2. The XRPD pattern of the crystalline form of the compound of formula (I) can be further characterized by d spacings at about 9.44±0.2, 8.63±0.2, 7.79±0.2, 6.84±0.2, 6.01±0.2, 5.16±0.2, 5.01±0.2, 4.66±0.2, 4.41±0.2, 4.32±0.2, 4.06±0.2, 3.53±0.2, 3.43±0.2, 3.39±0.2, 3.34±0.2, 3.27±0.2, 3.12±0.2, 3.04±0.2, and 2.64±0.2.

In some embodiments, the crystalline form of the compound of formula (I) is characterized by a XRPD pattern that includes d spacings at about 9.44±0.2, 8.63±0.2, 7.79±0.2, 7.35±0.2, 6.84±0.2, 6.61±0.2, 6.01±0.2, 5.62±0.2, 5.38±0.2, 5.16±0.2, 5.01±0.2, 4.82±0.2, 4.66±0.2, 4.54±0.2, 4.41±0.2, 4.32±0.2, 4.13±0.2, 4.06±0.2, 3.95±0.2, 3.89±0.2, 3.78±0.2, 3.67±0.2, 3.53±0.2, 3.43±0.2, 3.39±0.2, 3.34±0.2, 3.27±0.2, 3.12±0.2, 3.04±0.2, and 2.64±0.2.

In some embodiments, the crystalline form of the compound of formula (I) is characterized by a XRPD pattern that includes d spacings at about 7.35±0.1, 6.61±0.1, 5.62±0.1, 5.38±0.1, 4.82±0.1, 4.54±0.1, 4.13±0.1, 3.95±0.1, 3.89±0.1, 3.78±0.1, and 3.67±0.1. The XRPD pattern of the crystalline form of the compound of formula (I) can be further characterized by d spacings at about 9.44±0.1, 8.63±0.1, 7.79±0.1, 6.84±0.1, 6.01±0.1, 5.16±0.1, 5.01±0.1, 4.66±0.1, 4.41±0.1, 4.32±0.1, 4.06±0.1, 3.53±0.1, 3.43±0.1, 3.39±0.1, 3.34±0.1, 3.27±0.1, 3.12±0.1, 3.04±0.1, and 2.64±0.1.

In some embodiments, the crystalline form of the compound of formula (I) is characterized by a XRPD pattern that includes d spacings at about 9.44±0.1, 8.63±0.1, 7.79±0.1, 7.35±0.1, 6.84±0.1, 6.61±0.1, 6.01±0.1, 5.62±0.1, 5.38±0.1, 5.16±0.1, 5.01±0.1, 4.82±0.1, 4.66±0.1, 4.54±0.1, 4.41±0.1, 4.32±0.1, 4.13±0.1, 4.06±0.1, 3.95±0.1, 3.89±0.1, 3.78±0.1, 3.67±0.1, 3.53±0.1, 3.43±0.1, 3.39±0.1, 3.34±0.1, 3.27±0.1, 3.12±0.1, 3.04±0.1, and 2.64±0.1.

In some embodiments, the crystalline form of the compound of formula (I) is characterized by a XRPD pattern that includes d spacings at about 7.35, 6.61, 5.62, 5.38, 4.82, 4.54, 4.13, 3.95, 3.89, 3.78, and 3.67. The XRPD pattern of the crystalline form of the compound of formula (I) can be further characterized by d spacings at about 9.44, 8.63, 7.79, 6.84, 6.01, 5.16, 5.01, 4.66, 4.41, 4.32, 4.06, 3.53, 3.43, 3.39, 3.34, 3.27, 3.12, 3.04, and 2.64.

In some embodiments, the crystalline form of the compound of formula (I) is characterized by a XRPD pattern that includes d spacings at about 9.44, 8.63, 7.79, 7.35, 6.84, 6.61, 6.01, 5.62, 5.38, 5.16, 5.01, 4.82, 4.66, 4.54, 4.41, 4.32, 4.13, 4.06, 3.95, 3.89, 3.78, 3.67, 3.53, 3.43, 3.39, 3.34, 3.27, 3.12, 3.04, and 2.64.

The crystalline form of the compound of formula (I) can be Form G, where Form G is characterized by the XRPD pattern described above or by FIG. 48.

Figure 28:
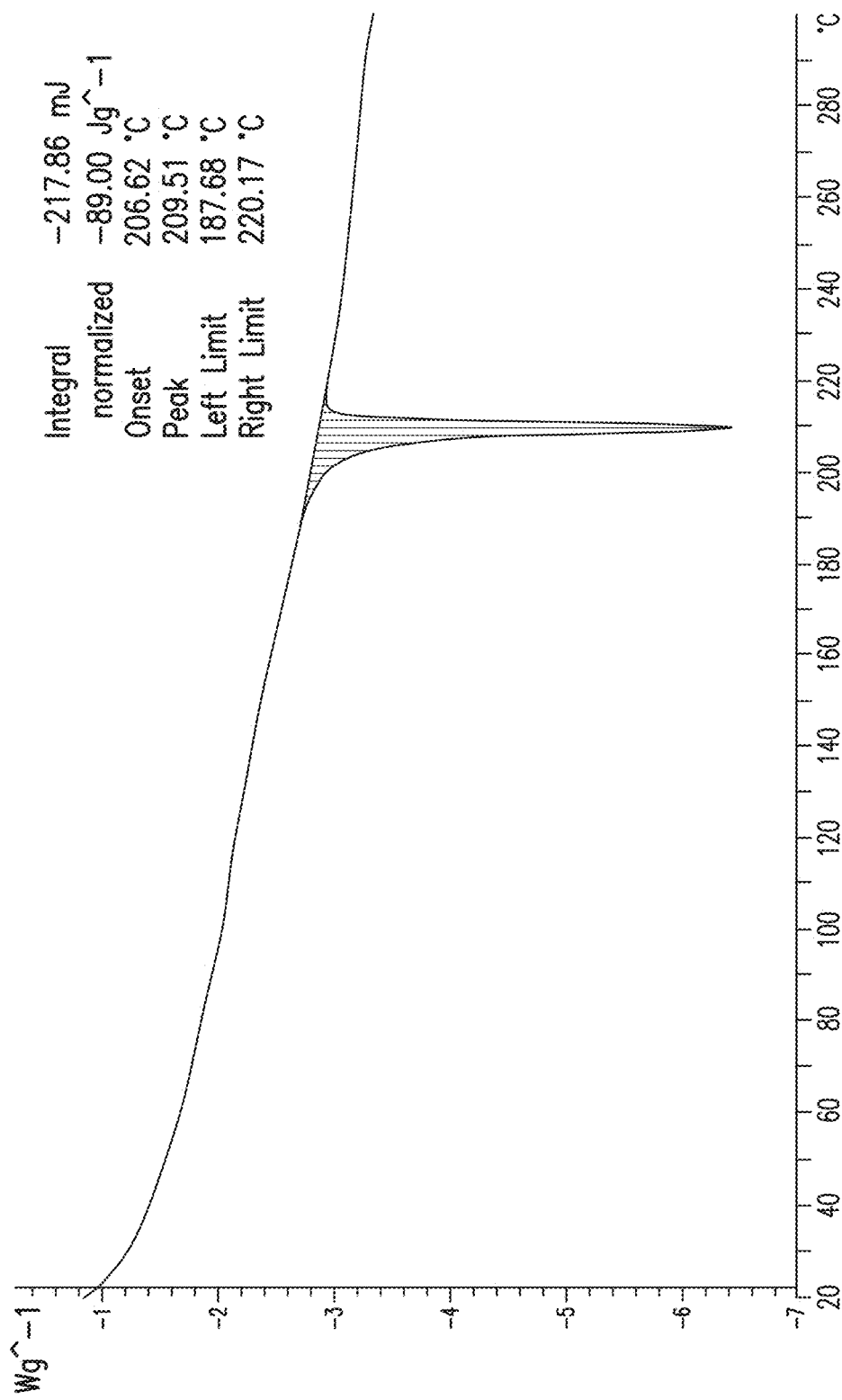
FIG. 28. Illustrates the DSC of form G (Table 1 experiment A2_1) with a melting endotherm at around 209.5° C. (peak).

The crystalline form of the compound of formula (I) (e.g., Form G) can include an endothermic event with an onset temperature of about 206° C. as determined by DSC. The crystalline form of the compound of formula (I) can be characterized by a DSC plot set forth in FIG. 28. The crystalline form of the compound of formula (I) can have a melting point of about 210° C. The crystalline form of the compound of formula (I) can be Form G, where Form G has a melting point of about 210° C.

The crystalline form of the compound of formula (I) (e.g., Form G) can have a mass loss of about 3.7% heated from about 25° C. to about 115° C.

In some embodiments, the crystalline form of the compound of formula (I) is characterized by a XRPD pattern that includes angle 2θ peaks (i.e., degrees 2θ) at about 11.0±0.3, 15.3±0.3, 15.6±0.3, 17.5±0.3, 18.9±0.3, 20.0±0.3, 21.1±0.3, 22.1±0.3, 24.6±0.3, 25.1±0.3, and 26.5±0.3. The XRPD pattern of the crystalline form of the compound of formula (I) can further include angle 2θ peaks at about 6.3±0.3, 12.7±0.3, 15.9±0.3, 18.2±0.3, 18.6±0.3, 22.6±0.3, 23.2±0.3, 24.2±0.3, 25.7±0.3, 27.0±0.3, 27.5±0.3, 29.5±0.3, 29.9±0.3, 30.5±0.3, 31.5±0.3, 32.2±0.3, 34.6±0.3, 35.1±0.3, and 35.6±0.3.

In some embodiments, the crystalline form of the compound of formula (I) is characterized by a XRPD pattern that includes angle 2θ peaks at about 6.3±0.3, 11.0±0.3, 12.7±0.3, 15.3±0.3, 15.6±0.3, 15.9±0.3, 17.5±0.3, 18.2±0.3, 18.6±0.3, 18.9±0.3, 20.0±0.3, 21.1±0.3, 22.1±0.3, 22.6±0.3, 23.2±0.3, 24.2±0.3, 24.6±0.3, 25.1±0.3, 25.7±0.3, 26.5±0.3, 27.0±0.3, 27.5±0.3, 29.5±0.3, 29.9±0.3, 30.5±0.3, 31.5±0.3, 32.2±0.3, 34.6±0.3, 35.1±0.3, and 35.6±0.3.

In some embodiments, the crystalline form of the compound of formula (I) is characterized by a XRPD pattern that includes angle 2θ peaks (i.e., degrees 2θ) at about 11.0±0.2, 15.3±0.2, 15.6±0.2, 17.5±0.2, 18.9±0.2, 20.0±0.2, 21.1±0.2, 22.1±0.2, 24.6±0.2, 25.1±0.2, and 26.5±0.2. The XRPD pattern of the crystalline form of the compound of formula (I) can further include angle 2θ peaks at about 6.3±0.2, 12.7±0.2, 15.9±0.2, 18.2±0.2, 18.6±0.2, 22.6±0.2, 23.2±0.2, 24.2±0.2, 25.7±0.2, 27.0±0.2, 27.5±0.2, 29.5±0.2, 29.9±0.2, 30.5±0.2, 31.5±0.2, 32.2±0.2, 34.6±0.2, 35.1±0.2, and 35.6±0.2.

In some embodiments, the crystalline form of the compound of formula (I) is characterized by a XRPD pattern that includes angle 2θ peaks at about 6.3±0.2, 11.0±0.2, 12.7±0.2, 15.3±0.2, 15.6±0.2, 15.9±0.2, 17.5±0.2, 18.2±0.2, 18.6±0.2, 18.9±0.2, 20.0±0.2, 21.1±0.2, 22.1±0.2, 22.6±0.2, 23.2±0.2, 24.2±0.2, 24.6±0.2, 25.1±0.2, 25.7±0.2, 26.5±0.2, 27.0±0.2, 27.5±0.2, 29.5±0.2, 29.9±0.2, 30.5±0.2, 31.5±0.2, 32.2±0.2, 34.6±0.2, 35.1±0.2, and 35.6±0.2.

In some embodiments, the crystalline form of the compound of formula (I) is characterized by a XRPD pattern that includes angle 2θ peaks (i.e., degrees 2θ) at about 11.0±0.1, 15.3±0.1, 15.6±0.1, 17.5±0.1, 18.9±0.1, 20.0±0.1, 21.1±0.1, 22.1±0.1, 24.6±0.1, 25.1±0.1, and 26.5±0.1. The XRPD pattern of the crystalline form of the compound of formula (I) can further include angle 2θ peaks at about 6.3±0.1, 12.7±0.1, 15.9±0.1, 18.2±0.1, 18.6±0.1, 22.6±0.1, 23.2±0.1, 24.2±0.1, 25.7±0.1, 27.0±0.1, 27.5±0.1, 29.5±0.1, 29.9±0.1, 30.5±0.1, 31.5±0.1, 32.2±0.1, 34.6±0.1, 35.1±0.1, and 35.6±0.1.

In some embodiments, the crystalline form of the compound of formula (I) is characterized by a XRPD pattern that includes angle 2θ peaks at about 6.3±0.1, 11.0±0.1, 12.7±0.1, 15.3±0.1, 15.6±0.1, 15.9±0.1, 17.5±0.1, 18.2±0.1, 18.6±0.1, 18.9±0.1, 20.0±0.1, 21.1±0.1, 22.1±0.1, 22.6±0.1, 23.2±0.1, 24.2±0.1, 24.6±0.1, 25.1±0.1, 25.7±0.1, 26.5±0.1, 27.0±0.1, 27.5±0.1, 29.5±0.1, 29.9±0.1, 30.5±0.1, 31.5±0.1, 32.2±0.1, 34.6±0.1, 35.1±0.1, and 35.6±0.1.

In some embodiments, the crystalline form of the compound of formula (I) is characterized by a XRPD pattern that includes angle 2θ peaks (i.e., degrees 2θ) at about 11.0, 15.3, 15.6, 17.5, 18.9, 20.0, 21.1, 22.1, 24.6, 25.1, and 26.5. The XRPD pattern of the crystalline form of the compound of formula (I) can further include angle 2θ peaks at about 6.3, 12.7, 15.9, 18.2, 18.6, 22.6, 23.2, 24.2, 25.7, 27.0, 27.5, 29.5, 29.9, 30.5, 31.5, 32.2, 34.6, 35.1, and 35.6.

In some embodiments, the crystalline form of the compound of formula (I) is characterized by a XRPD pattern that includes angle 2θ peaks at about 6.3, 11.0, 12.7, 15.3, 15.6, 15.9, 17.5, 18.2, 18.6, 18.9, 20.0, 21.1, 22.1, 22.6, 23.2, 24.2, 24.6, 25.1, 25.7, 26.5, 27.0, 27.5, 29.5, 29.9, 30.5, 31.5, 32.2, 34.6, 35.1, and 35.6.

Figure 49:
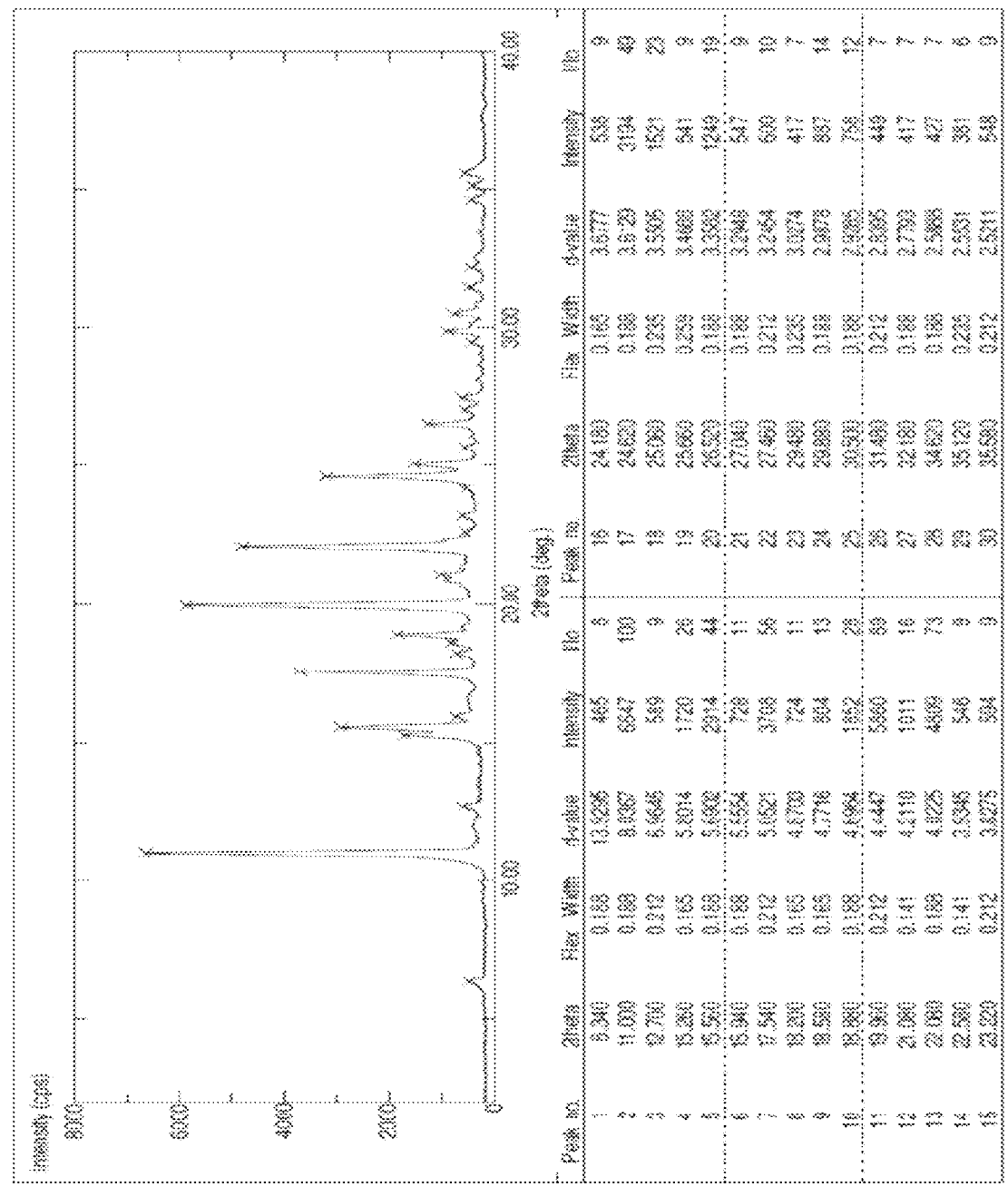
FIG. 49. Illustrates the XRPD of form H.

In certain embodiments, the crystalline form of the compound of formula (I) is characterized by a XRPD pattern corresponding substantially to FIG. 49.

In some embodiments, the crystalline form of the compound of formula (I) is characterized by a XRPD pattern that includes d spacings at about 8.03±0.3, 5.80±0.3, 5.69±0.3, 5.05±0.3, 4.69±0.3, 4.44±0.3, 4.21±0.3, 4.02±0.3, 3.61±0.3, 3.55±0.3, and 3.35±0.3. The XRPD pattern of the crystalline form of the compound of formula (I) can be further characterized by d spacings at about 13.92±0.3, 6.96±0.3, 5.55±0.3, 4.87±0.3, 4.77±0.3, 3.93±0.3, 3.82±0.3, 3.67±0.3, 3.46±0.3, 3.29±0.3, 3.24±0.3, 3.02±0.3, 2.98±0.3, 2.92±0.3, 2.83±0.3, 2.77±0.3, 2.58±0.3, 2.55±0.3, and 2.52±0.3.

In some embodiments, the crystalline form of the compound of formula (I) is characterized by a XRPD pattern that includes d spacings at about 13.92±0.3, 8.03±0.3, 6.96±0.3, 5.80±0.3, 5.69±0.3, 5.55±0.3, 5.05±0.3, 4.87±0.3, 4.77±0.3, 4.69±0.3, 4.44±0.3, 4.21±0.3, 4.02±0.3, 3.93±0.3, 3.82±0.3, 3.67±0.3, 3.61±0.3, 3.55±0.3, 3.46±0.3, 3.35±0.3, 3.29±0.3, 3.24±0.3, 3.02±0.3, 2.98±0.3, 2.92±0.3, 2.83±0.3, 2.77±0.3, 2.58±0.3, 2.55±0.3, and 2.52±0.3.

In some embodiments, the crystalline form of the compound of formula (I) is characterized by a XRPD pattern that includes d spacings at about 8.03±0.2, 5.80±0.2, 5.69±0.2, 5.05±0.2, 4.69±0.2, 4.44±0.2, 4.21±0.2, 4.02±0.2, 3.61±0.2, 3.55±0.2, and 3.35±0.2. The XRPD pattern of the crystalline form of the compound of formula (I) can be further characterized by d spacings at about 13.92±0.2, 6.96±0.2, 5.55±0.2, 4.87±0.2, 4.77±0.2, 3.93±0.2, 3.82±0.2, 3.67±0.2, 3.46±0.2, 3.29±0.2, 3.24±0.2, 3.02±0.2, 2.98±0.2, 2.92±0.2, 2.83±0.2, 2.77±0.2, 2.58±0.2, 2.55±0.2, and 2.52±0.2.

In some embodiments, the crystalline form of the compound of formula (I) is characterized by a XRPD pattern that includes d spacings at about 13.92±0.2, 8.03±0.2, 6.96±0.2, 5.80±0.2, 5.69±0.2, 5.55±0.2, 5.05±0.2, 4.87±0.2, 4.77±0.2, 4.69±0.2, 4.44±0.2, 4.21±0.2, 4.02±0.2, 3.93±0.2, 3.82±0.2, 3.67±0.2, 3.61±0.2, 3.55±0.2, 3.46±0.2, 3.35±0.2, 3.29±0.2, 3.24±0.2, 3.02±0.2, 2.98±0.2, 2.92±0.2, 2.83±0.2, 2.77±0.2, 2.58±0.2, 2.55±0.2, and 2.52±0.2.

In some embodiments, the crystalline form of the compound of formula (I) is characterized by a XRPD pattern that includes d spacings at about 8.03±0.1, 5.80±0.1, 5.69±0.1, 5.05±0.1, 4.69±0.1, 4.44±0.1, 4.21±0.1, 4.02±0.1, 3.61±0.1, 3.55±0.1, and 3.35±0.1. The XRPD pattern of the crystalline form of the compound of formula (I) can be further characterized by d spacings at about 13.92±0.1, 6.96±0.1, 5.55±0.1, 4.87±0.1, 4.77±0.1, 3.93±0.1, 3.82±0.1, 3.67±0.1, 3.46±0.1, 3.29±0.1, 3.24±0.1, 3.02±0.1, 2.98±0.1, 2.92±0.1, 2.83±0.1, 2.77±0.1, 2.58±0.1, 2.55±0.1, and 2.52±0.1.

In some embodiments, the crystalline form of the compound of formula (I) is characterized by a XRPD pattern that includes d spacings at about 13.92±0.1, 8.03±0.1, 6.96±0.1, 5.80±0.1, 5.69±0.1, 5.55±0.1, 5.05±0.1, 4.87±0.1, 4.77±0.1, 4.69±0.1, 4.44±0.1, 4.21±0.1, 4.02±0.1, 3.93±0.1, 3.82±0.1, 3.67±0.1, 3.61±0.1, 3.55±0.1, 3.46±0.1, 3.35±0.1, 3.29±0.1, 3.24±0.1, 3.02±0.1, 2.98±0.1, 2.92±0.1, 2.83±0.1, 2.77±0.1, 2.58±0.1, 2.55±0.1, and 2.52±0.1.

In some embodiments, the crystalline form of the compound of formula (I) is characterized by a XRPD pattern that includes d spacings at about 8.03, 5.80, 5.69, 5.05, 4.69, 4.44, 4.21, 4.02, 3.61, 3.55, and 3.35. The XRPD pattern of the crystalline form of the compound of formula (I) can be further characterized by d spacings at about 13.92, 6.96, 5.55, 4.87, 4.77, 3.93, 3.82, 3.67, 3.46, 3.29, 3.24, 3.02, 2.98, 2.92, 2.83, 2.77, 2.58, 2.55, and 2.52.

In some embodiments, the crystalline form of the compound of formula (I) is characterized by a XRPD pattern that includes d spacings at about 13.92, 8.03, 6.96, 5.80, 5.69, 5.55, 5.05, 4.87, 4.77, 4.69, 4.44, 4.21, 4.02, 3.93, 3.82, 3.67, 3.61, 3.55, 3.46, 3.35, 3.29, 3.24, 3.02, 2.98, 2.92, 2.83, 2.77, 2.58, 2.55, and 2.52.

The crystalline form of the compound of formula (I) can be Form H, where Form H is characterized by the XRPD pattern described above or by FIG. 49.

In some embodiments, the crystalline form of the compound of formula (I) is characterized by a XRPD pattern that includes angle 2θ peaks (i.e., degrees 2θ) at about 12.3±0.3, 14.8±0.3, 16.4±0.3, 18.5±0.3, 19.3±0.3, 19.6±0.3, 20.3±0.3, 21.1±0.3, 22.1±0.3, 22.5±0.3, 23.2±0.3, 24.1±0.3, 25.4±0.3, and 28.2±0.3. The XRPD pattern of the crystalline form of the compound of formula (I) can further include angle 2θ peaks at about 4.6±0.3, 8.7±0.3, 8.3±0.3, 9.1±0.3, 10.3±0.3, 11.0±0.3, 13.5±0.3, 14.0±0.3, 15.4±0.3, 17.1±0.3, 24.8±0.3, 27.2±0.3, 27.7±0.3, 29.4±0.3, 30.2±0.3, and 37.2±0.3.

In some embodiments, the crystalline form of the compound of formula (I) is characterized by a XRPD pattern that includes angle 2θ peaks at about 4.6±0.3, 8.7±0.3, 8.3±0.3, 9.1±0.3, 10.3±0.3, 11.0±0.3, 12.3±0.3, 13.5±0.3, 14.0±0.3, 14.8±0.3, 15.4±0.3, 16.4±0.3, 17.1±0.3, 18.5±0.3, 19.3±0.3, 19.6±0.3, 20.3±0.3, 21.1±0.3, 22.1±0.3, 22.5±0.3, 23.2±0.3, 24.1±0.3, 24.8±0.3, 25.4±0.3, 27.2±0.3, 27.7±0.3, 28.2±0.3, 29.4±0.3, 30.2±0.3, and 37.2±0.3.

In some embodiments, the crystalline form of the compound of formula (I) is characterized by a XRPD pattern that includes angle 2θ peaks (i.e., degrees 2θ) at about 12.3±0.2, 14.8±0.2, 16.4±0.2, 18.5±0.2, 19.3±0.2, 19.6±0.2, 20.3±0.2, 21.1±0.2, 22.1±0.2, 22.5±0.2, 23.2±0.2, 24.1±0.2, 25.4±0.2, and 28.2±0.2. The XRPD pattern of the crystalline form of the compound of formula (I) can further include angle 2θ peaks at about 4.6±0.2, 8.7±0.2, 8.3±0.2, 9.1±0.2, 10.3±0.2, 11.0±0.2, 13.5±0.2, 14.0±0.2, 15.4±0.2, 17.1±0.2, 24.8±0.2, 27.2±0.2, 27.7±0.2, 29.4±0.2, 30.2±0.2, and 37.2±0.2.

In some embodiments, the crystalline form of the compound of formula (I) is characterized by a XRPD pattern that includes angle 2θ peaks at about 4.6±0.2, 8.7±0.2, 8.3±0.2, 9.1±0.2, 10.3±0.2, 11.0±0.2, 12.3±0.2, 13.5±0.2, 14.0±0.2, 14.8±0.2, 15.4±0.2, 16.4±0.2, 17.1±0.2, 18.5±0.2, 19.3±0.2, 19.6±0.2, 20.3±0.2, 21.1±0.2, 22.1±0.2, 22.5±0.2, 23.2±0.2, 24.1±0.2, 24.8±0.2, 25.4±0.2, 27.2±0.2, 27.7±0.2, 28.2±0.2, 29.4±0.2, 30.2±0.2, and 37.2±0.2.

In some embodiments, the crystalline form of the compound of formula (I) is characterized by a XRPD pattern that includes angle 2θ peaks (i.e., degrees 2θ) at about 12.3±0.1, 14.8±0.1, 16.4±0.1, 18.5±0.1, 19.3±0.1, 19.6±0.1, 20.3±0.1, 21.1±0.1, 22.1±0.1, 22.5±0.1, 23.2±0.1, 24.1±0.1, 25.4±0.1, and 28.2±0.1. The XRPD pattern of the crystalline form of the compound of formula (I) can further include angle 2θ peaks at about 4.6±0.1, 8.7±0.1, 8.3±0.1, 9.1±0.1, 10.3±0.1, 11.0±0.1, 13.5±0.1, 14.0±0.1, 15.4±0.1, 17.1±0.1, 24.8±0.1, 27.2±0.1, 27.7±0.1, 29.4±0.1, 30.2±0.1, and 37.2±0.1.

In some embodiments, the crystalline form of the compound of formula (I) is characterized by a XRPD pattern that includes angle 2θ peaks at about 4.6±0.1, 8.7±0.1, 8.3±0.1, 9.1±0.1, 10.3±0.1, 11.0±0.1, 12.3±0.1, 13.5±0.1, 14.0±0.1, 14.8±0.1, 15.4±0.1, 16.4±0.1, 17.1±0.1, 18.5±0.1, 19.3±0.1, 19.6±0.1, 20.3±0.1, 21.1±0.1, 22.1±0.1, 22.5±0.1, 23.2±0.1, 24.1±0.1, 24.8±0.1, 25.4±0.1, 27.2±0.1, 27.7±0.1, 28.2±0.1, 29.4±0.1, 30.2±0.1, and 37.2±0.1.

In some embodiments, the crystalline form of the compound of formula (I) is characterized by a XRPD pattern that includes angle 2θ peaks (i.e., degrees 2θ) at about 12.3, 14.8, 16.4, 18.5, 19.3, 19.6, 20.3, 21.1, 22.1, 22.5, 23.2, 24.1, 25.4, and 28.2. The XRPD pattern of the crystalline form of the compound of formula (I) can further include angle 2θ peaks at about 4.6, 8.7, 8.3, 9.1, 10.3, 11.0, 13.5, 14.0, 15.4, 17.1, 24.8, 27.2, 27.7, 29.4, 30.2, and 37.2.

In some embodiments, the crystalline form of the compound of formula (I) is characterized by a XRPD pattern that includes angle 2θ peaks at about 4.6, 8.7, 8.3, 9.1, 10.3, 11.0, 12.3, 13.5, 14.0, 14.8, 15.4, 16.4, 17.1, 18.5, 19.3, 19.6, 20.3, 21.1, 22.1, 22.5, 23.2, 24.1, 24.8, 25.4, 27.2, 27.7, 28.2, 29.4, 30.2, and 37.2.

Figure 50:
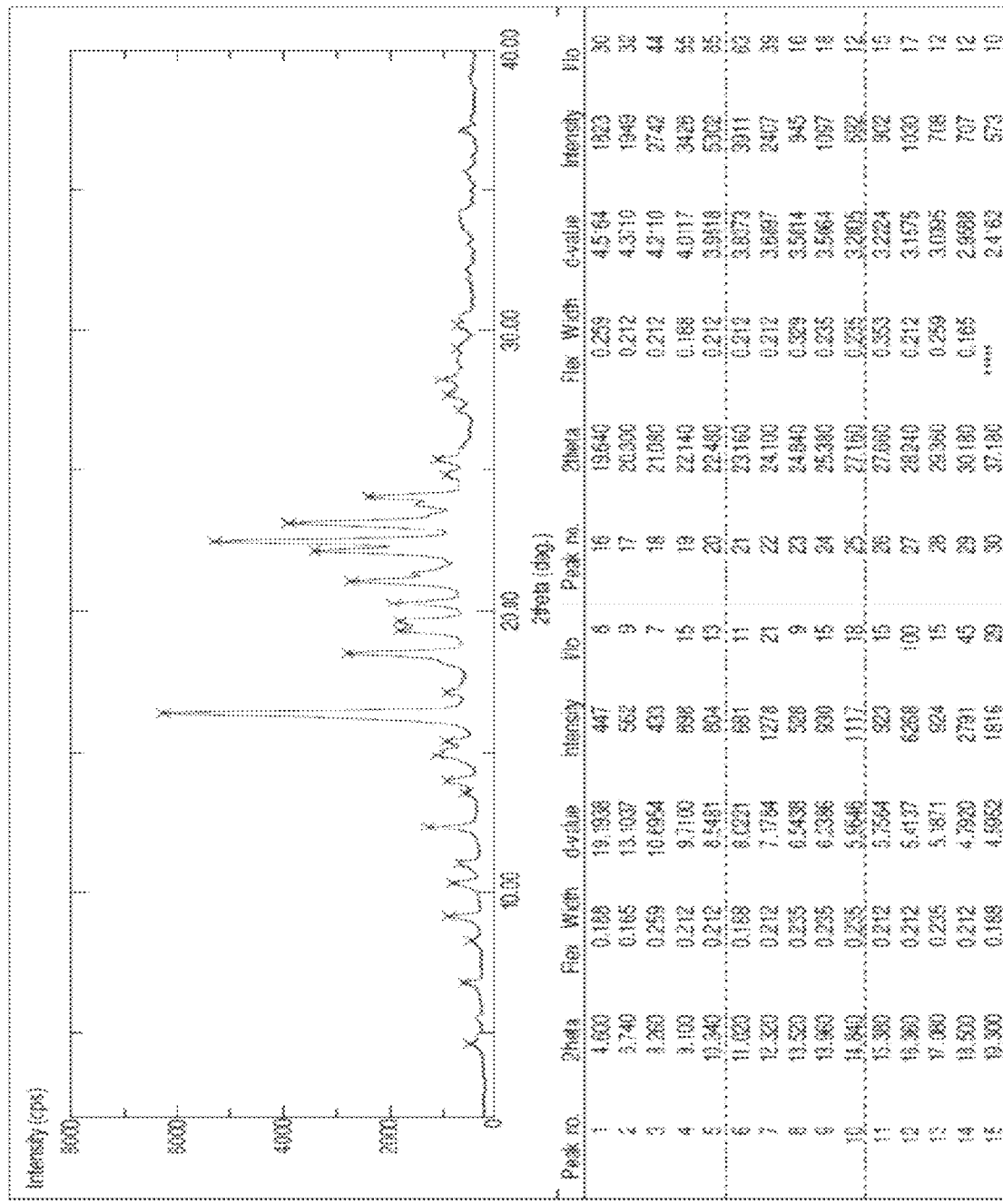
FIG. 50. Illustrates the XRPD of form I.

In certain embodiments, the crystalline form of the compound of formula (I) is characterized by a XRPD pattern corresponding substantially to FIG. 50.

In some embodiments, the crystalline form of the compound of formula (I) is characterized by a XRPD pattern that includes d spacings at about 7.17±0.3, 5.96±0.3, 5.41±0.3, 4.79±0.3, 4.59±0.3, 4.51±0.3, 4.37±0.3, 4.21±0.3, 4.01±0.3, 3.95±0.3, 3.83±0.3, 3.68±0.3, 3.50±0.3, and 3.15±0.3. The XRPD pattern of the crystalline form of the compound of formula (I) can be further characterized by d spacings at about 19.19±0.3, 13.10±0.3, 10.69±0.3, 9.71±0.3, 8.54±0.3, 8.02±0.3, 6.54±0.3, 6.33±0.3, 5.75±0.3, 5.18±0.3, 3.58±0.3, 3.28±0.3, 3.22±0.3, 3.03±0.3, 2.95±0.3, and 2.41±0.3.

In some embodiments, the crystalline form of the compound of formula (I) is characterized by a XRPD pattern that includes d spacings at about 19.19±0.3, 13.10±0.3, 10.69±0.3, 9.71±0.3, 8.54±0.3, 8.02±0.3, 7.17±0.3, 6.54±0.3, 6.33±0.3, 5.96±0.3, 5.75±0.3, 5.41±0.3, 5.18±0.3, 4.79±0.3, 4.59±0.3, 4.51±0.3, 4.37±0.3, 4.21±0.3, 4.01±0.3, 3.95±0.3, 3.83±0.3, 3.68±0.3, 3.58±0.3, 3.50±0.3, 3.28±0.3, 3.22±0.3, 3.15±0.3, 3.03±0.3, 2.95±0.3, and 2.41±0.3.

In some embodiments, the crystalline form of the compound of formula (I) is characterized by a XRPD pattern that includes d spacings at about 7.17±0.2, 5.96±0.2, 5.41±0.2, 4.79±0.2, 4.59±0.2, 4.51±0.2, 4.37±0.2, 4.21±0.2, 4.01±0.2, 3.95±0.2, 3.83±0.2, 3.68±0.2, 3.50±0.2, and 3.15±0.2. The XRPD pattern of the crystalline form of the compound of formula (I) can be further characterized by d spacings at about 19.19±0.2, 13.10±0.2, 10.69±0.2, 9.71±0.2, 8.54±0.2, 8.02±0.2, 6.54±0.2, 6.33±0.2, 5.75±0.2, 5.18±0.2, 3.58±0.2, 3.28±0.2, 3.22±0.2, 3.03±0.2, 2.95±0.2, and 2.41±0.2.

In some embodiments, the crystalline form of the compound of formula (I) is characterized by a XRPD pattern that includes d spacings at about 19.19±0.2, 13.10±0.2, 10.69±0.2, 9.71±0.2, 8.54±0.2, 8.02±0.2, 7.17±0.2, 6.54±0.2, 6.33±0.2, 5.96±0.2, 5.75±0.2, 5.41±0.2, 5.18±0.2, 4.79±0.2, 4.59±0.2, 4.51±0.2, 4.37±0.2, 4.21±0.2, 4.01±0.2, 3.95±0.2, 3.83±0.2, 3.68±0.2, 3.58±0.2, 3.50±0.2, 3.28±0.2, 3.22±0.2, 3.15±0.2, 3.03±0.2, 2.95±0.2, 2.41±0.2.

In some embodiments, the crystalline form of the compound of formula (I) is characterized by a XRPD pattern that includes d spacings at about 7.17±0.1, 5.96±0.1, 5.41±0.1, 4.79±0.1, 4.59±0.1, 4.51±0.1, 4.37±0.1, 4.21±0.1, 4.01±0.1, 3.95±0.1, 3.83±0.1, 3.68±0.1, 3.50±0.1, and 3.15±0.1. The XRPD pattern of the crystalline form of the compound of formula (I) can be further characterized by d spacings at about 19.19±0.1, 13.10±0.1, 10.69±0.1, 9.71±0.1, 8.54±0.1, 8.02±0.1, 6.54±0.1, 6.33±0.1, 5.75±0.1, 5.18±0.1, 3.58±0.1, 3.28±0.1, 3.22±0.1, 3.03±0.1, 2.95±0.1, and 2.41±0.1.

In some embodiments, the crystalline form of the compound of formula (I) is characterized by a XRPD pattern that includes d spacings at about 19.19±0.1, 13.10±0.1, 10.69±0.1, 9.71±0.1, 8.54±0.1, 8.02±0.1, 7.17±0.1, 6.54±0.1, 6.33±0.1, 5.96±0.1, 5.75±0.1, 5.41±0.1, 5.18±0.1, 4.79±0.1, 4.59±0.1, 4.51±0.1, 4.37±0.1, 4.21±0.1, 4.01±0.1, 3.95±0.1, 3.83±0.1, 3.68±0.1, 3.58±0.1, 3.50±0.1, 3.28±0.1, 3.22±0.1, 3.15±0.1, 3.03±0.1, 2.95±0.1, 2.41±0.1.

In some embodiments, the crystalline form of the compound of formula (I) is characterized by a XRPD pattern that includes d spacings at about 7.17, 5.96, 5.41, 4.79, 4.59, 4.51, 4.37, 4.21, 4.01, 3.95, 3.83, 3.68, 3.50, and 3.15. The XRPD pattern of the crystalline form of the compound of formula (I) can be further characterized by d spacings at about 19.19, 13.10, 10.69, 9.71, 8.54, 8.02, 6.54, 6.33, 5.75, 5.18, 3.58, 3.28, 3.22, 3.03, 2.95, and 2.41.

In some embodiments, the crystalline form of the compound of formula (I) is characterized by a XRPD pattern that includes d spacings at about 19.19, 13.10, 10.69, 9.71, 8.54, 8.02, 7.17, 6.54, 6.33, 5.96, 5.75, 5.41, 5.18, 4.79, 4.59, 4.51, 4.37, 4.21, 4.01, 3.95, 3.83, 3.68, 3.58, 3.50, 3.28, 3.22, 3.15, 3.03, 2.95, 2.41.

The crystalline form of the compound of formula (I) can be Form I, where Form I is characterized by the XRPD pattern described above or by FIG. 50.

The crystalline form of the compound of formula (I) (e.g., Form I) can include an endothermic event with an onset temperature of about 110° C. as determined by DSC. The crystalline form of the compound of formula (I) (e.g., Form I) can be characterized by a DSC plot set forth in FIG. 34.

The crystalline form of the compound of formula (I) (e.g., Form I) can have a mass loss of 20% when heated from about 25° C. to about 180° C. Form I can be a solvated crystalline form, where Form I is a trifluoroethanol solvate.

Figure 36:
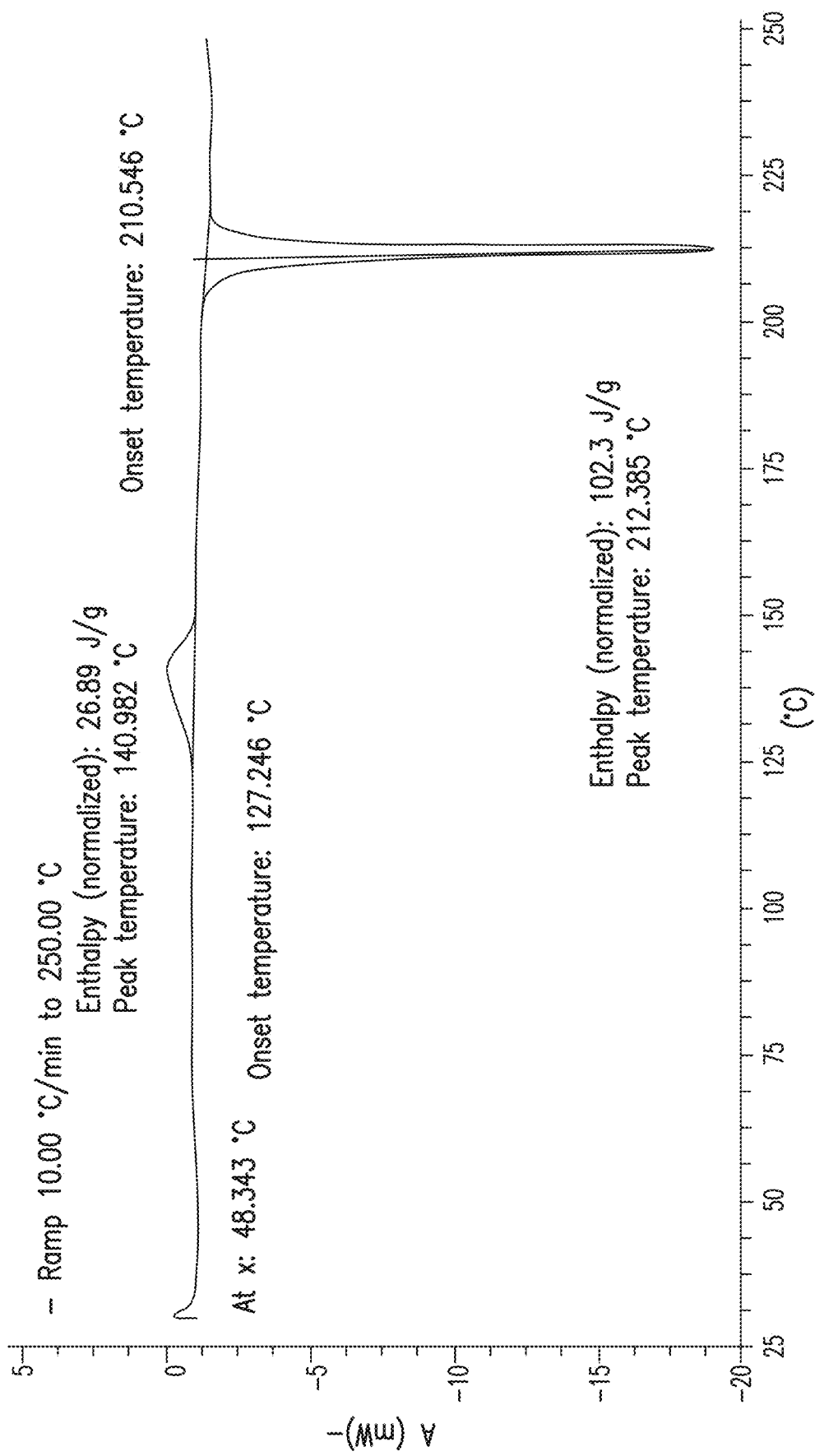
FIG. 36. Illustrates the DSC of form J. An exotherm form conversion around 130° C. and a melting point at 212° C. (peak) which likely represents form G.

The crystalline form of the compound of formula (I) (e.g., Form J) can include an exothermic event with an onset temperature of about 130° C. as determined by DSC. The crystalline form of the compound of formula (I) (e.g., Form I) can be characterized by a DSC plot set forth in FIG. 36.

The crystalline form of the compound of formula (I) can have a loss of about 19.8% when heated from about 25° C. to about 180° C. The crystalline form of the compound of formula (I) can be Form J, where Form J has a loss of about 19.8% when heated from about 25° C. to about 180° C.

Figure 35:
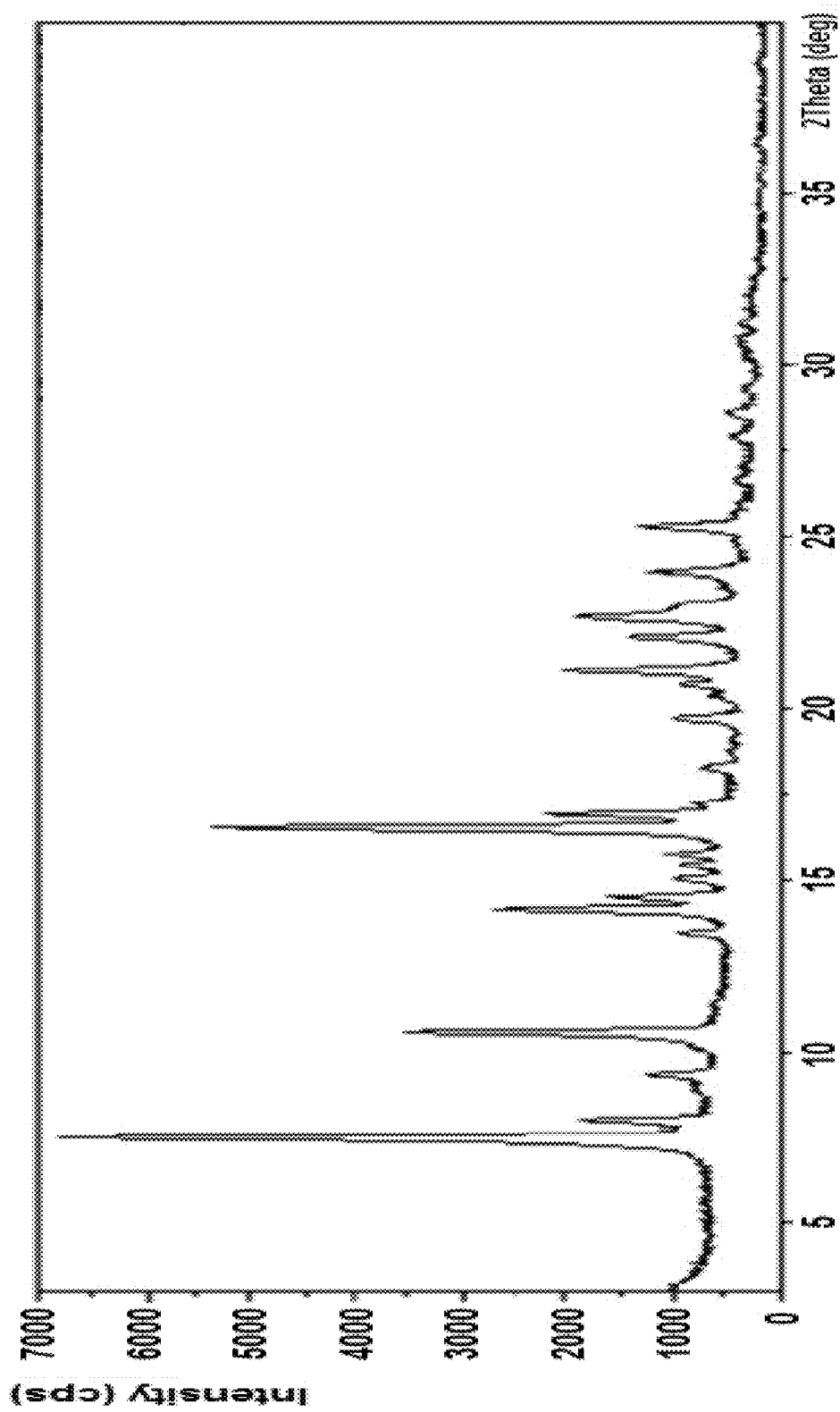
FIG. 35. Illustrates the XRPD of form J.

The crystalline form of the compound of formula (I) can be Form J, where Form J is characterized by the XRPD pattern described above or by FIG. 35.

Figure 37:
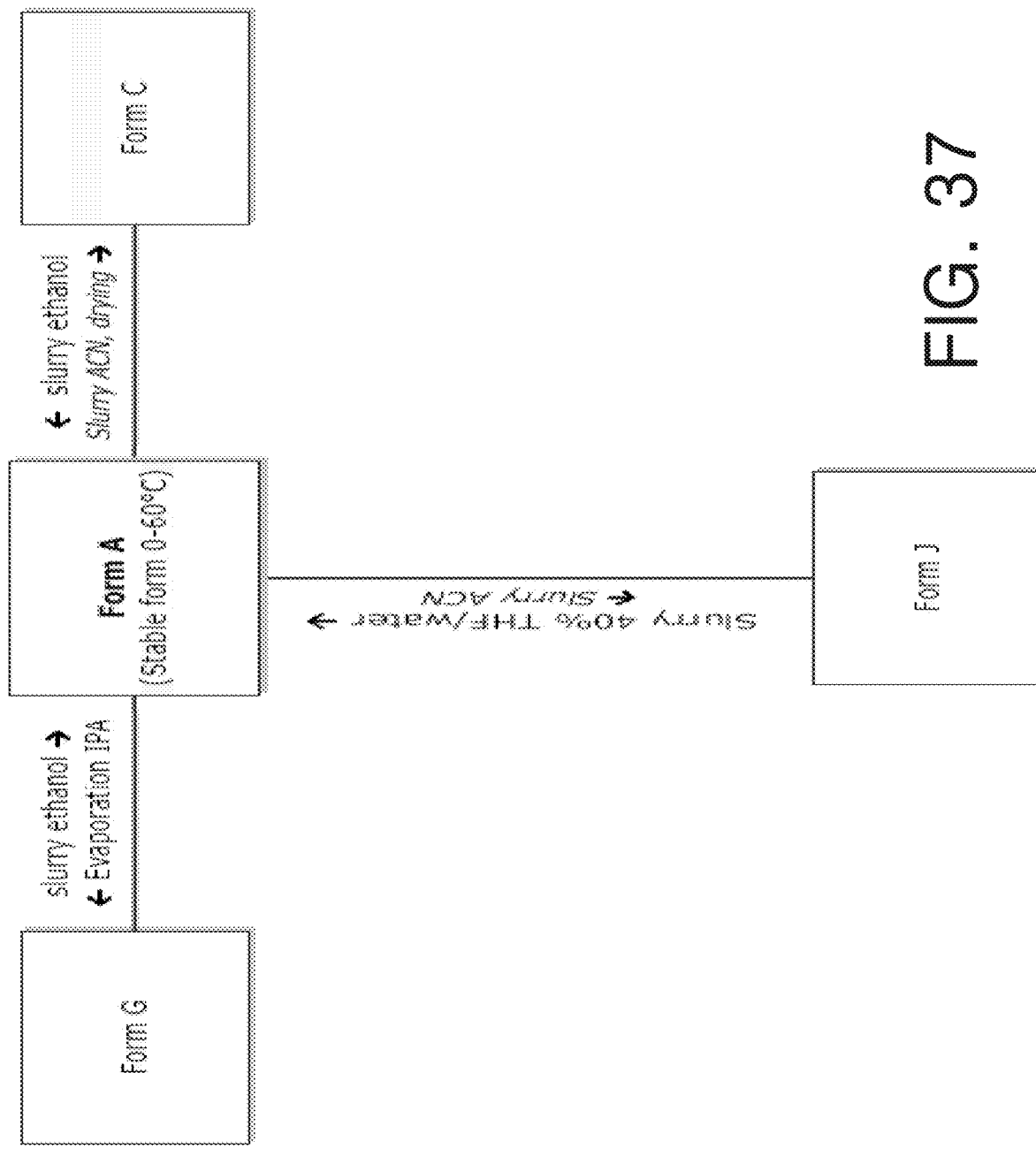
FIG. 37. Illustrates the form diagram of the 4 identified crystalline forms. Conversions in italics indicate unverified pathways.
Figure 38:
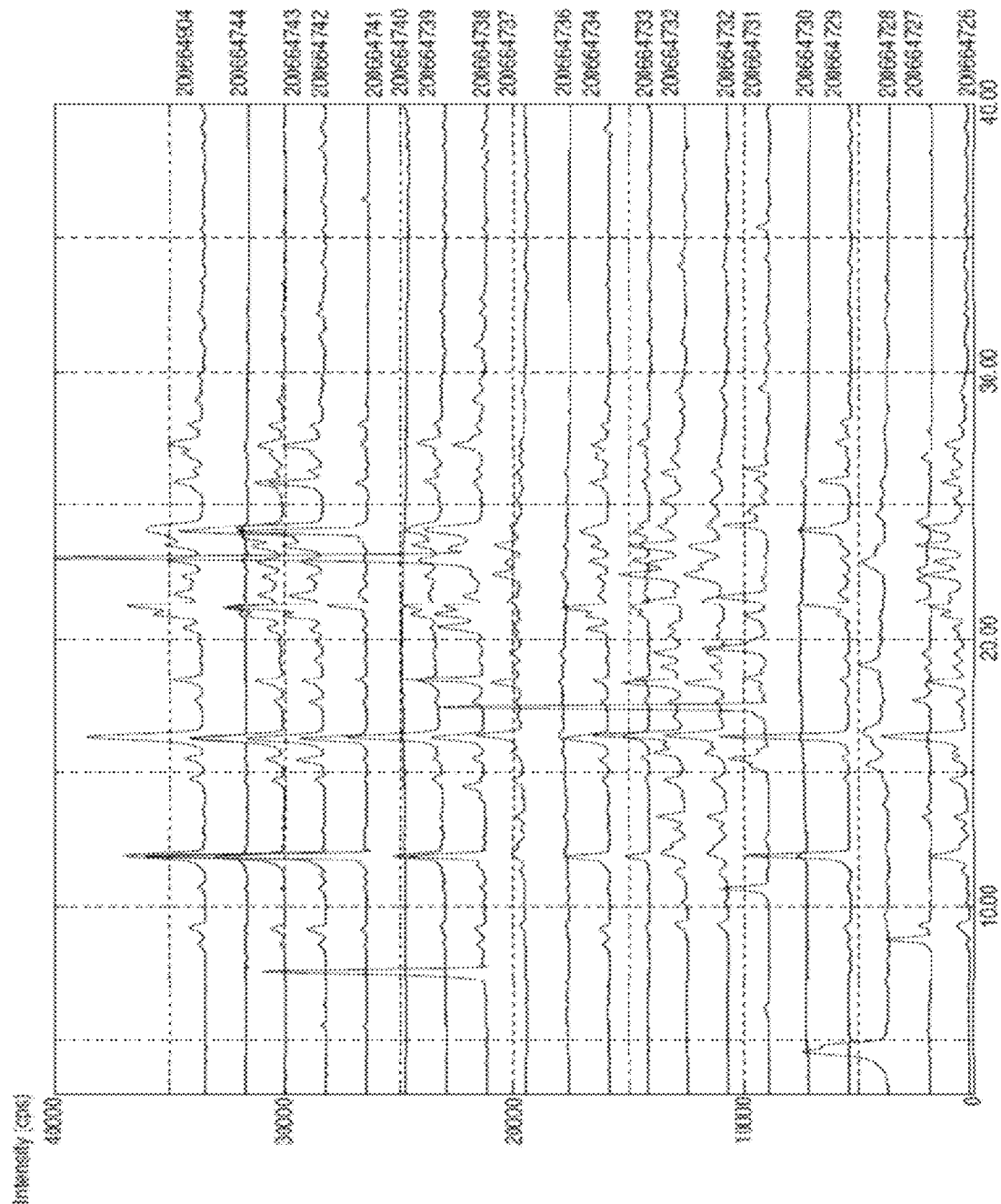
FIG. 38. Illustrates the XRPD pattern of evaporation series (Ax_y-experiments). 9 digit number corresponds to the LIMS-Sample/ID given in Table 1.
Figure 39:
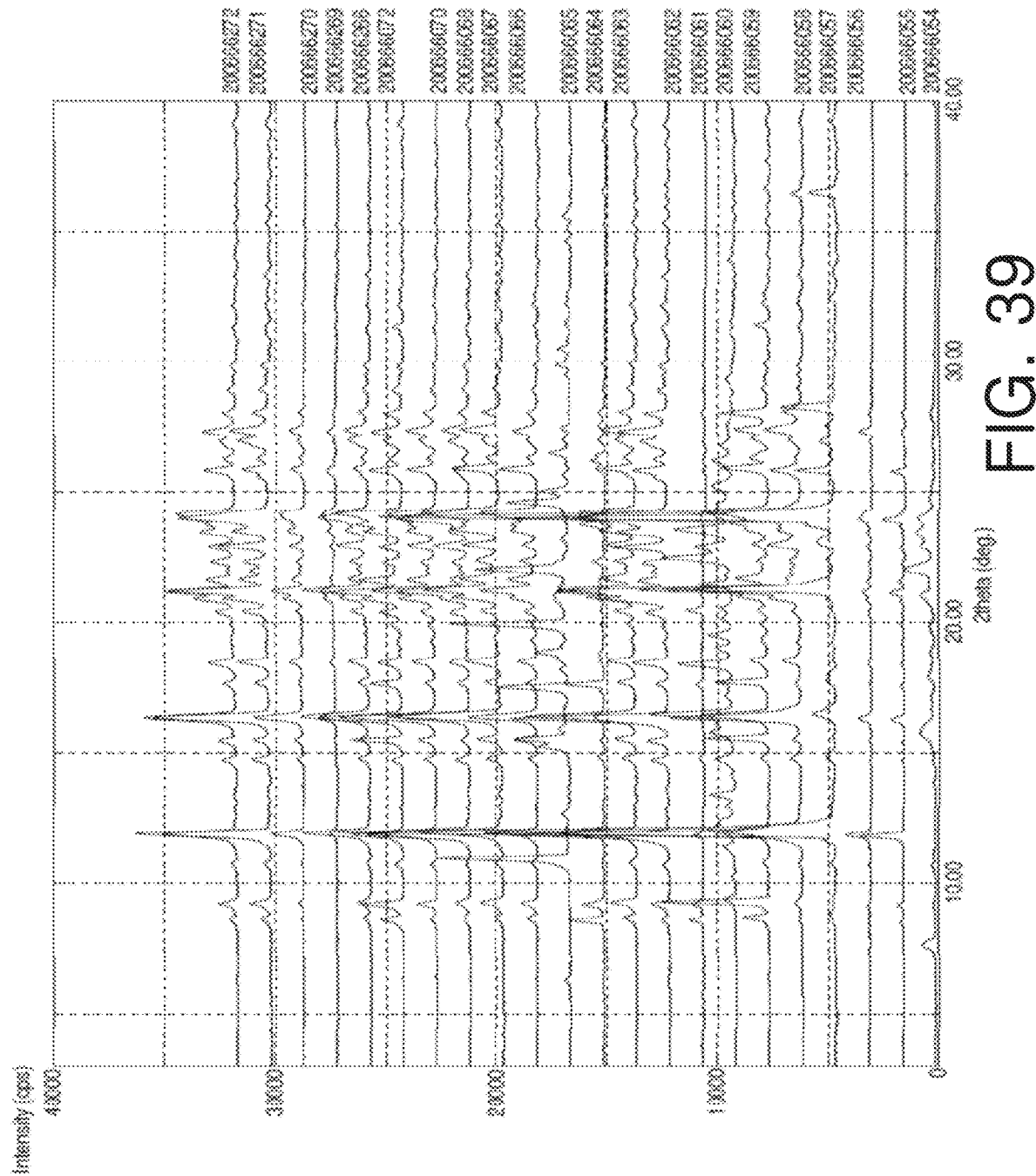
FIG. 39. Illustrates the XRPD pattern of cooling/precipitation series (Bx_y-experiments). 9 digit number corresponds to the LIMS-Sample/ID given in Table 2.
Figure 40:
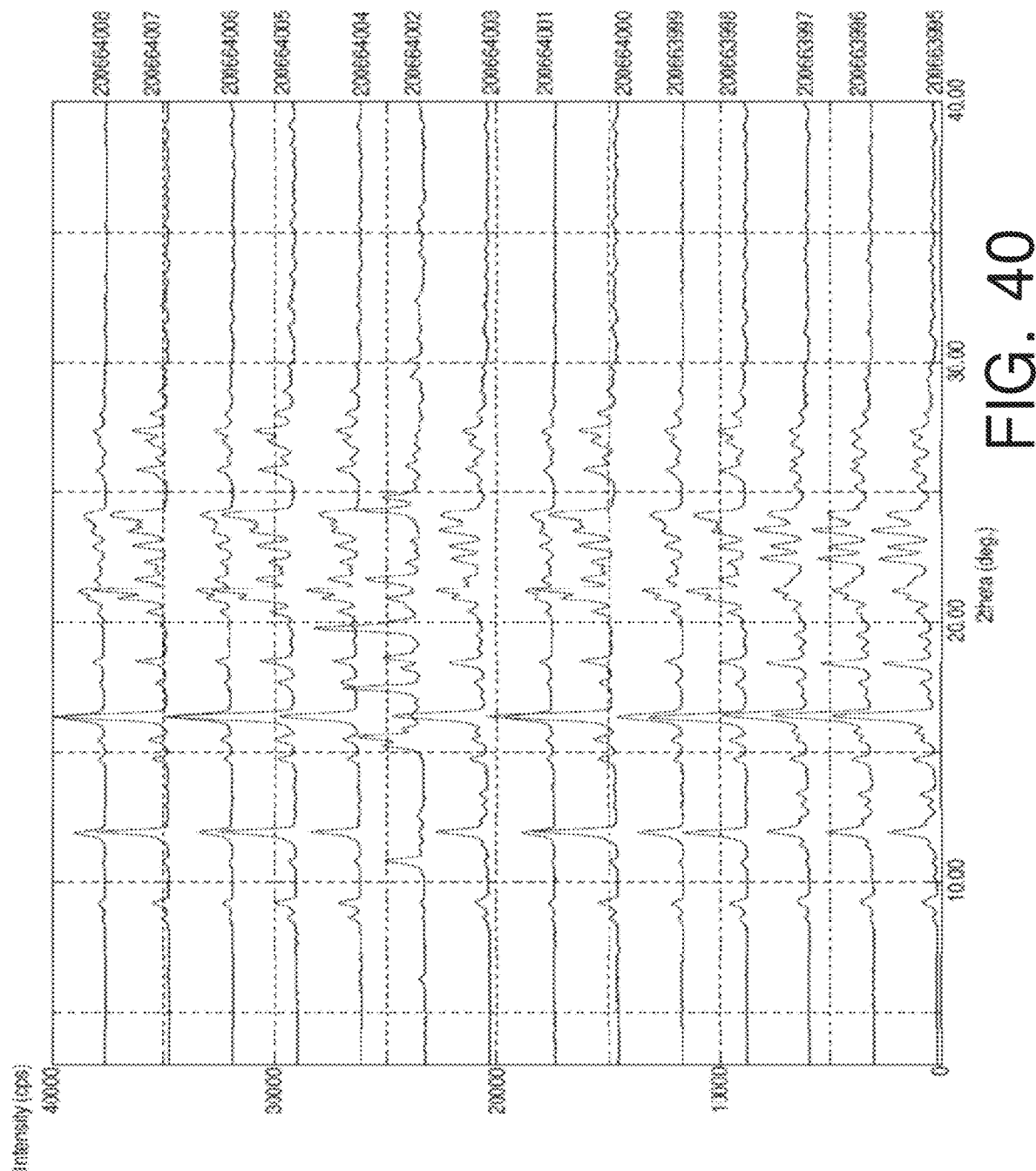
FIG. 40. Illustrates the XRPD pattern of slurry series (Cx_y-experiments, part 1). 9 digit number corresponds to the LIMS-Sample/ID given in Table 3.
Figure 41:
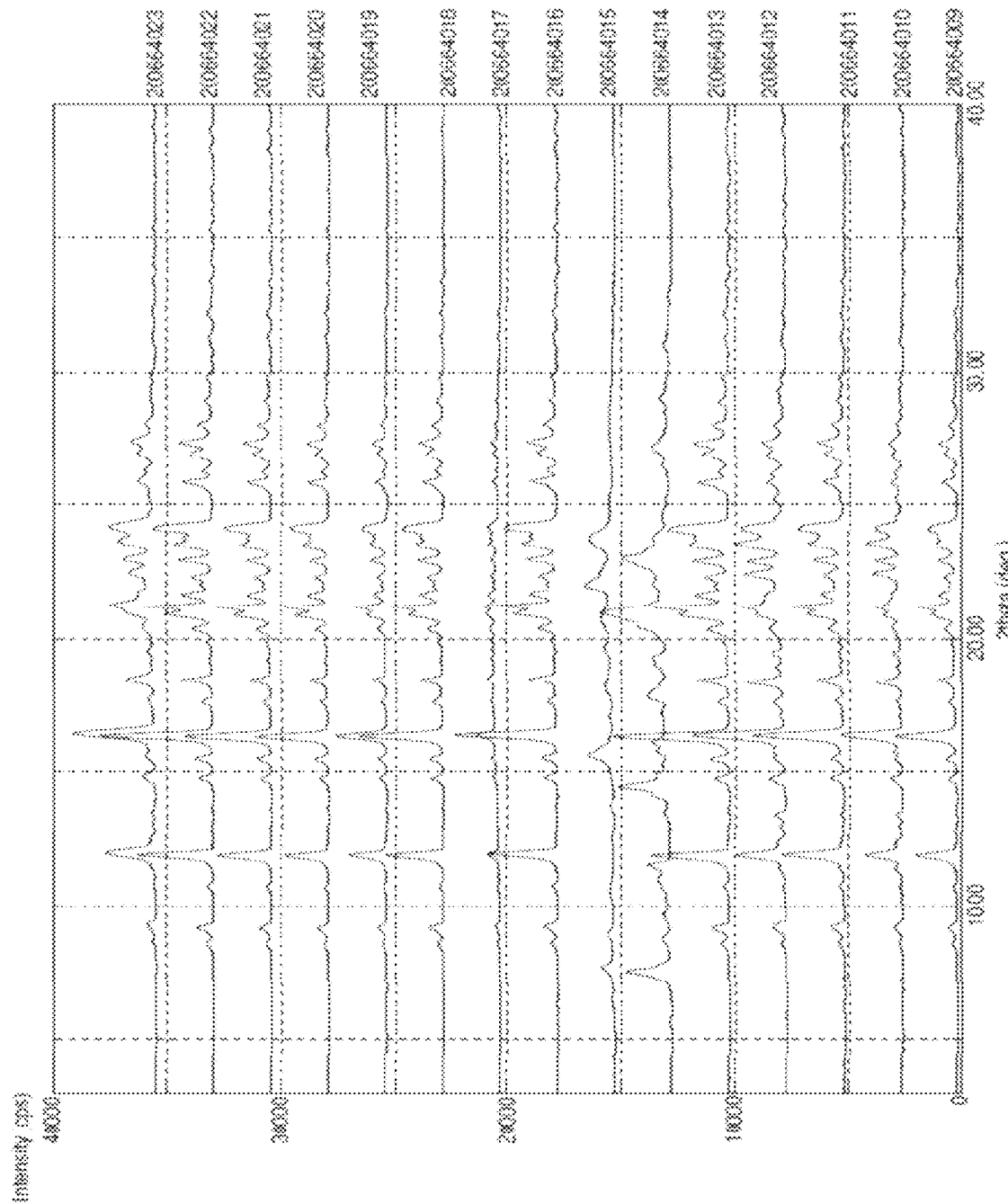
FIG. 41. Illustrates the XRPD pattern of slurry series (Cx_y-experiments, part 1). 9 digit number corresponds to the LIMS-Sample/ID given in Table 3.

The crystalline forms of the compound of formula (I), including those described herein (e.g., Form A, B, C, D, E, F, G, H, I, or J) can interconvert. In certain embodiments, a crystalline form of the compound of formula (I) as described herein converts to Form A, where Form A is as described herein. The crystalline forms can interconvert as set forth in FIG. 37.

Methods of Agonizing TLRs

Further provided herein are methods of agonizing Toll-like receptors (TLRs) by contacting a toll-like receptor with an effective amount of a crystalline form of the compound of formula (I) described herein, where the effective amount agonizes the TLR. The TLR can be Toll-like receptor 8 (TLR8). The TLR can be in a cell where the cell is an immune response cell. The cell can be a myeloid dendritic cell, a monocyte cell, or a natural killer cell. The cell can be a myeloid dendritic cell. The cell can be a monocyte cell. The cell can be a natural killer cell. The cell can be part of an organism (e.g., a mammal). The organism can be a human. The crystalline form can be in solution as part of a dose, for example, by administration through intravenous administration.

Also provided herein are methods of modulating the level, activity, or function of a protein associated with a disease (e.g. cancer). The method includes contacting the protein (e.g. TLR) with an effective amount of a compound, or pharmaceutically acceptable salt thereof, as described herein.

Methods of Treating

Provided herein are methods of treating cancer using a crystalline form of the compound of formula (I) described herein. In one aspect, the method includes treating cancer by administering a therapeutically effective amount of a crystalline form of the compound of formula (I) described herein to a subject in need thereof, thereby treating the cancer. The cancer can be a solid tumor cancer or lymphoma as described herein. The cancer can be colon carcinoma, ovarian cancer, breast cancer, head and neck cancer, renal cancer, bladder cancer, hepatocellular cancer, or lymphoma. The cancer can be colon carcinoma. The cancer can be ovarian cancer. The cancer can be breast cancer. The cancer can be head and neck cancer. The cancer can be renal cancer. The cancer can be bladder cancer. The cancer can be hepatocellular cancer. The cancer can be lymphoma. The cancer can be treated by agonizing a TLR (e.g., TLR8) as described herein. The method of treating cancer can further include co-administering an anti-cancer agent described herein.

Depending on the cancer to be treated and the subject's condition (e.g., age, current symptoms, current health), a compound described herein, e.g., Compound A or a pharmaceutically acceptable salt thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration.

Compounds described herein, e.g., Compound A or a pharmaceutically acceptable salt thereof, may be formulated, alone or together, in suitable dosage unit with pharmaceutically acceptable excipients, carriers, adjuvants and vehicles described herein and for which are appropriate for the desired route of administration.

In certain embodiments, a compound described herein, e.g., Compound A or a pharmaceutically acceptable salt thereof, is prepared for administration by injection (e.g., intravenous, subcutaneous, intramuscular, etc.). In embodiments, the pharmaceutical composition is prepared for intravenous administrations. In certain embodiments, the pharmaceutical composition includes a pharmaceutically acceptable excipient described herein and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The excipient can be liquid or solid and is selected, with the planned manner of administration in mind, so as to provide for the desired bulk, consistency, etc., when combined with a compound described herein in formulating a pharmaceutical composition contemplated herein. In certain embodiments, compositions can be administered to the patient in a single dosage comprising a therapeutically effective amount of a compound described herein. The compound can be a crystalline compound having form A as described herein.

In some embodiments, the compositions can be administered to the patient in multiple doses that include a therapeutically effective amount of a compound described herein, e.g., Compound A or a pharmaceutically acceptable salt thereof.

In some embodiments, the compositions can be administered to the patient in a single, daily dosage form, once per day. In other embodiments, the compositions can be administered to the patient two or more (i.e., two, three, four or more) times per day, or as needed according to the particular treatment regimen designed by the patient's physician.

The amount of the compositions administered each time throughout the treatment period can be the same. Alternatively, the amount administered each time during the treatment period can vary (e.g., the amount administered at a given time can be more or less than the amount administered previously). For example, doses given later in therapy can be lower than those administered during the acute phase (i.e., earlier stages) of treatment. Appropriate dosing schedules depending on the specific circumstances will be apparent to persons of ordinary skill in the art.

In other embodiments where treatment includes more than one dose, the doses administered during the entirety of the treatment are all equal (i.e., the same concentration of compound is administered in each dose). In certain embodiments, the doses administered during the treatment are not all the same amount (e.g., the amount can increase or decrease during treatment). In certain such embodiments, the doses increase over time. In certain embodiments, the doses decrease over time. Increasing dose over the course of treatment can, in embodiments, mitigate undesired side effects.

In certain embodiments, dose, dose frequency, and duration are adjusted to result in a therapeutically effective concentration of the compounds described herein in a subject. In certain embodiments the plasma concentration is maintained above the minimal effective concentration (MEC). In certain embodiments, compounds described herein (e.g., in a pharmaceutical composition) are administered with a dosage regimen (i.e., a combination of doses designed to achieve one or more desired effects) designed to maintain a concentration above the MEC for 10-90% of the time, between 30-90% of the time, or between 50-90% of the time.

In certain embodiments, dose, dose frequency, and duration of the induction phase may be selected to achieve a desired effect, e.g., a therapeutic effect, within a specified time period. In certain embodiments, it is desirable to achieve a desired effect as quickly as possible. In such embodiments, early intervention by administration of high dose and/or high dose frequency of compounds described herein may be desirable.

In certain embodiments, it is desirable to mitigate an undesired side effect. In certain embodiments, early intervention by administration of a low dose and/or low dose frequency and/or long duration may be desirable. In embodiments, early intervention by administration with a low dose and/or low dose frequency and/or long duration mitigates undesired side effects. For example, early intervention by administration with relatively low doses, may result in better tolerance of the pharmaceutical agent. Such embodiments may include gradual increases of dose over time.

In certain embodiments, doses, dose frequency, and duration of the induction phase may be selected to achieve an acceptable safety profile. For example, in certain embodiments, such variables may be selected to mitigate toxicity of the pharmaceutical composition. In certain such embodiments, doses increase over time.

In certain embodiments, the treatment includes administration of one, two, three, four, five, six, seven, eight, nine, ten, eleven, twelve, thirteen, fourteen, fifteen, sixteen, seventeen, eighteen, nineteen, twenty, or more than twenty doses.

In certain embodiments, subjects are monitored for effects (therapeutic and/or toxic effects) and doses, dose frequency, and/or duration of treatment may be adjusted based on the results of such monitoring. It will be recognized by one of ordinary skill in the art that doses, dose frequency, and duration of treatment may be manipulated independently to achieve a desired effect.

Combinational Therapies

One or more additional therapies, such as additional active ingredients (e.g., compounds described herein or pharmaceutically acceptable salts thereof, or anti-cancer agents), can be used in combination. In certain embodiments, one or more additional anti-cancer agents described herein are used in combination with compounds described herein, e.g., Compound A or a pharmaceutically acceptable salt thereof.

Anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine;

isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O_6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional active agents include, but are not limited to, oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT), sulindac, and etoposide.

In certain embodiments the additional active agent is a taxol, gemcitabine, or cisplatin (including cisplatin derivatives such as, for example, carboplatin or oxaliplatin). In other embodiments, the additional active agent is etoposide, tamoxifen, taxotere, or cytarabine. In still other embodiments, the additional active agent is pacilitaxel, tamoxifen, or taxol. In another embodiment, the additional active agent is daunorubicin, prdisone, doxorubicin, or adriamycin.

As used herein, the terms "in combination" and "co-administration" are used interchangeably and include the use of more than one therapy (e.g., one or more prophylactic and/or therapeutic agents). However, the use of the terms does not restrict the order in which therapies (e.g., compounds described herein and anti-cancer agents) are administered to a patient with a disease or disorder. A first therapy (e.g., a compound described herein, including pharmaceutically acceptable salts thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., an anti-cancer agent) to the subject. Triple therapy is also contemplated herein (e.g., a compound described herein and two anti-cancer agents described herein).

Anti-cancer agents can be administered prior to, concurrently with, or subsequent to the administration of compounds described herein, e.g., Compound A or a pharmaceutically acceptable salt thereof. Administration of one or more of the compounds provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compounds provided herein can be independent of the route of administration of a second therapy. In one embodiment, the compounds provided herein are administered orally. In another embodiment, the compounds provided herein are administered intravenously. Thus, in accordance with these embodiments, the compounds provided herein can be administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In certain embodiments, a compound provided herein and a second therapy are administered by the same mode of administration, e.g., orally or by IV. In another embodiment, a compound provided herein is administered by one mode of administration, e.g., by IV, whereas the second agent (e.g., an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the first active agent, and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m2/day, from about 25 to about 500 mg/m2/day, from about 50 to about 250 mg/m2/day, or from about 50 to about 200 mg/m2/day. In certain embodiments, GM-CSF may be administered in an amount of from about 60 to about 500 mcg/m2 intravenously over 2 hours or from about 5 to about 12 mcg/m2/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, a compound provided herein, e.g., Compound A or a pharmaceutically acceptable salt thereof, is administered with gemcitabine and cisplatinum to patients with locally advanced or metastatic transitional cell bladder cancer.

In certain embodiments, a compound provided herein, e.g., Compound A or a pharmaceutically acceptable salt thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, e.g., Compound A or a pharmaceutically acceptable salt thereof, is administered with gemcitabine to patients with recurrent or metastatic head or neck cancer.

In certain embodiments, a compound provided herein, e.g., Compound A or a pharmaceutically acceptable salt thereof, is administered to patients with colon cancer in combination with ARISA®, avastatin, taxol, and/or taxotere.

In certain embodiments, a compound provided herein, e.g., Compound A or a pharmaceutically acceptable salt thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., Compound A or a pharmaceutically acceptable salt, thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., Compound A or a pharmaceutically acceptable salt thereof, is administered to patients with refractory colorectal cancer in combination with capecitabine, xeloda, and/or CPT-11.

In certain embodiments, a compound provided herein, e.g., Compound A or a pharmaceutically acceptable salt thereof, is administered with capecitabine and irinotecan to patients with refractory colorectal cancer or to patients with unresectable or metastatic colorectal carcinoma.

In certain embodiments, a compound provided herein, e.g., Compound A or a pharmaceutically acceptable salt thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., Compound A or a pharmaceutically acceptable salt thereof, is administered in combination with ABT-737 (Abbott Laboratories) and/or obatoclax (GX15-070) to patients with lymphoma and other blood cancers.

In certain embodiments, a compound provided herein, e.g., Compound A or a pharmaceutically acceptable salt, thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., Compound A or a pharmaceutically acceptable salt thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., Compound A or a pharmaceutically acceptable salt thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., Compound A or a pharmaceutically acceptable salt thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In such embodiments, the compound described herein, e.g., Compound A or a pharmaceutically acceptable salt thereof, is administered intravenously.

Also encompassed herein is a method of increasing the dosage of an anti-cancer drug or agent that can be safely and effectively administered to a patient, which includes administering to the patient (e.g., a human) a compound provided herein, or a pharmaceutically acceptable salts thereof. Patients that can benefit by this method are those likely to suffer from an adverse effect associated with anti-cancer drugs for treating a specific cancer of the breast. The administration of a compound provided herein, or pharmaceutically acceptable salt thereof, in embodiments, alleviates or reduces adverse effects which are of such severity that it would otherwise limit the amount of anti-cancer drug.

In one embodiment, a compound provided herein, or pharmaceutically acceptable salt thereof is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In one embodiment, a compound provided herein, or pharmaceutically acceptable salt thereof is administered orally and daily in an amount ranging from about 0.1 to about 50 mg, or from about 2 to about 50 mg, prior to, during, or after the occurrence of the adverse effect associated with the administration of an anti-cancer drug to a patient. In one embodiment, a compound provided herein, or pharmaceutically acceptable salt thereof is administered orally and daily in an amount ranging from about 1 to about 50 mg, or from about 2 to about 50 mg, prior to, during, or after the occurrence of the adverse effect associated with the administration of an anti-cancer drug to a patient. In one embodiment, a compound provided herein, or pharmaceutically acceptable salt thereof is administered orally and daily in an amount ranging from about 0.1 to about 25 mg, prior to, during, or after the occurrence of the adverse effect associated with the administration of an anti-cancer drug to a patient. In one embodiment, a compound provided herein, or pharmaceutically acceptable salt thereof is administered orally and daily in an amount ranging about 1 to about 25 mg, prior to, during, or after the occurrence of the adverse effect associated with the administration of an anti-cancer drug to a patient. In certain embodiments, one or more of the compounds provided herein, or pharmaceutically acceptable salts thereof, are administered in combination with specific agents such as heparin, aspirin, coumadin, or G-CSF to avoid adverse effects that are associated with anti-cancer drugs such as but not limited to neutropenia or thrombocytopenia.

In another embodiment, encompassed herein is a method of treating, preventing and/or managing cancer, by administering one or more of the compounds provided herein, or pharmaceutically acceptable salts thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compounds provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. Compounds provided herein, or pharmaceutically acceptable salts thereof and other active ingredient can be administered to a patient prior to, during, or after the occurrence of the adverse effect associated with conventional therapy.

In certain embodiments, the compounds provided herein, or pharmaceutically acceptable salts thereof are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, one or more of the compounds provided herein are administered daily in a single or divided doses in, for example, a four to six week cycle with a rest period of about a week or two weeks. The cycling method further allows the frequency, number, and length of dosing cycles to be increased. Thus, encompassed herein in certain embodiments is the administration of a compound provided herein or pharmaceutically acceptable salts thereof, for more cycles than are typical when it is administered alone. In certain embodiments the compounds provided herein, or pharmaceutically acceptable salts thereof, are administered for a greater number of cycles that would typically cause dose-limiting toxicity in a patient to whom a second active ingredient is not also being administered.

In one embodiment, the compounds provided herein are administered daily and continuously for about three or four weeks at a dose of from about 0.1 to about 150 mg/d followed by a break of one or two weeks. In one embodiment, the compounds provided herein are administered daily and continuously for about three or four weeks at a dose of from about 1 to about 150 mg/d followed by a break of one or two weeks. In one embodiment, the compounds provided herein are administered daily and continuously for about three or four weeks at a dose of from about 0.1 to about 50 mg/d followed by a break of one or two weeks. In one embodiment, the compounds provided herein are administered daily and continuously for about three or four weeks at a dose of from about 1 to about 50 mg/d followed by a break of one or two weeks.

In another embodiment, a compound provided herein and a second active ingredient are administered orally, with administration of the compound provided herein occurring 30 to 60 minutes prior to a second active ingredient, during a cycle of four to six weeks. In certain embodiments, the combination of the compound provided herein and a second active ingredient is administered by intravenous infusion over about 90 minutes every cycle. In certain embodiments, one cycle comprises the administration from about 0.1 to about 150 mg/day of the compound provided herein and from about 50 to about 200 mg/m2/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein may vary depending on their use. For example, a dosage form used in the acute treatment of a disease may contain larger amounts of one or more of the active ingredients than a dosage form used in the chronic treatment of the same disease. Similarly, a parenteral dosage form may contain smaller amounts of one or more of the active ingredients than an oral dosage form used to treat the same disease. See, e.g., Remington's Pharmaceutical Sciences, 18th ed., Mack Publishing, Easton Pa. (1990).

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the U.S. Pharmacopeia (USP) 25 NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiments, the dosage forms provided herein comprise one or more of the compounds provided herein, or pharmaceutically acceptable salts thereof, in an amount ranging from about 0.10 to about 1000 mg, from about 0.10 to about 500 mg, from about 0.10 to about 200 mg, from about 0.10 to about 150 mg, from about 0.10 to about 100 mg, or from about 0.10 to about 50 mg. In certain embodiments, the dosage forms provided herein comprise one or more of the compounds provided herein, or pharmaceutically acceptable salts thereof, in an amount of about 0.1, about 1, about 2, about 5, about 7.5, about 10, about 12.5, about 15, about 17.5, about 20, about 25, about 50, about 100, about 150, or about 200 mg.

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, Remington's Pharmaceutical Sciences, 18th ed., Mack Publishing, Easton Pa. (1990).

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVICEL RC-581, AVICEL-PH-105 (FMC Corporation, American Viscose Division, Avicel Sales, Marcus Hook, Pa.), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, Md.), a coagulated aerosol of synthetic silica (Degussa Co. of Plano, Tex.), CAB-O-SIL (a pyrogenic silicon dioxide, Cabot Co. of Boston, Mass.), and mixtures thereof. In certain embodiments, if used at all, lubricants are used in an amount of less than about 1 weight percent of the pharmaceutical compositions or dosage forms into which they are incorporated.

In certain embodiments, provided herein is a solid oral dosage form, comprising one or more of the compounds provided herein, or pharmaceutically acceptable salts thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising one or more of the compounds provided herein, or pharmaceutically acceptable salts thereof; and anhydrous lactose, microcrystalline cellulose, polyvinylpyrrolidone, stearic acid, colloidal anhydrous silica, and gelatin.

In certain embodiments, the active ingredients provided herein are administered by controlled release means or by delivery devices. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, for example, in Remington's Pharmaceutical Sciences, 16th and 18th eds., Mack Publishing, Easton Pa. (1980 & 1990).

EXAMPLES

Example 1: General Chemistry and Technique Description

Melting Point by DSC.

Differential scanning calorimetry was performed with power compensation using a DSC-systems (DSC 822e—Mettler Toledo)/analytical micro balance. An accurately weighed amount of sample (typically 1-5 mg), was placed in a clean and dry aluminum crucible and closed with an aluminum cap with a hole. A second crucible was the reference crucible.

Conditions: starting temperature: 20° C.; heating rate: 10° C./min final temperature: 300° C.; atmosphere: $N_2$ (flow 20 mL/min)

TGA Volatile Components.

Thermogravimetry was performed using a TGA 851e apparatus that included an oven, oven temperature sensor and sample temperature sensor/aluminum oxide pan/analytical micro balance. An empty aluminum oxide pan was used to collect the background curve, after which an accurately weighed amount of sample (10 mg) was placed in a clean and dry pan. The measurement was done as described above.

Conditions: starting temperature: 25° C.; heating rate: 5° C./min final temperature: 300° C.; atmosphere: $N_2$ (flow 50 mL/min)

$^1$H NMR was performed using a Bruker AVANCE 400 MHz with DMSO-$D_6$ or $CDCl_3$ as solvent and either Tetramethylsilane (TMS) or solvent peak as the internal standard. Decoupling was performed using inverse gate decoupling. Assays were determined using the ACD/Spec Manager 9 software suite by comparing integration areas of the compound with those of an internal standard (typically hydrochinondimethylether).

Light Microscopy with Hot Stage was performed with an Olympus BX41 with Di-Li 5MP camera and grab&measure software. A Hotstage Mettler Toledo FP90 with FP 82 heating table was used. Samples were prepared with brushes onto object holders. Observation was done using unpolarized light or polarized light using two polarization filters at 40, 100, 200 or 400× magnification. Images were taken by software and exported as JPEG, (scale is only approximate and not validated).

X-Ray powder diffraction was performed with a MiniFlex by Rigaku Corporation using silicon low background sample holders (diameter 24 mm, pit 0.2 mm) and Cu, l=1.54056 Å, 15 kV tubes. Samples were ground with mortar and pestle when a sufficient amount was isolated, which lead to consistent results, less preferred orientation and better handling of material with huge particle size. Solid was positioned on a sample holder prepared with grease and flattened with a disc of glass Method: Angle: $2\theta=2°$ to $2\theta=40°$; Sampling width 0.02 [$2\theta$]; Measurement time: 75 minutes.

For purity estimation and determination of the solubility in solution a generic in-house HPLC method was used. HPLC was performed using a Phenomenex Luna 3 μm C18 (50×4.6 mm) column and detected with a DAD detector, recording at 214 nm.

Diluent: 0.5 mg/mL in ACN/$H_2O$ 1:1+1% TFA

Eluents: A="$H_2O$+0.05% $CF_3COOH$"; B="$CH_3CN$+0.05% $CF_3COOH$"

Method: Injection: 5 μL; Flow: 1.0 mL/min

| Min | Eluents |
|---|---|
| 0.00 | % A = 70.0 |
|  | % B = 30.0 |
| 0.10 | % A = 70.0 |
|  | % B = 30.0 |
| 15.1 | % A = 5.0 |
|  | % B = 95.0 |
| 16.1 | % A = 5.0 |
|  | % B = 95.0 |
| 17.1 | % A = 70.0 |
|  | % B = 30.0 |
| 12.1 | % A = 70.0 |
|  | % B = 30.0 |

Example 2: Screening Techniques

The polymorphism screening was performed using an approach to find kinetically preferred polymorphs as well as thermodynamically preferred or in other words more stable polymorphs. The kinetically preferred polymorphs were examined using evaporation and cooling crystallizations. Thermodynamically preferred polymorphs were examined using slurry type experiments.

Figure 3:
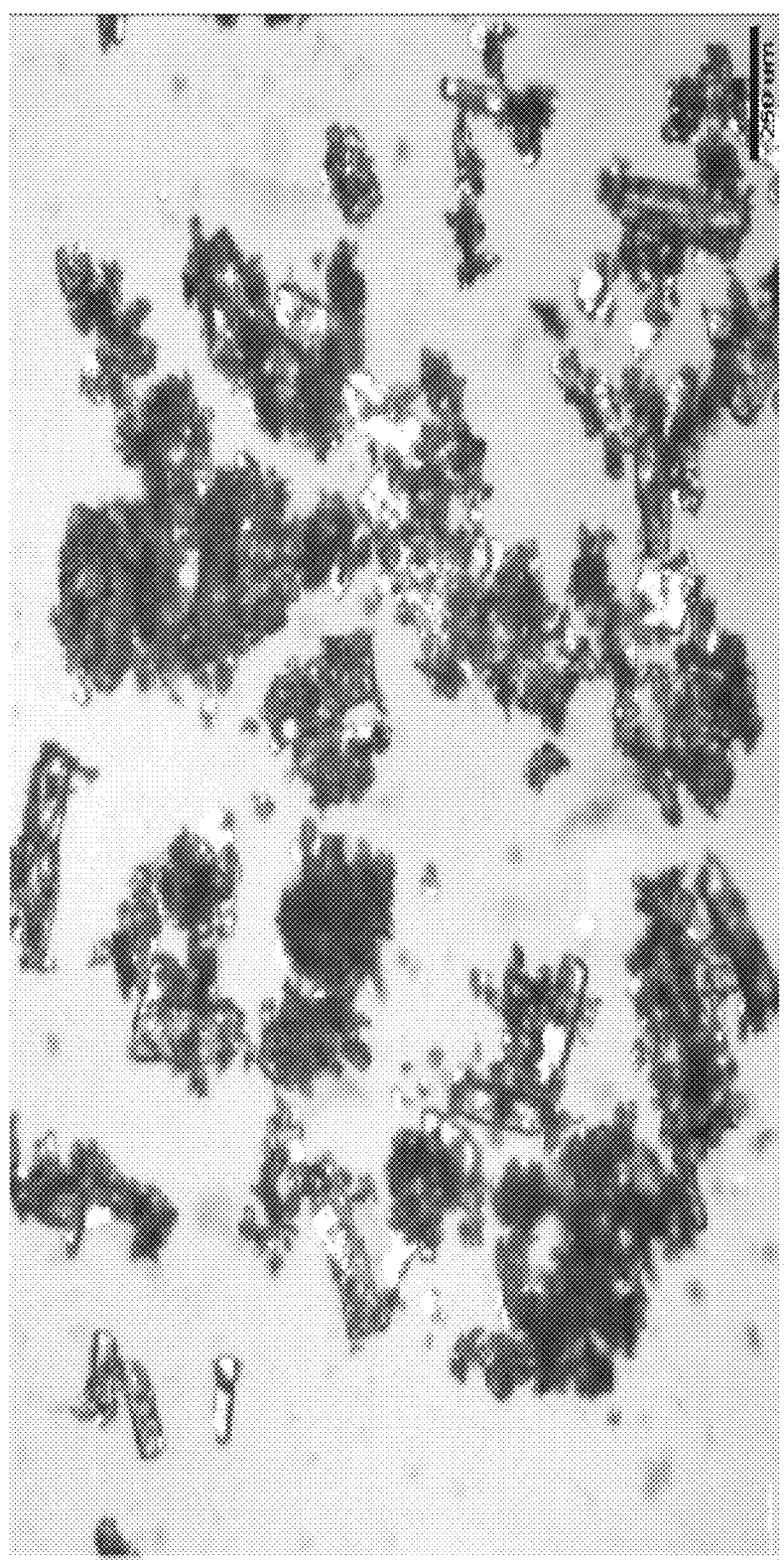
FIG. 3. Illustrates the microscopy picture of Starting material. The bar indicates 250 µm.

The forms described herein are assigned to sequential capital letters (e.g., A, B, C . . . ). The starting material used for screening was a pale yellow to beige solid. NMR assay of the material was found to be 95.6% w/w and HPLC indicated 99.07% a/a. The material appeared crystalline by microscopy (FIG. 3) as well as by XRPD which showed a mixture of Forms A and G.

DSC indicated a melting point of around 202° C. with a second melting event around 211° C. TGA with SDTA curve indicated a weight loss of around 0.2% w/w up to the endothermic events as well as further weight loss during melting/form conversion which probably is due to beginning degradation.

Screening. The screening was done in 3 series: A—evaporation, B—fast cooling and C—slurries. Experiments struck through indicate that these experiments were not performed because of low solubility of the starting material. The experiment name is provided in each table.

Evaporation screening. For the evaporation experiments approximately 40 mg starting material was suspended/dissolved in each of the solvents listed (up to 4 mL) per Table 1. Solvents were chosen to have a high diversity, e.g., in polarity, protic/aprotic, acceptability according to ICH guidelines.

Experiments where no dissolution occurred at room temperature were heated to maximum 60° C. and in case still no dissolution occurred were filtered at elevated temperature to obtain a more concentrated starting solution. The solutions were evaporated in a drying oven starting at 25° C. and 850 mbar with a constant flow of nitrogen decreasing vacuum after 3 days 750 mbar. After 5 days remaining solutions were concentrated using a nitrogen stream. The resulting solids were examined visually and in cases where a sufficient amount of solid was obtained X-ray powder diffraction was performed.

TABLE 1

Evaporation Experiments.

| Experiment No.[1] | Solvent | Dissolved After Heating | Optical Impression | Comment | Form | LIMS-Task/ID | LIMS-Sample/ID |
|---|---|---|---|---|---|---|---|
| [1]A1_1 | [1]heptane | — | — | — | — | | |
| A1_2 | methyl cyclohexane | no | film | — | — | | |
| A1_3 | toluene | no | film/spots | Too few | — | | |
| A1_4 | THF | yes | yellow | — | A G | 305062099 | 200664726 |
| A1_5 | chlorobenzene | no | yellow | — | E | 305062101 | 200664727 |
| A1_6 | trifluoroethanol | yes | oil→wax | — | F | 305062103 | 200664728 |
| A1_7 | acetone | no | beige | — | A | 305062105 | 200664729 |
| A1_8 | MEK | no | oil/spots | — | Am[2] A | 305062107 | 200664730 |
| A1_9 | MIBK | no | film | — | — | | |
| A1_10 | dioxane | no | beige | — | B | 305062109 | 200664731 |
| A2_1 | 2-propanol | no | beige | — | G | 305062111 | 200664732 |
| A2_2 | 1-propanol | no | beige | — | G | 305062113 | 200664733 |
| A2_3 | ethanol | no | film/spots | — | A | 305062115 | 200664734 |
| A2_4 | methanol | yes | beige | — | A G | 305062117 | 200664735 |
| A2_5 | methyl acetate | no | film/spots | — | Am[2] X[3] | 305062119 | 200664736 |
| A2_6 | ethyl acetate | no | film | — | — | | |
| A2_7 | isopropyl acetate | no | film | — | — | | |
| [1]A2_8 | [1]diethylether | — | — | — | — | | |
| AS_9 | TBME | no | film | — | — | | |
| AS_10 | 2-Me-THF | no | yellow | — | G | 305062121 | 200664737 |
| A3_1 | ACN | no | crystals | — | A C | 305062123 | 200664738 |
| A3_2 | DCM | yes | film/spots | — | A | 305062125 | 200664739 |
| A3_3 | DMSO | yes | yellow | — | A | 305063649 | 200664904 |
| [1]A3_4 | [1]NMP | no | — | — | — | | |
| A3_5 | EtOAc wet | no | film/spots | — | Am[2] | 305062127 | 200664740 |
| A3_6 | acetone/water 1/2 | no | beige | — | A | 305062129 | 200664741 |
| A3_7 | EtOH/water 1/1 | yes | brown | — | A X[3] | 305062131 | 200664742 |
| A3_8 | EtOH/water 3/1 | yes | beige | — | A | 305062133 | 200664743 |
| A3_9 | IPA/water 3/1 | yes | film/spots | — | A | 305062135 | 200664744 |
| A3_10 | HOAc/water 1/1 | yes | oil | — | — | | |
| A4_1 | water | no | film | too few | — | | |

[1]Experiments were not performed due to low solubility. Form X indicates additional reflexes that do not correspond to any other observed form.
[2]Am indicates Amorphous.
[3]X indicates additional reflexes not corresponding to other observed forms

TABLE 2

Cooling/precipitation experiments. $T_{max}$ in ° C.

| Experiment No. | Solvent | Vol (mL) | Tmax[° C.]/ solution? | Anti-solvent | Vol (mL) | Optical impression | Form | LIMS-Task/ID | LIMS-Sample/ID |
|---|---|---|---|---|---|---|---|---|---|
| B1_1 | DCM | 0.5 | 60/yes | MCH | 3 | solid | D | 305073328 | 200666054 |
| B1_2 | IPA/water 3/1 | 1 | 60/yes | none | — | solid | A | 305073330 | 200666055 |
| B1_3 | EtOH/water 3/1 | 1 | 60/yes | none | — | solid | A | 305073332 | 200666056 |
| B1_4 | IPA | 2 | 60/yes | none | — | solid | A | 305073334 | 200666057 |
| B1_5 | IPA+/ACN | 0.5/0.5 | 60/yes | none | — | solid | A | 305073336 | 200666058 |
| B1_6 | MeOH | 0.5 | 60/yes | none | — | solid | A | 305073338 | 200666059 |
| B1_7 | DCM + TBME | 0.5 | 60/yes | TBME | 4 | solid | G | 305073340 | 200666060 |
| B1_8 | 1-propanol | 0.5/0.5 | 60/yes | none | — | solid | H | 305073342 | 200666061 |
| B1_9 | 1-propanol + TBME | 1 | 60/yes | TBME | 2 | solid | A | 305073344 | 200666062 |
| B1_10 | 1-propanol + hept | 1 | 60/yes | Heptane | 2 | solid | A | 305073346 | 200666063 |
| B2_1 | 1-propanol + water | 1 | 60/yes | water | 2 | solid | A | 305073348 | 200666064 |
| B2_2 | THF | 4 | 60/yes | none | — | solid | H | 305073350 | 200666065 |
| B2_3 | MEK | 4 | 60/no | none | — | solution | — | | |
| B2_4 | acetone | 4 | 60/no | none | — | solid | A | 305073353 | 200666066 |
| B2_5 | DCM/MeOH + TBME | 0.2/0.25 | r.t./yes | TBME | 3.5 | solid | A G | 305073355 | 200666067 |
| B2_6 | MeOH + water | 0.5 | 60/yes | water | 2 | solid | A | 305073357 | 200666068 |

TABLE 2-continued

Cooling/precipitation experiments. $T_{max}$ in ° C.

| Experiment No. | Solvent | Vol (mL) | Tmax[° C.]/ solution? | Anti-solvent | Vol (mL) | Optical impression | Form | LIMS-Task/ID | LIMS-Sample/ID |
|---|---|---|---|---|---|---|---|---|---|
| B2_7 | EtOAc (wet) | 4 | 60/no | none | — | solution | — | | |
| B2_8 | MEK (wet) | 0.9 | 60/yes | none | — | solid | A | 305073361 | 200666070 |
| B2_9 | ACN/MeOH + ACN | 0.2/0.2 | 60/yes | ACN | 2 | solution | — | | |
| B2_10 | Tol/MeOH 7/3 + Hep | 0.2 | 60/yes | Heptane | 2 | solid | A | 305073365 | 200666072 |
| B3_1 | DMSO + water | 0.4 | 60/yes | water | 0.75 | solid | A | 305074841 | 200666266 |
| B3_2 | DMSO + TBME | 0.4 | 60/yes | TBME | 3 | solid | A | 305074843 | 200666269 |
| B3_3 | NMP + TBME | 0.4 | 60/yes | TBME | 3.5 | solid | A | 305074845 | 200666270 |
| B3_4 | NMP + water | 0.4 | 60/yes | water | 2 | solid | A | 305074843 | 200666271 |
| B3_5 | THF + water | 0.5/0.1 | 60/yes | water | 1.5 | Oil > solid | A | 305074849 | 200666272 |

— indicates no form observed.

TABLE 3

Slurry screening. * solubility determined by HPLC.

| Experiment No. | Solvent | Solution? | Optical impression | mg/mL | HPLC ML (% a/a) | Form | LIMS-Task/ID | LIMS-Sample/ID |
|---|---|---|---|---|---|---|---|---|
| C1_1 | heptane | no | beige | 0.02 | 100.00 | A G | 305054045 | 200663995 |
| C1_2 | MCH | no | beige | 0.08 | 100.00 | A G | 305054047 | 200663996 |
| C1_3 | toluene | no | beige | 0.45 | 87.28 | A G | 305054049 | 200663997 |
| C1_4 | THF | no | beige | 5.71 | 94.83 | A | 305054051 | 200663998 |
| C1_5 | chlorobenzene | no | beige | 1.81 | 92.35 | A | 305054053 | 200663999 |
| C1_6 | trifluoroethanol | yes | solution | >130 | 96.33 | — | | |
| C1_7 | acetone | no | beige | 1.37 | 81.66 | A | 305054055 | 200664000 |
| C1_8 | MEK | no | beige | 3.67 | 92.40 | A | 305054057 | 200664001 |
| C1_9 | MIBK | no | beige | 0.79 | 87.53 | A G | 305054059 | 200664002 |
| C1_10 | dioxane | no | beige | 5.10 | 95.50 | B A | 305054061 | 200664003 |
| C2_1 | 2-propanol | no | beige | 6.86 | 97.18 | A | 305054063 | 200664004 |
| C2_2 | 1-propanol | no | beige | 12.00 | 95.28 | A | 305054065 | 200664005 |
| C2_3 | ethanol | no | beige | 11.60 | 94.59 | A | 305054067 | 200664006 |
| C2_4 | methanol | no | beige | 29.84 | 97.52 | A | 305054069 | 200664007 |
| C2_5 | methyl acetate | no | beige | 0.94 | 85.37 | A | 305054071 | 200664008 |
| C2_6 | ethyl acetate | no | beige | 0.57 | 77.59 | A | 305054073 | 200664009 |
| C2_7 | iPrOAc | no | beige | 0.60 | 86.13 | A G | 305054075 | 200664010 |
| C2_8 | diethylether | no | beige | 0.02 | 70.74 | A | 305054077 | 200664011 |
| C2_9 | TBME | no | beige | 0.16 | 86.76 | A G | 305054079 | 200664012 |
| C2_10 | 2-Me-THF | no | beige | 1.03 | 88.83 | A | 305054081 | 200664013 |
| C3_1 | ACN | no | beige | 0.81 | 84.74 | C J | 305054083 | 200664014 |
| C3_2 | DCM | no | beige | >70 | 98.32 | D | 305054085 | 200664015 |
| C3_3 | DMSO | no | yellow | 28.82 | 95.03 | A | 305054087 | 200664016 |
| C3_4 | NMP | no | yellow | 52.32 | 94.79 | A Am[1] | 305054089 | 200664017 |
| C3_5 | EtOAc wet | no | beige | 2.69 | 84.49 | A | 305054091 | 200664018 |
| C3_6 | ac/water 1/2 | no | beige | 0.48 | 74.20 | A | 305054093 | 200664019 |
| C3_7 | EtOH/water 1/1 | no | beige | 3.22 | 86.64 | A | 305054095 | 200664020 |
| C3_8 | EtOH/water 3/1 | no | beige | 20.96 | 96.08 | A | 305054097 | 200664021 |
| C3_9 | IPA/water 3/1 | no | beige | 16.88 | 96.20 | A | 305054099 | 200664022 |
| C3_10 | HOAc/water 1/1 | yes | solution | >100 | 98.11 | — | | |
| C4_1 | water | no | beige | 0.04 | 89.74 | A G | 305054101 | 200664023 |

[1]Am indicates Amorphous.
— indicates no form observed.
2 digits after decimal point are provided to show minimal amounts in low solubilizing solvents.
Italicized numbers indicate concentration was too high and above linearity.

Slurry Screening.

The slurry experiments were performed by taking approximately 40 mg starting material and slurrying in each of the solvent mixtures as detailed Table 3 using a magnetic stir bar. Solvents were chosen as described to have a high diversity (e.g., in polarity, protic/aprotic). The solvents were not necessarily selected for pharmaceutical suitability in regards to ICH guidelines. Only as much solvent or mixtures as needed to slurry/suspend the material was used—starting from 200 μL to a maximum of 2 mL. The slurries were stirred for 5 days. The suspensions were filtered and the filter cake slightly dried to not destroy potential solvates and subjected to XRPD. In case suspensions started to run through the filter the suspensions were dried using a nitrogen stream. As the solubility was tested in the solvents, the evaporated solvent provides a small amount of solid compared to the material suspended (i.e., the slurry form still should be dominant).

Screening Results and Promotion to Next Phase.

After identification of different forms per XRPD during the screening phase the individual forms were checked (evaporation and cooling screening) by microscopy. HPLC was performed once per form to confirm identity and to get an idea about purity. NMR was done to check for residual solvents and to confirm identity. If sufficient material was left DSC and TGA were also performed to confirm NMR residual solvent results stability. After this first characterization phase further scale-up experiments were performed.

Scale-Up and More Detailed Characterization of Forms.

Figure 4:
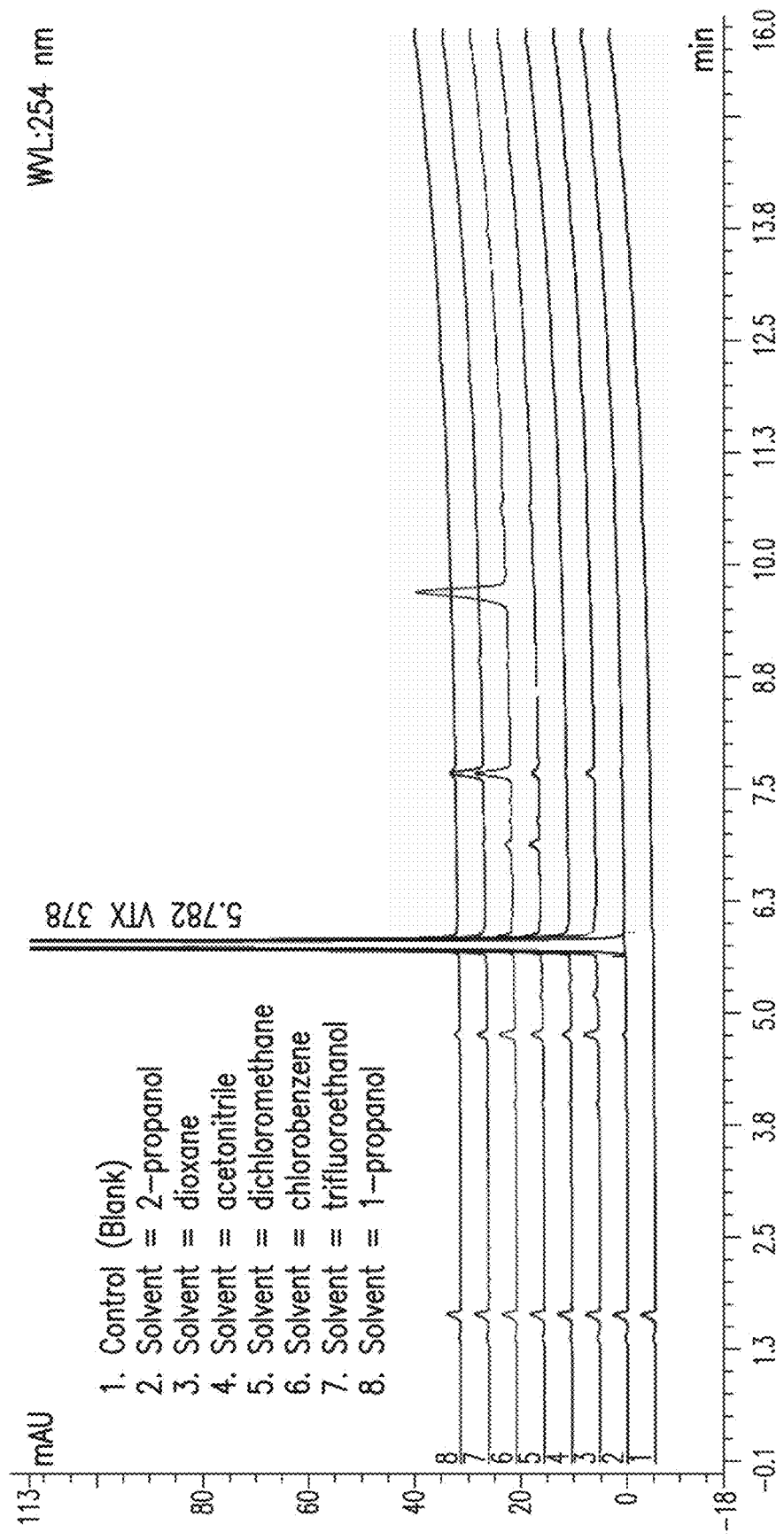
FIG. 4. Illustrates the overlay of 7 forms tested by HPLC with Compound A at 5.78 min. From bottom to top: blank, C2_1, A1_10, C3_1, C3_2, A1_5, A1_6 and A2_1 (corresponding to Experiment Nos. of Table 1-3).
Figure 5:
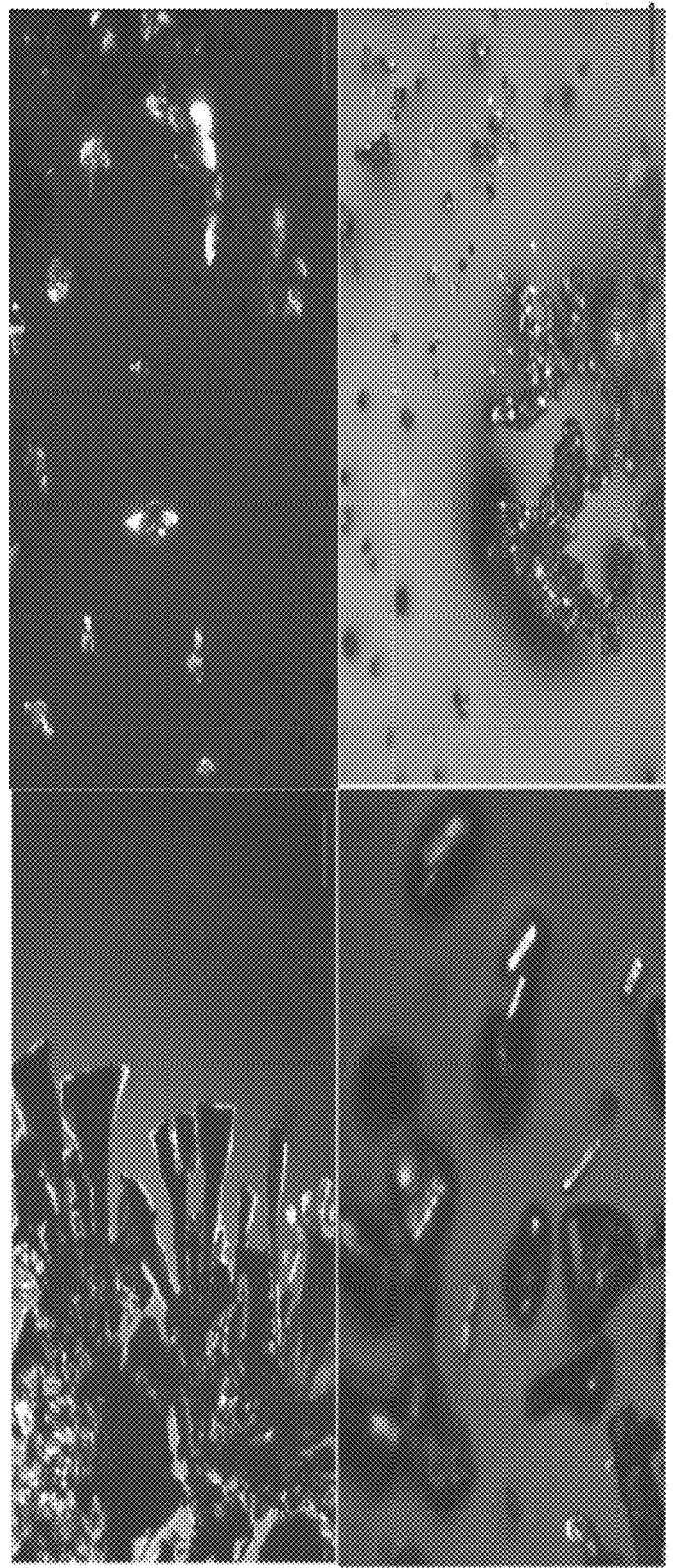
FIG. 5A. illustrates one microscopy picture of different screening samples of form A.
FIG. 5B illustrates another microscopy picture of different screening samples of form A.
FIG. 5C illustrates another microscopy picture of different screening samples of form A.
FIG. 5D illustrates another microscopy picture of different screening samples of form A. All pictures taken with crossed polarized filters. The bar indicates approximately 250 µm.

All six forms were tested by HPLC to ensure that none of the forms is a false positive, e.g., degradation. An overlay of the chromatograms is shown in FIG. 4. All samples showed at least 96% a/a by HPLC with no new impurities (except for solvents e.g., chlorobenzene) compared to the starting material. Form J identified after the screening phase was verified by NMR which confirmed identity.

Example 3: Form Characterization

Form A.

Form A was present in the starting material used for the screening and occurred in nearly all screening experiments. Form A was the most often obtained form and Form A is likely the thermodynamically most stable form from 0 to 60° C.

Figure 6:
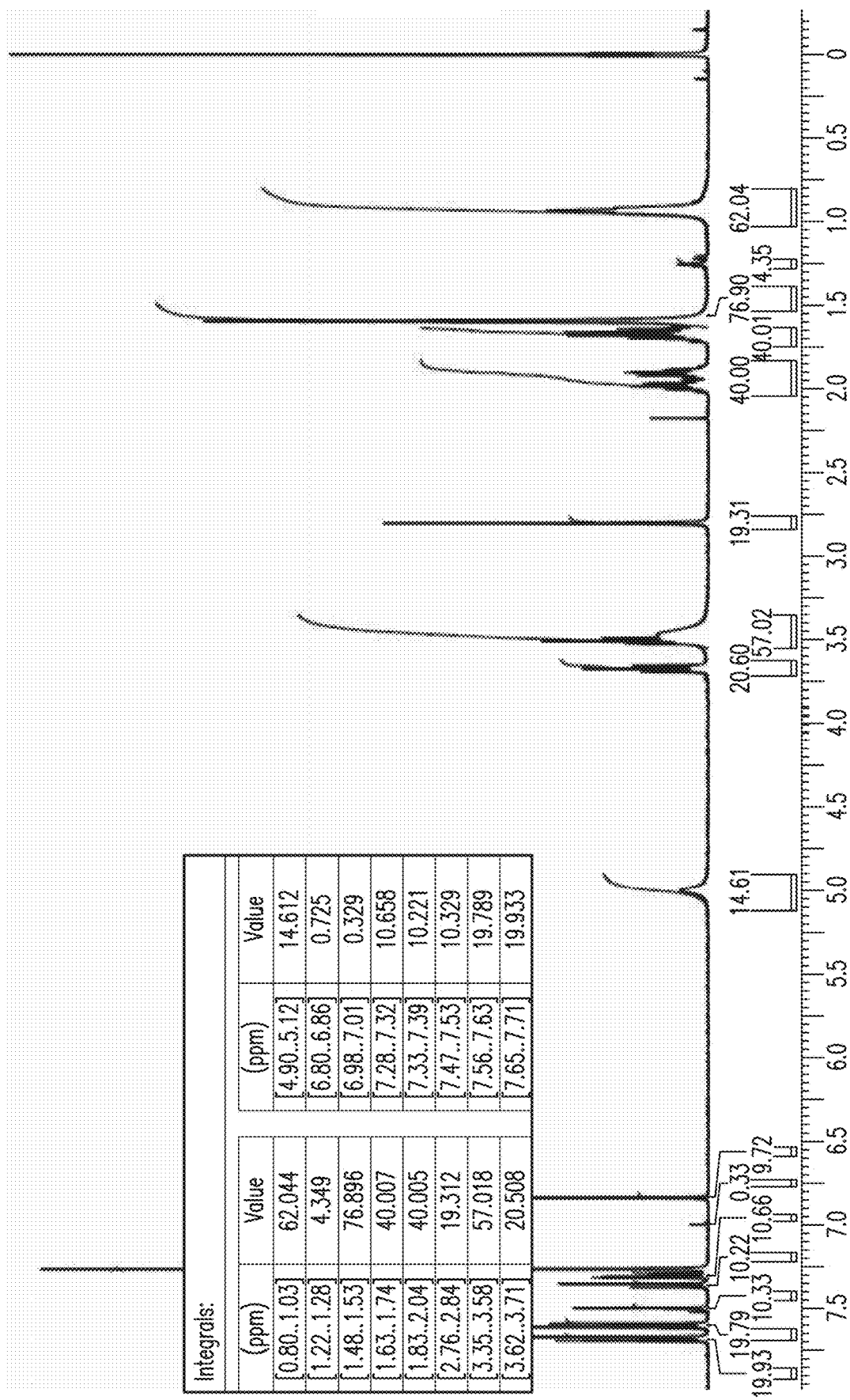
FIG. 6. Illustrates the ¹H NMR of Form A.

The crystal habit of Form A appeared to vary widely (FIGS. 5A, 5B, 5C, and 5D) from agglomerates of fine needles (brushlike), undefined forms (stone knife form), rod-like needles or almost cubic crystals. XRPD (FIG. 42) shows a well resolved pattern with probably nice crystallinity. The $^1$H NMR (FIG. 6) does not show any residual solvents for Form A except for the water signal which is not suitable for quantification.

Thermal analysis showed 2 melting events for Form A (FIG. 7) at 201° C. (peak) and 208° C. (peak) where the latter likely corresponds to the melting point of Form G.

Figure 8:
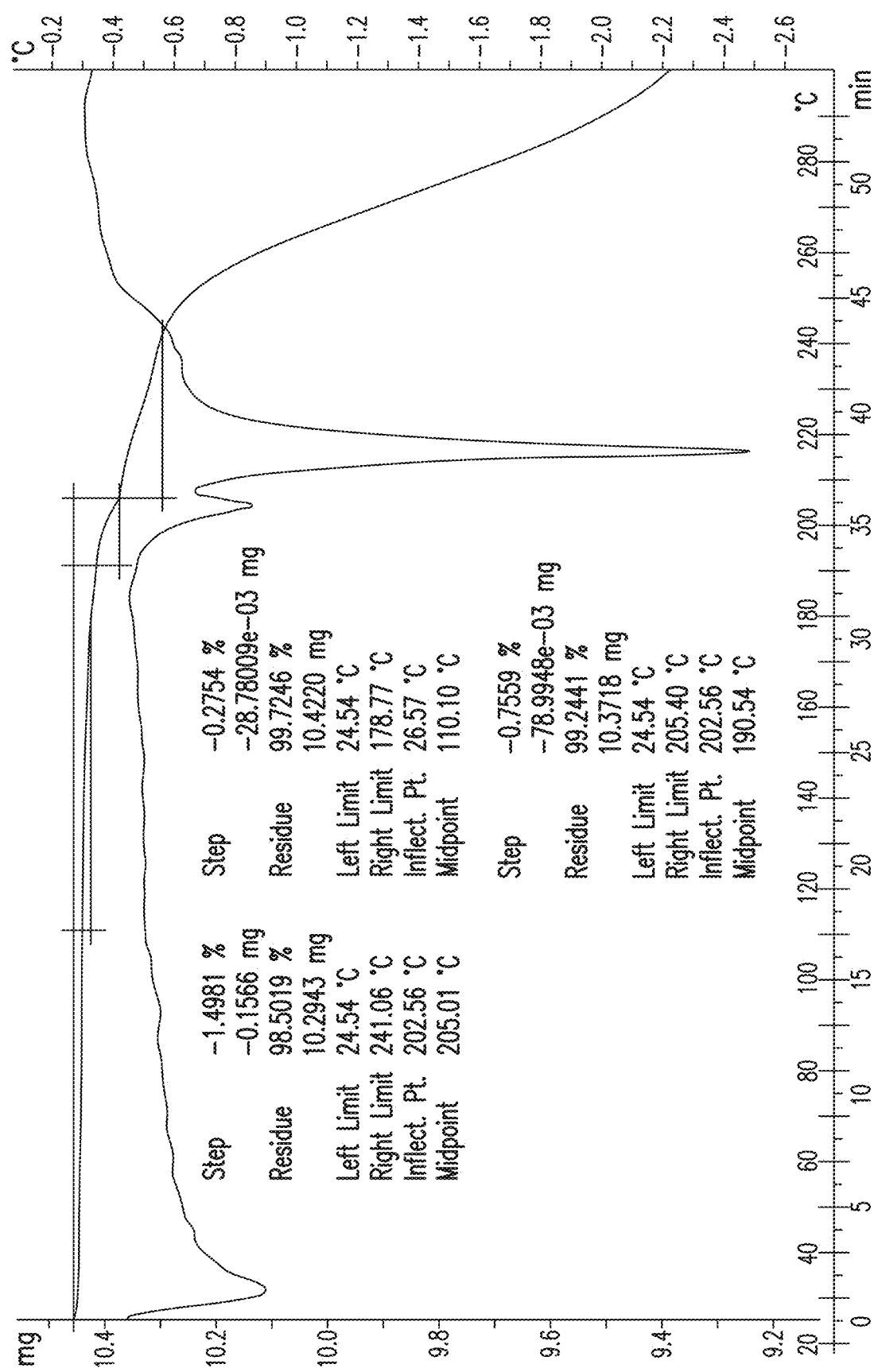
FIG. 8. Illustrates the TGA with SDTA curve of Form A showing a weight loss of approximately 0.28% w/w up to the first melting endotherm.

TGA (FIG. 8) with SDTA curve shows a similar curve as DSC with two endotherms and only 0.28% w/w weight loss up to the first melting endotherm. The increasing weight loss around melting points indicated thermal degradation.

Scale-Up Procedure.

Removal of solvates can require repetition of the given procedure. 200 mg starting material was suspended in acetone (1 mL) and the suspension stirred for 48 h. The suspension was filtered and the solid dried in vacuum.

Form B.

Figure 10:
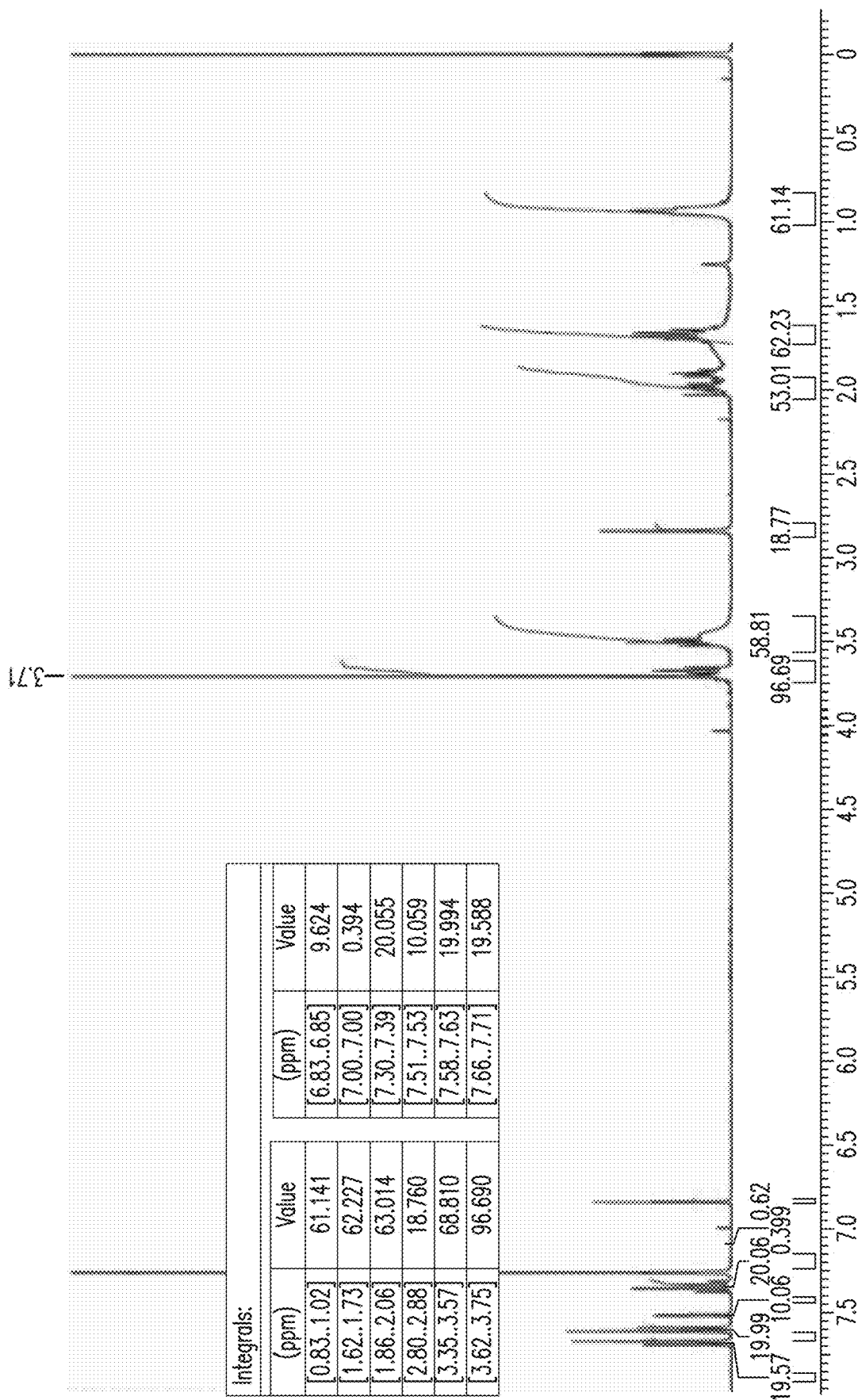
FIG. 10. Illustrates the ¹H NMR of form B (Table 1 experiment A1_10) showing at 3.7 ppm 2 protons from compound and 8 protons from dioxane.

Form B was obtained from tested screening experiments and from slurry in 1,4-dioxane and evaporation from 1,4-dioxane. Form B is a 1,4-dioxane solvate as confirmed by NMR (FIG. 10), which shows 1 eq of 1,4-dioxane.

Figure 9B:
FIG. 9B illustrates a microscopy picture of Form B taken without polarization. The bar indicates approximately 250 µm.
Figure 9A:
FIG. 9A illustrates a microscopy picture of Form B (Table 1 experiment A1_10) taken with crossed polarization filters.

Form B was nicely crystalline under the microscope (FIGS. 9A and 9B) but does not appear to have a clear crystal habit. XRPD of Form B (FIG. 43) shows good intensity of reflexes which can be at least partially come from nicely crystalline material. NMR showed approximately one equivalent of dioxane in the solid isolated from the evaporation experiment (Table 1, A1_10).

Figure 12:
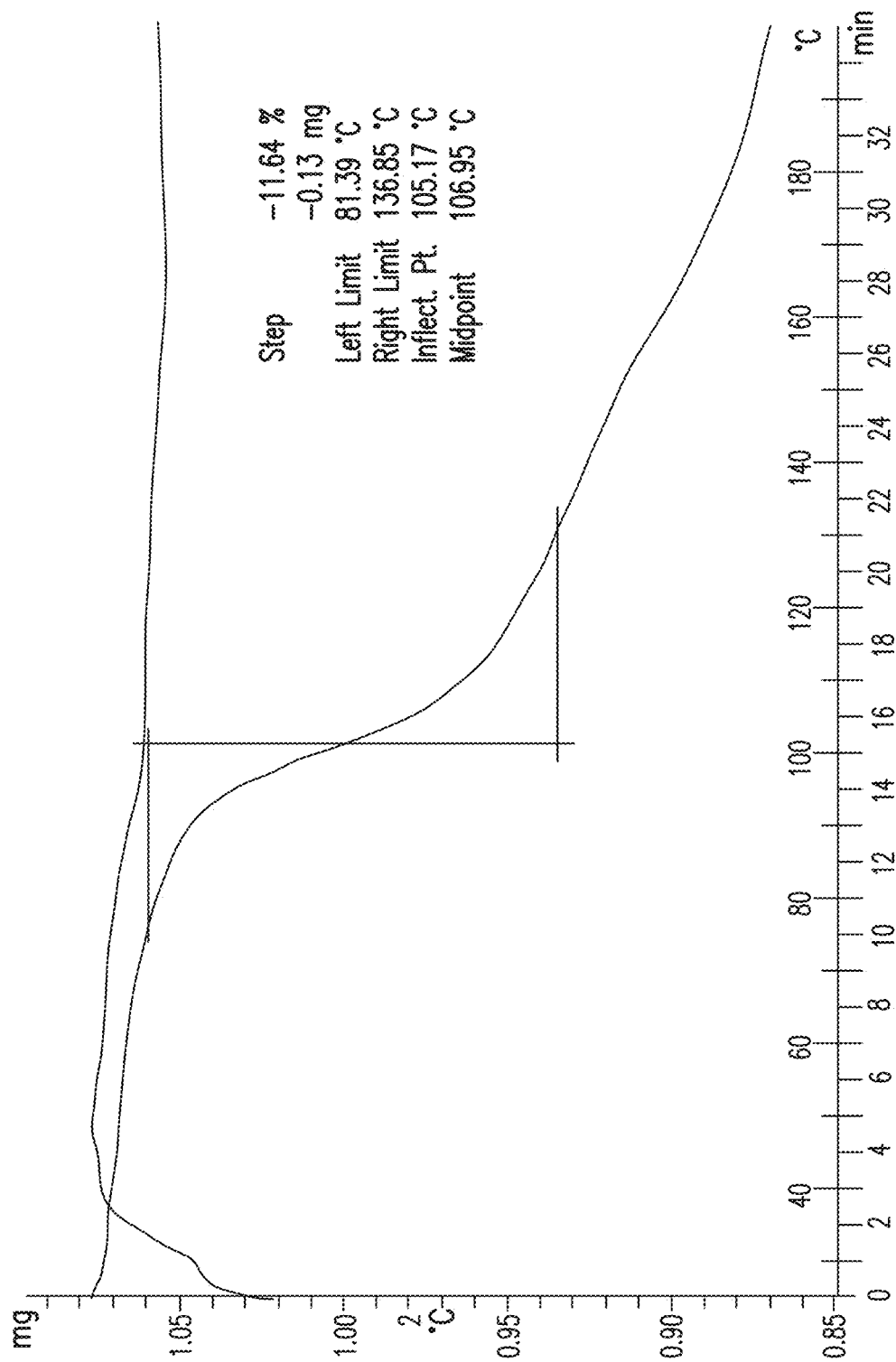
FIG. 12. Illustrates the TGA with SDTA curve of form B (Table 1 experiment A1_10) showing a weight loss of about 10% w/w around 100° C. and steady weight loss after this first step.

DSC (FIG. 11) showed an endotherm around 100° C. that corresponds to dioxane evaporation. The corresponding weight drop can be observed in TGA (FIG. 12). The second endotherm in DSC around does not appear to correspond to an event in TGA. The weight loss necessary for 1 eq of dioxane (about 16% w/w) was only reached around 180° C. but the SDTA curve does not show the lower nor the higher endotherm observed in DSC. Without being bound by any particular theory, the second endotherm may correspond to remaining solvent released during melt of the partially desolvated solid.

Scale-Up Procedure.

80 mg starting material was dissolved in 1,4-dioxane (12 mL) at 65° C. The solution was cooled to 25° C. and the solvent was slowly (ca. 6 h) evaporated by a constant stream of nitrogen until a dry solid is obtained.

Form C.

Figure 13:
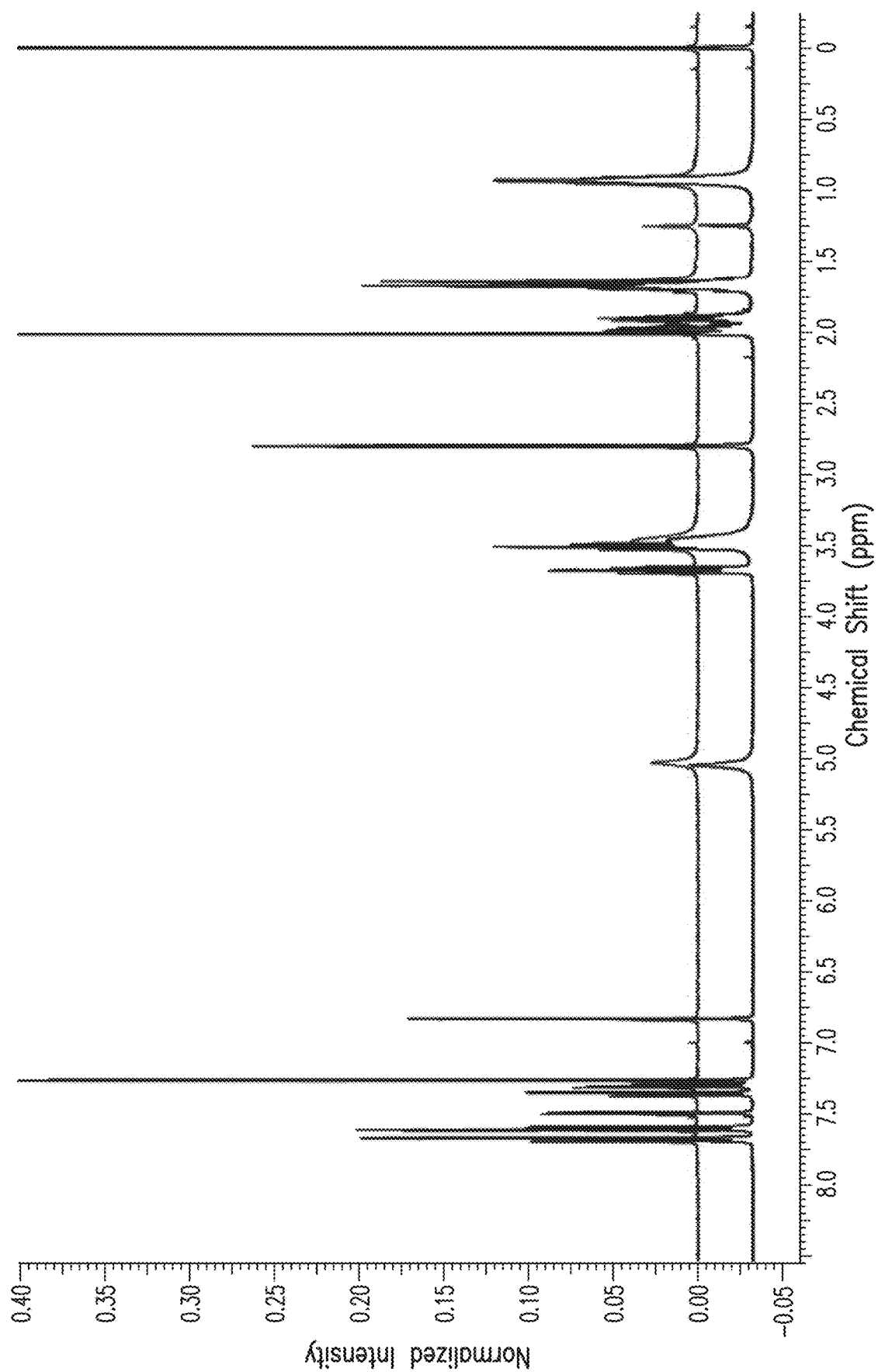
FIG. 13. Illustrates the ¹H NMR overlay of material after ACN slurry (bottom, ca. 0.9 eq) and after drying off ACN (bottom) and crude 3 (top).

Initially Form C was found present in experiment C3-1—likely in a pure form. After drying-out acetonitrile (FIG. 13: ACN at 2.02 ppm, confirmed by spiking ACN as signal was expected at 2.10 ppm) from material showing this pattern a new pattern could be observed where many reflexes almost vanished (the reflexes present in Form J).

Several attempts were undertaken to generate Form C. Slurries in ACN (up to 5 days) provided Form A. A prolonged slurry (2 weeks) afforded a mixture of Form C and J.

Figure 14:
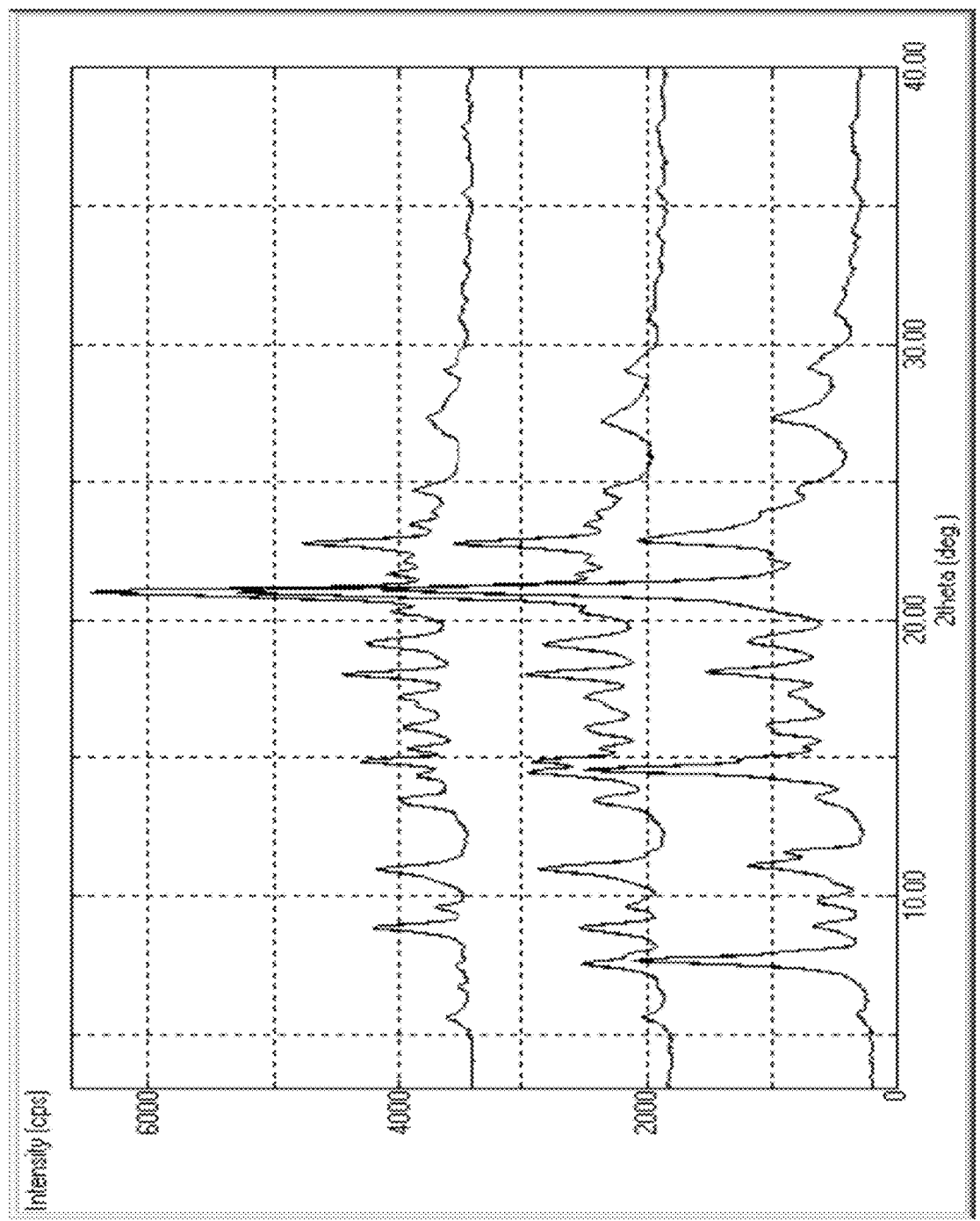
FIG. 14. Illustrates the overlay of isolated material: top: completely dried (form C, crude 3#1), middle: gently dried (crude 2#1) and wet cake (bottom, crude 1#1).

The material from the screening as well as the scale-up experiment contained ACN in the solid (FIG. 13) but could be dried under vacuum at ambient temperature. The wet cake (paste: crude 1#1), the gently dried cake (crude 2#1) and the completely dried cake (crude 3#1) were also checked by XRPD (FIG. 14): The reflexes of Form J are vanishing (see e.g., at 7.5 2theta). The screening sample A3_1 (evaporation from acetonitrile) converted to Form A during drying.

Figure 15:
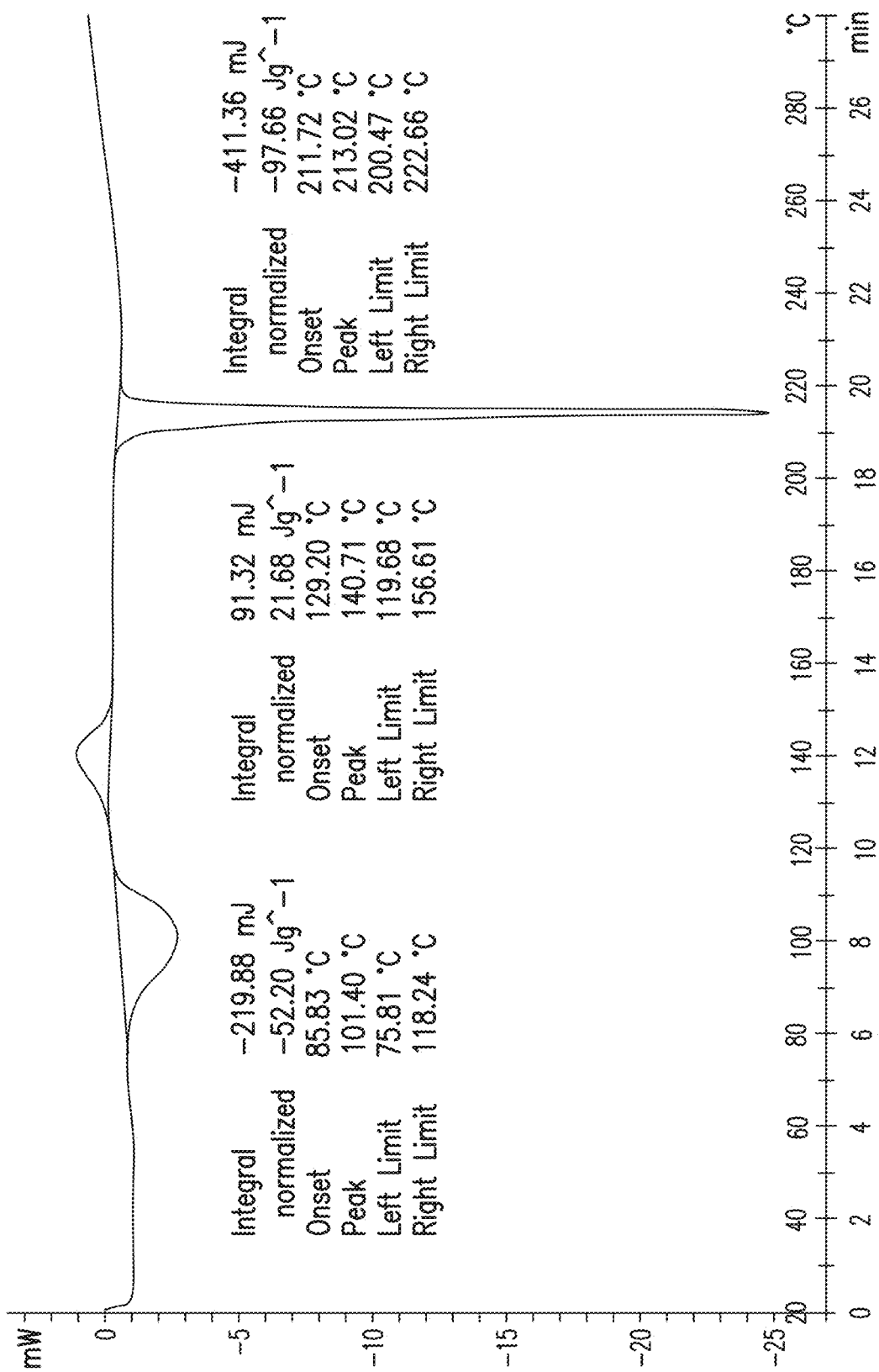
FIG. 15. Illustrates the DSC of form C/J mixture (crude 2#1) containing approximately 0.9 eq ACN which causes an endotherm at about 100° C.

DSC before drying the Form C/J mixture (FIG. 15) showed an endotherm around 100° C. that corresponds to ACN release and Form conversion and the dried Form mixture showing Form C (FIG. 16) was very similar to Form J.

Scale-Up Procedure.

The following approach was used to generate Form C. 200 mg starting material (Form A/G mixture) was suspended in ACN and intensively stirred for 15 days. The suspension was filtered and the solid dried in vacuum (max. vacuum, ambient temperature) to give Form C.

Form D.

Form D was isolated from the screening experiments, using dichloromethane as solvent. The slurry and quick cooling experiment but not the evaporation experiment led to Form D. Thus Form D was likely a (weak) solvate as weak vacuum during drying led to complete desolvation. XRPD (FIG. 45) of Form D is not well resolved with relatively broad reflexes. Additionally either an amorphous halo appears to be present or due to low sample amount the measurement does show high background noise.

Figure 18:
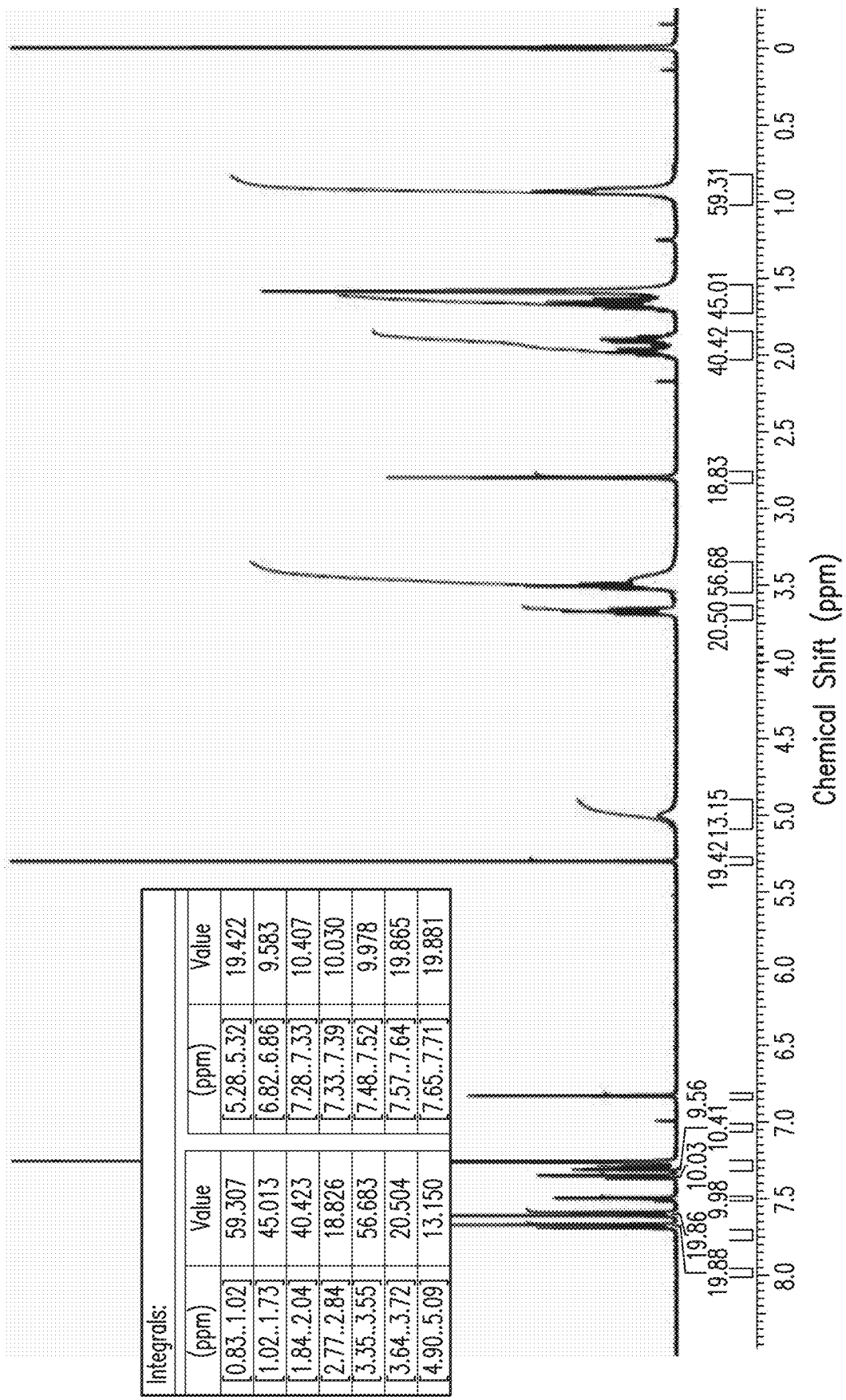
FIG. 18. Illustrates the ¹H NMR of Form D.
Figure 20:
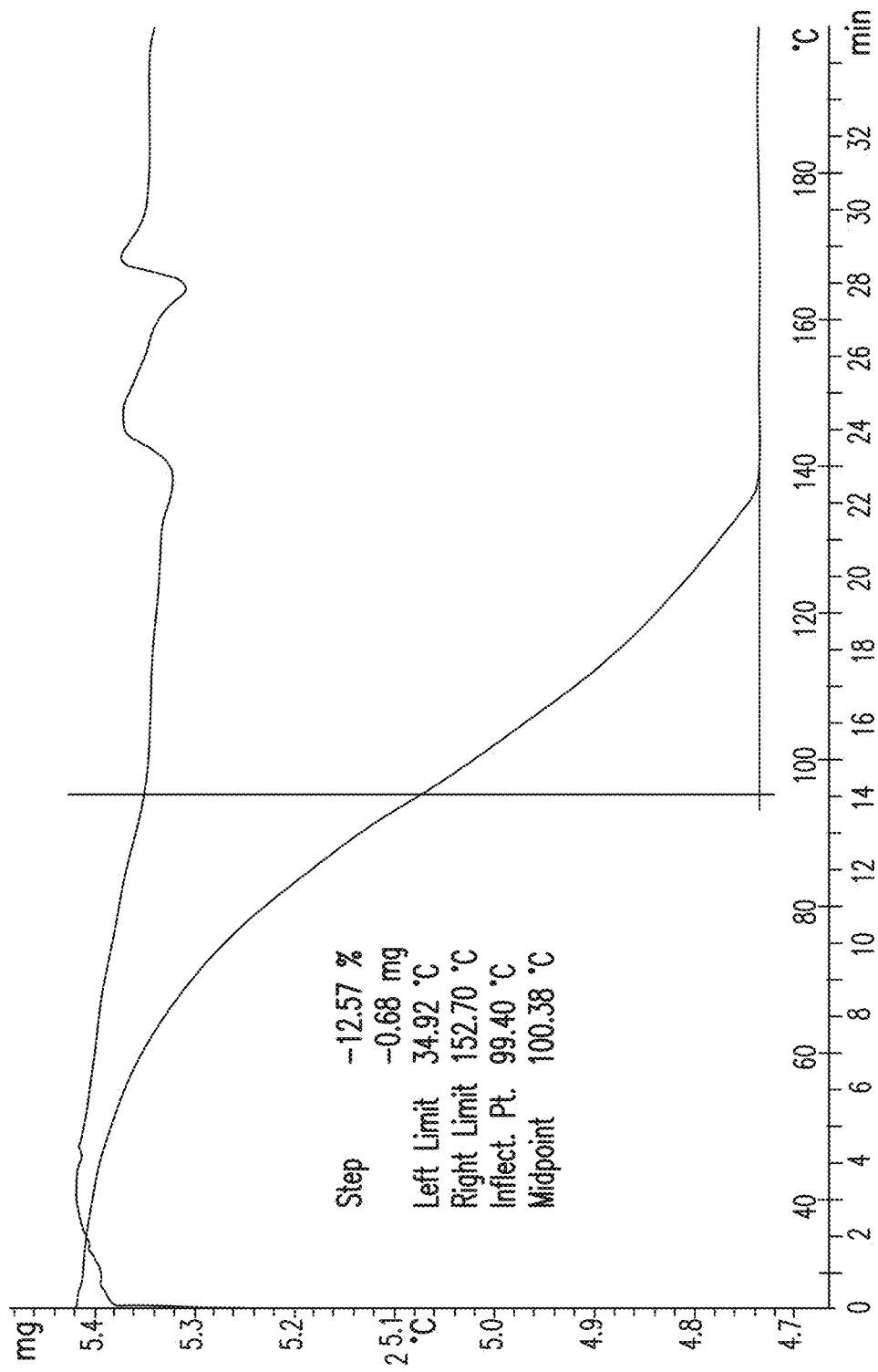
FIG. 20. Illustrates the TGA with SDTA curve of form D (Table 3 experiment C3_2) showing a weight loss up to 150° C. of about 13% w/w (mono solvate would correspond to approximately 16% w/w).

NMR (FIG. 18) showed one equivalent of dichloromethane at 5.3 ppm. DSC (FIG. 19) and TGA (FIG. 20) correspond when it comes to weight loss and the related endothermicity. Although not integrated in DSC prior to the first endothermic event a steady endotherm can be observed. After a first endotherm/exotherm a second smaller one can be observed leading to a melting point likely corresponding to Form G.

Scale-Up Procedure.

50 mg starting material was suspended in dichloromethane (0.3 mL) and the suspension was stirred for 5 d. The suspension was filtered and the solid gently dried in vacuum.

Form E.

Form E was observed from evaporation from chlorobenzene. The scale-up experiments (evaporation from chlorobenzene leading to Form G, slurry in chlorobenzene led to Form A (even wet solid). A seeded crystallization in chlorobenzene (targeted to deliver Form G) led to Form G with only traces of Form E.

Figure 21A:
FIG. 21A illustrates the microscopy picture of form E (Table 1 experiment A1_5) showing needle-like crystals using crossed polarization filters.
Figure 21B:
FIG. 21B illustrates the microscopy picture of form E (Table 1 experiment A1_5) showing needle-like crystals without polarization. The bar indicates approximately 250 µm.

As the screening sample contained chlorobenzene in liquid form (smell and visually confirmed) thermal analysis as TGA/DSC were not performed. Also no NMR data was collected as residual solvent and solvated chlorobenzene could not be distinguished. Form E showed needle-like crystals under the microscope (FIGS. 21A and 21B) and XRPD has narrow reflexes (FIG. 46).

The remaining screening sample was dried in vacuum (ambient temperature) and the resulting solid was checked by XRPD and showed conversion to Form G. Hence Form E is a chlorobenzene solvate.

Form F.

Figure 22A:
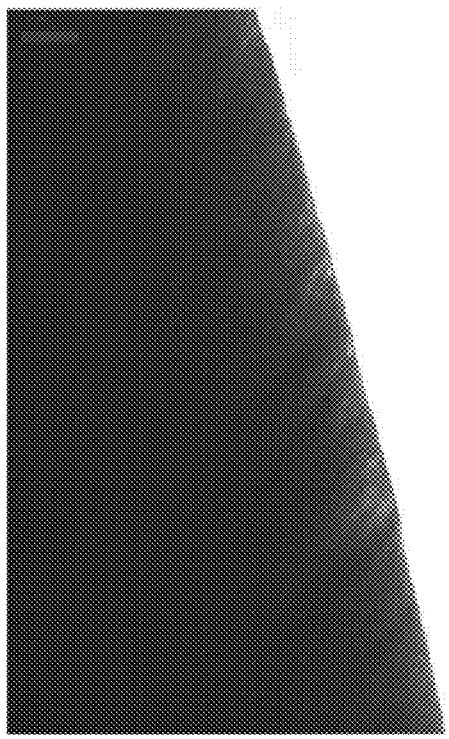
FIG. 22A illustrates the microscopy picture of form F (Table 1 experiment A1_6) showing the border of the solidified oil with crossed polarization filters.
Figure 22B:
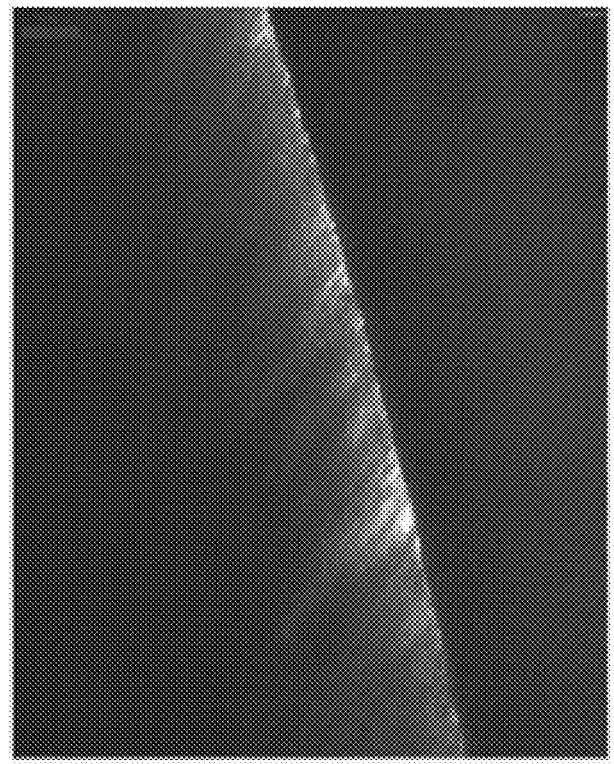
FIG. 22B illustrates the microscopy picture of form F (Table 1 experiment A1_6) showing the border of the solidified oil without polarization. The bar indicates approximately 250 µm.
Figure 23:
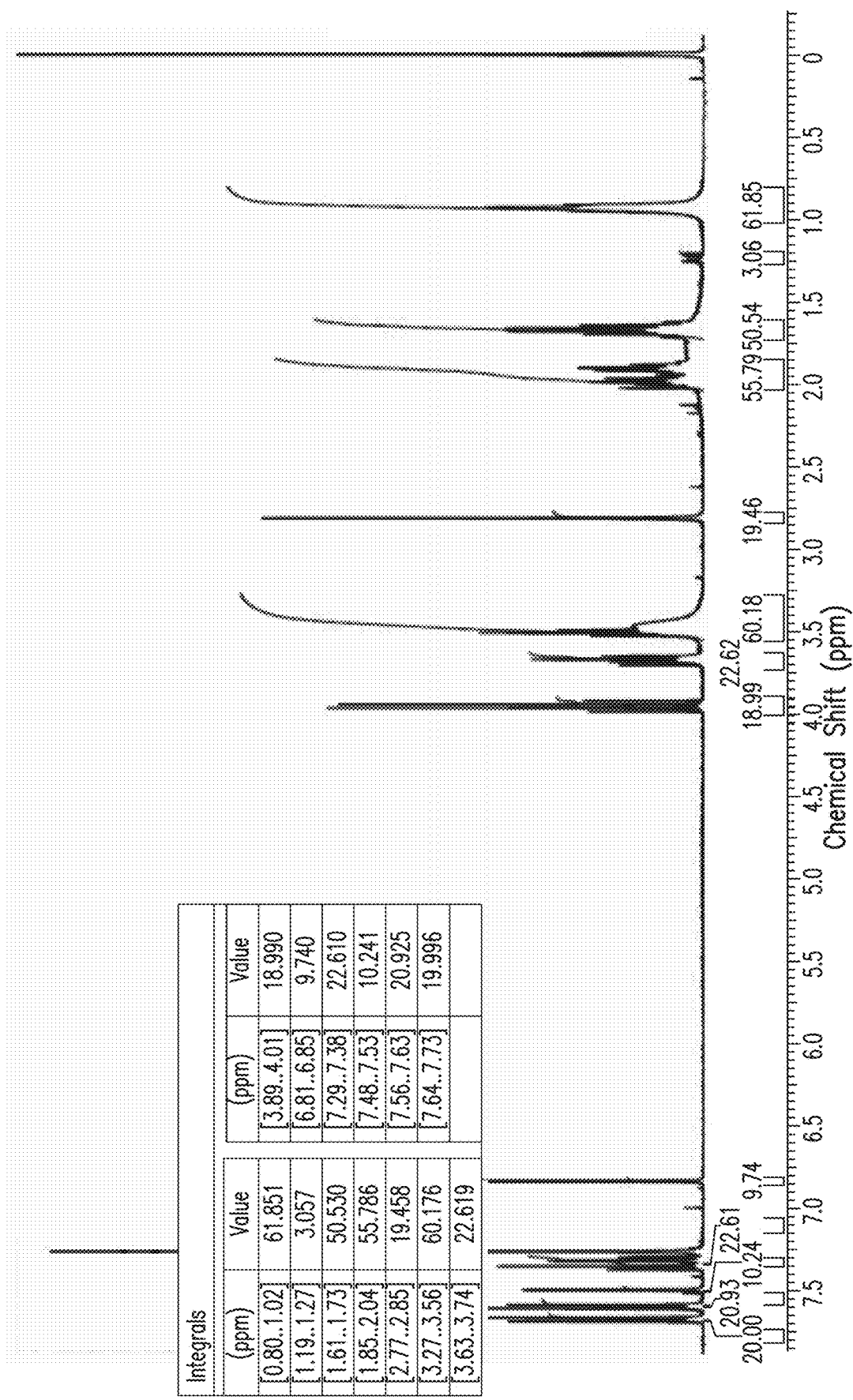
FIG. 23. Illustrates the ¹H NMR of form F.

Form F was obtained from evaporation from trifluoroethanol. The material formed a solidified oil and no crystal habit could be determined (FIGS. 22A and 22B). NMR (FIG. 23) revealed about 0.95 eq of trifluoroethanol (3.95 ppm) and XRPD (FIG. 47) showed a crystalline material with not well resolved reflexes. Without being bound by any particular theory, this may arise from non-ideal crystallization out of an oil/resin with residual amorphous/resin-like residue in the material.

Figure 25:
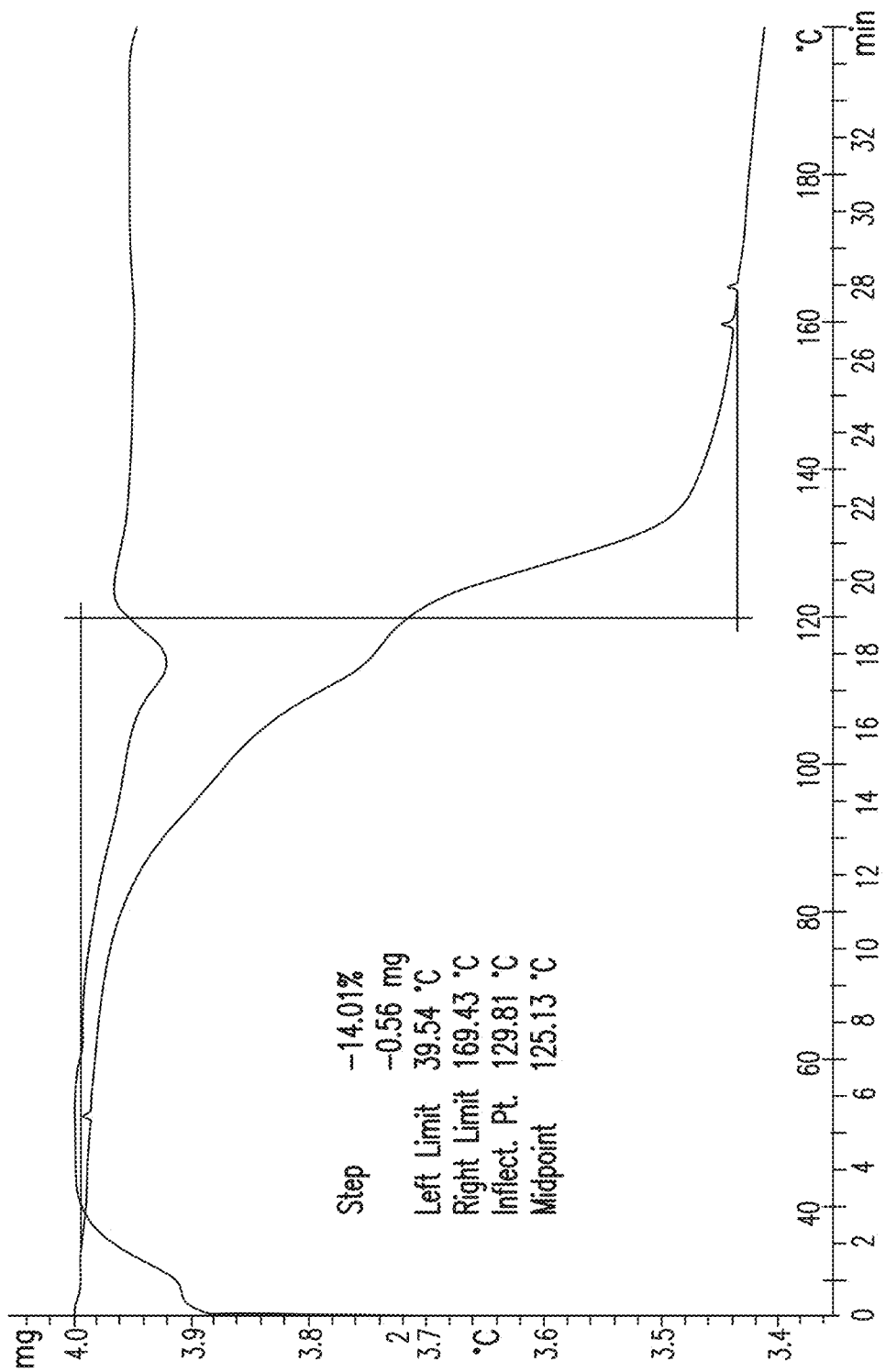
FIG. 25. Illustrates the TGA with SDTA curve of form F (Table 1 experiment A1_6) showing a weight loss up to 160° C. of about 14% w/w (mono solvate would correspond to approximately 18% w/w).
Figure 26B:
FIG. 26B illustrates the microscopy pictures of form G showing the needle forming form G with crossed polarization filters.
Figure 26D:
FIG. 26D illustrates the microscopy pictures of form G showing the needle forming form G without polarization.
Figure 26A:
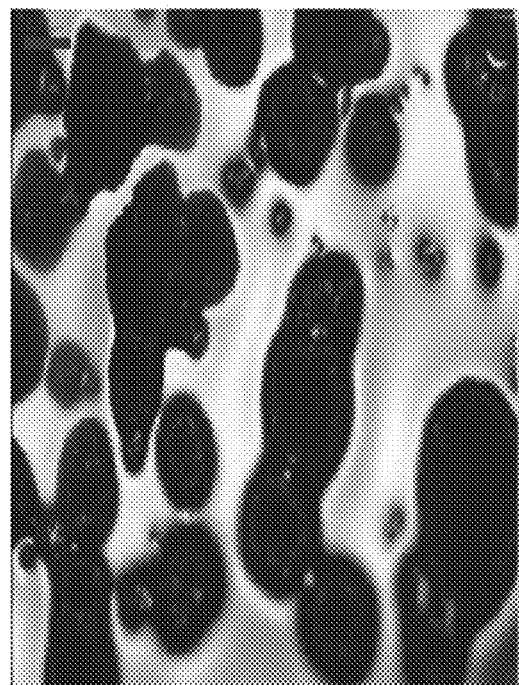
FIG. 26A illustrates the microscopy pictures of form G (Table 1 experiment A2_1, A2_10) showing hedgehog-like crystal agglomerates with crossed polarization filters.
Figure 26C:
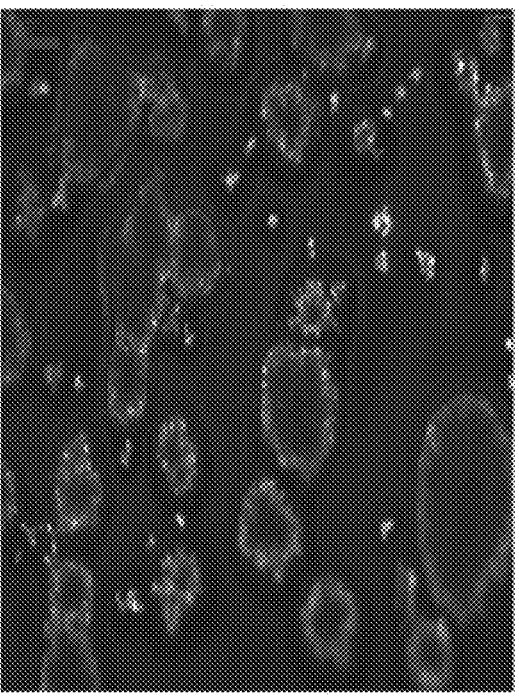
FIG. 26C illustrates the microscopy pictures of form G showing hedgehog-like crystal agglomerates without polarization. The red bar indicates about 250 µm.

DSC (FIG. 24) and TGA (FIG. 25) confirmed that Form F contained a large amount of trifluoroethanol. Although TGA indicated that less than 1 eq (about 0.8 eq) trifluoroethanol was released, without being bound by any particular theory, this could be because of the sample desolvating partially before starting the measurement or because the solvent is not completely released from the melt.

Form F is likely a mono trifluoroethanol solvate. Evaporation of a trifluoroethanol solution also yields Form I.

Form G.

Form G was present in the starting material used for the screening. It occurred in many experiments during the screening phase. The conversion to Form A in the slurry screening in most solvents showed that Form G was less stable at 25° C. in comparison to Form A. Remaining Form A/G mixes indicated that a certain level of solubility appeared necessary to improve form conversion. Form G has a needle-like habit (FIGS. 26A, 26B, 26C, and 26D) with a high tendency to form agglomerates.

Figure 27:
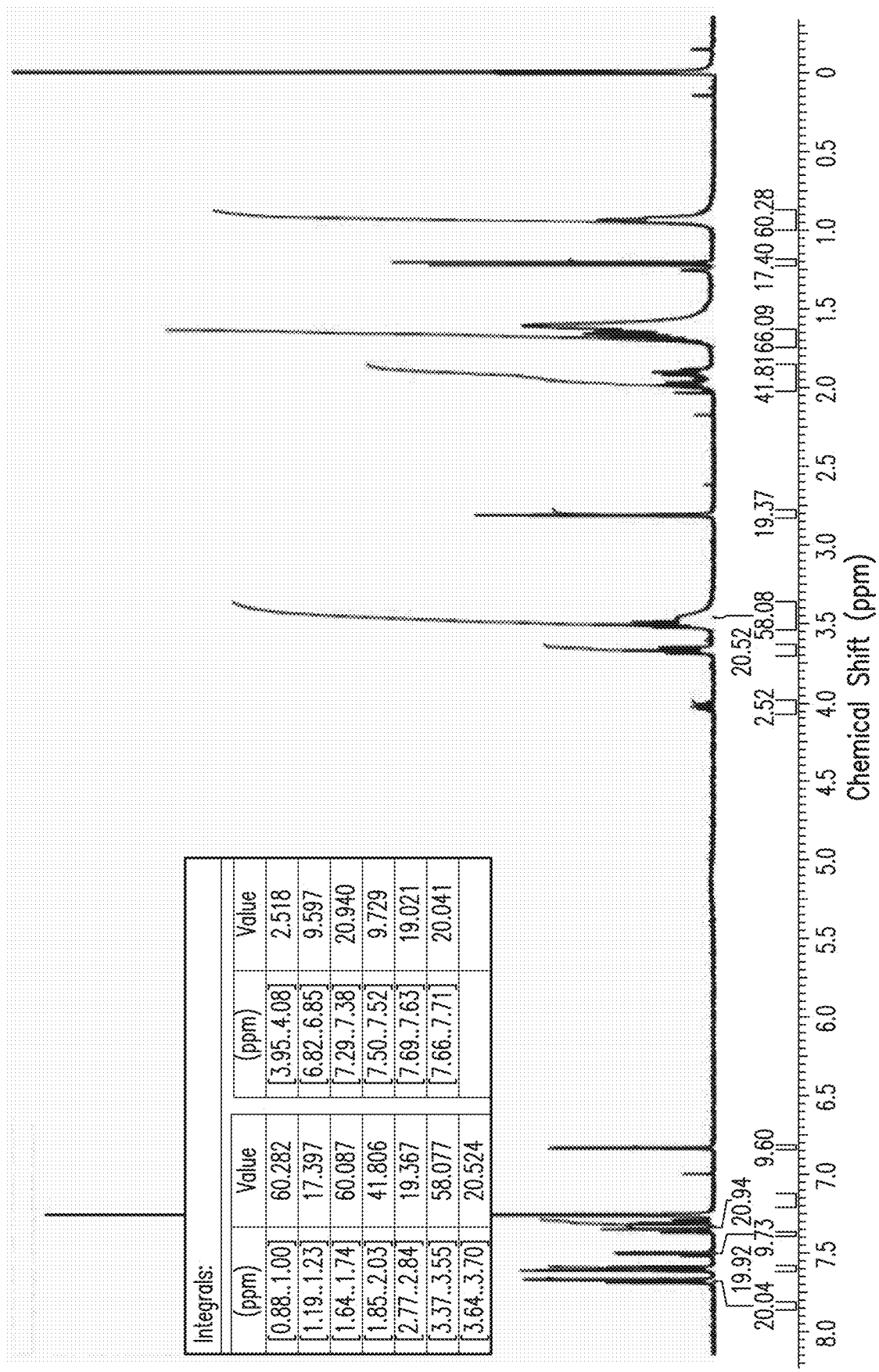
FIG. 27. Illustrates the ¹H NMR of form G.

NMR (FIG. 27) showed approximately 0.25 equivalents of isopropanol, but Form G is not likely an isopropanol solvate. It was also isolated from different solvents. During scale-up experiments from isopropanol Karl-Fischer titration was also performed and 0.5% w/w water found (approximately 0.1 eq).

Although XRPD (FIG. 47) does not appear to have well separated reflexes, no pattern was observed that seemed to have less amorphous halo.

Figure 29:
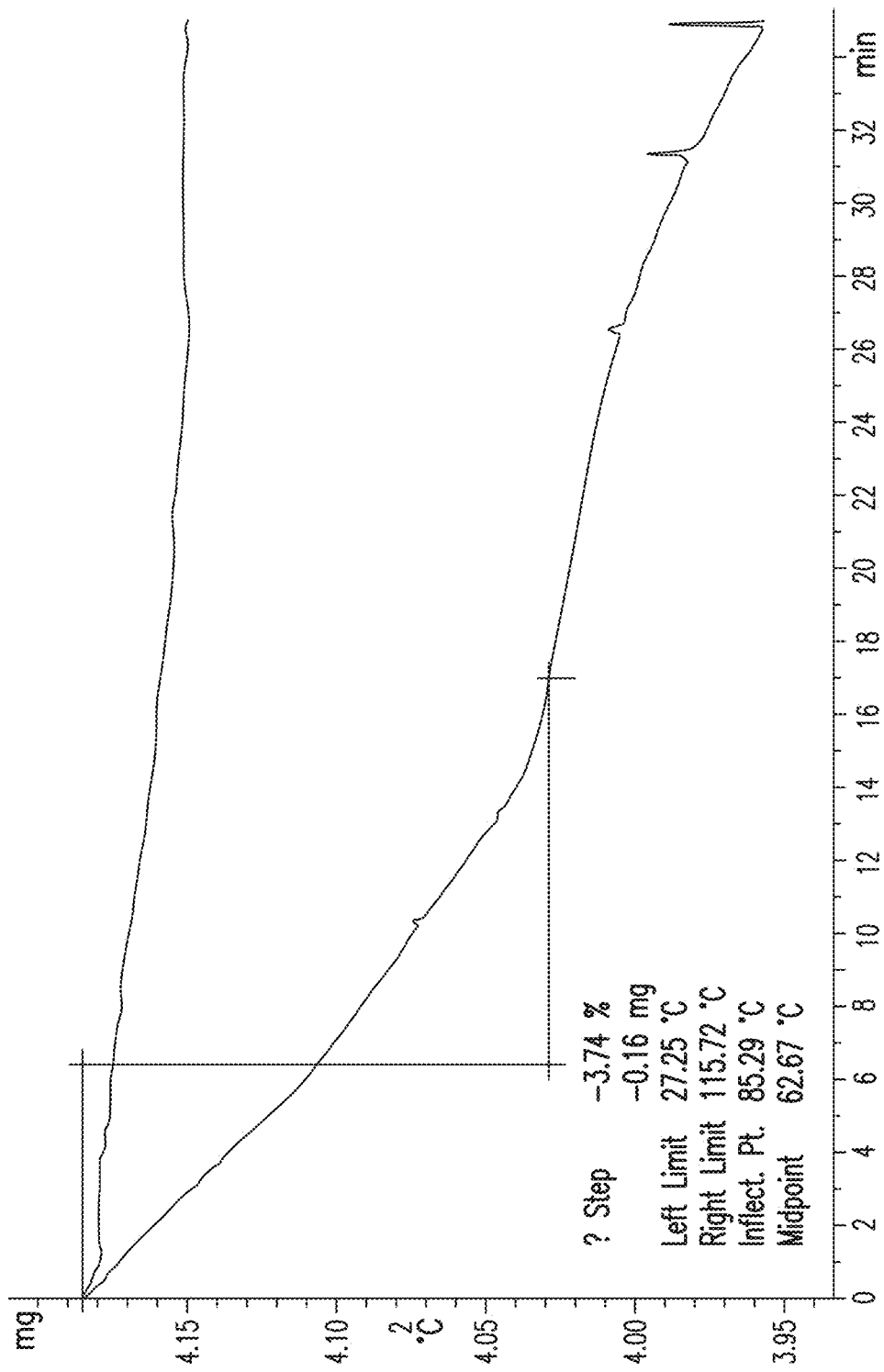
FIG. 29. Illustrates the TGA with SDTA curve of form G (Table 1 experiment A2_1) showing a weight loss up to 120° C. (18 min) of about 3.7% w/w which corresponds about the expected amount of isopropanol in the sample.

Thermal analysis of Form G showed only one melting point (peak: 209.5° C.) in DSC (FIG. 28) but no clear corresponding solvent loss in TGA (FIG. 29). Several attempts were undertaken to generate Form G in slightly larger scale. Form G was obtained by evaporating a solution in chlorobenzene at ambient temperature. Evaporation, in some instances, afforded a mixture of Form G and Form E. On 270 mg scale a solution in isopropanol afforded Form A after evaporation. A seeded crystallization from isopropanol with subsequent evaporation of the solvent led to Form G in slightly larger scale.

Scale-Up Procedure.

100 mg starting material was dissolved in isopropanol (4 mL) at 65° C. and filtered over a syringe filter. The solution was cooled to 25° C. and the solvent was slowly (ca. 6 h) evaporated by a constant stream of nitrogen until a dry solid is obtained.

Form H.

Figure 30A:
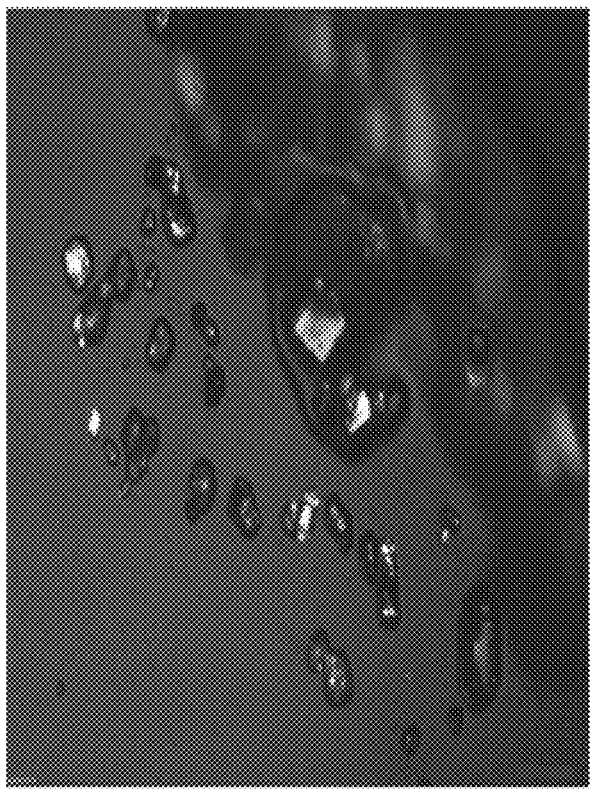
FIG. 30A illustrates the microscopy picture of form H (Table 2 experiment B2_2) showing crystals with bipyramidal habit with crossed polarization filters.
Figure 30B:
FIG. 30B illustrates the microscopy picture of form H (Table 2 experiment B2_2) showing crystals with bipyramidal habit without polarization. The bar indicates about 250 µm.

Form H was observed in cooling experiments, including THF and isopropanol as solvents. The crystal habit of Form F appears to be bipyramidal (FIGS. 30A and 30B). Form H can be obtained as a mixture with Form A in a seeded scale-up experiment from THF. Drying off the remaining THF at ambient temperature led to pure Form A. Although this could also have been a solid transformation of a non-solvated form into another form, Form A is more stable than Form H. The drying of the Form A/H mixture was performed 5 days after the scale-up run which would correspond to a quick form transition in case not the drying would have caused form transition.

Figure 31:
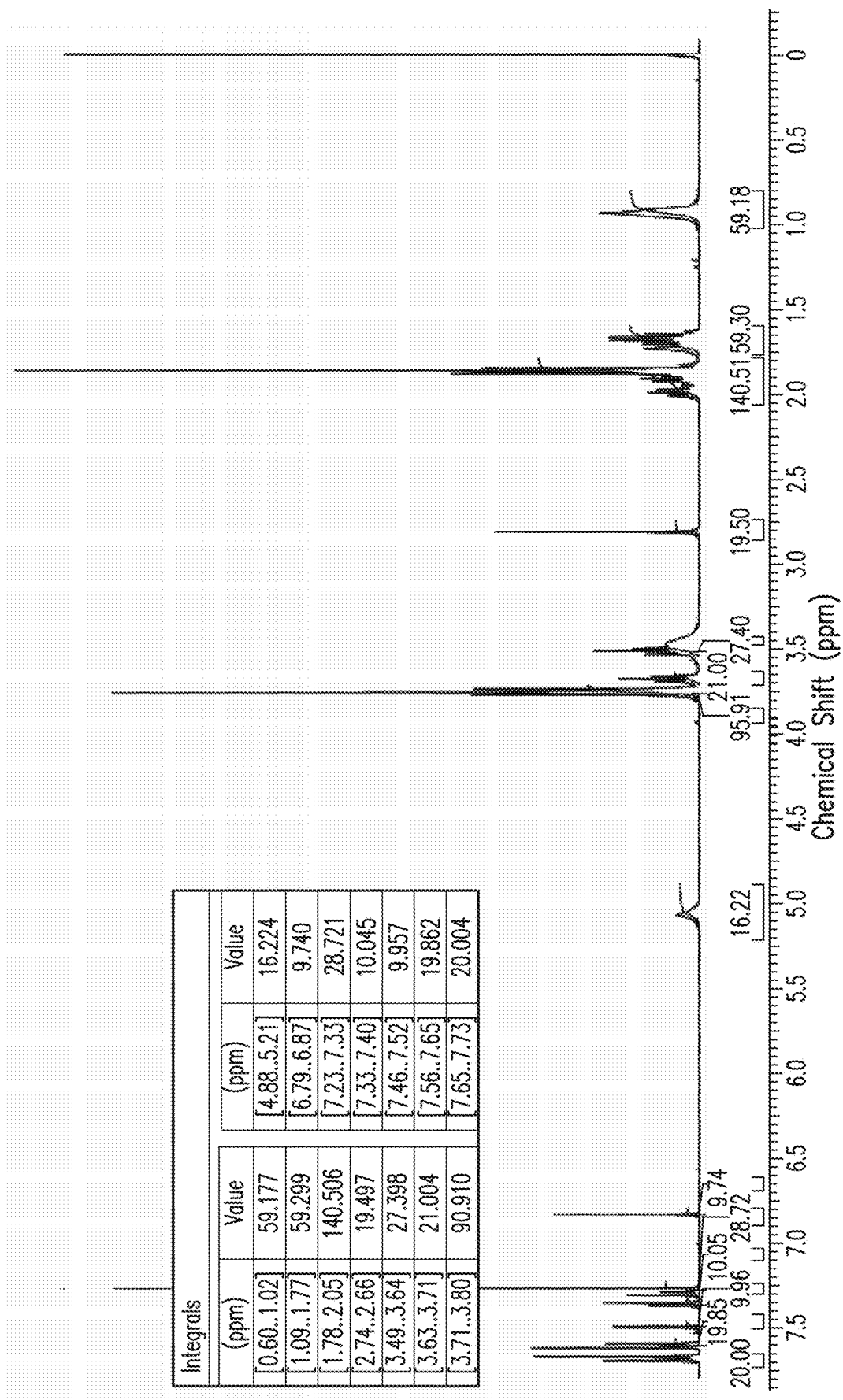
FIG. 31. Illustrates the ¹H NMR of form G.
Figure 32A:
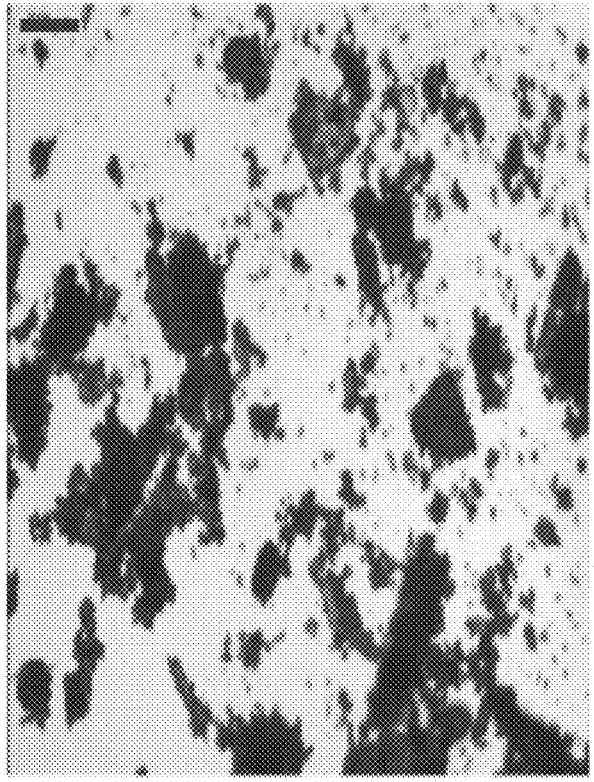
FIG. 32A illustrates the microscopy picture of form I showing crystals without defined habit (after breaking the block) with crossed polarization filters.
Figure 32B:
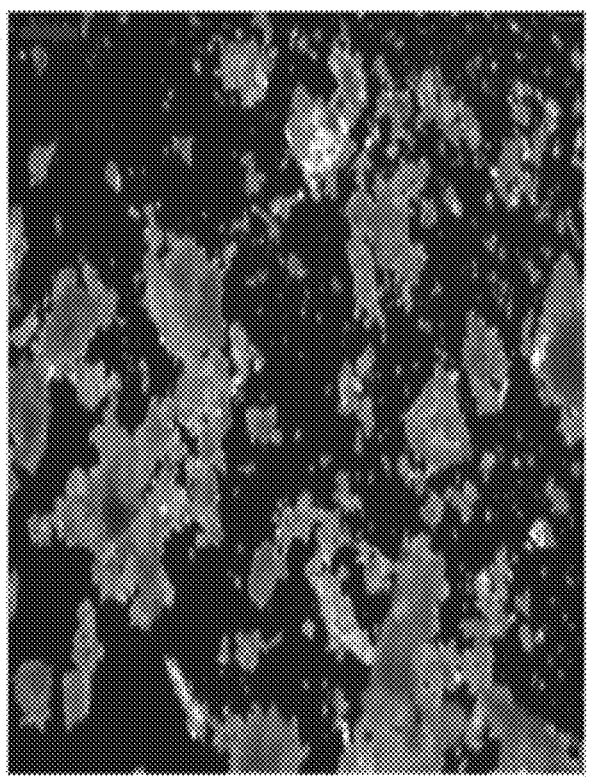
FIG. 32B illustrates the microscopy picture of form I showing crystals without defined habit (after breaking the block) with crossed polarization filters without polarization. The bar indicates about 250 µm.

Pure Form H was available in small amounts from the THF screening experiment (B2_2). Collected NMR data (FIG. 31) indicated a THF content of approximately 2.4 equivalents. Form H cannot be a THF solvate because it was obtained from isopropanol as well. The detected THF either showed wet solid or that form H is a channel solvate also possible with isopropanol.

Scale-Up Procedure.

50 mg starting material is dissolved in 4 mL THF at 65° C. The solution is cooled to room temperature. and the solvent evaporated with a constant stream of vacuum at 850 mbar during >3 days.

A mixture of Form A and Form H was tested by XRPD after drying off residual THF and only Form A was visible. Without being bound by any particular theory, this may occur by a desolvation effect of a potential channel solvate or by form conversion of a kinetic form to the stable Form A.

Form I.

Figure 33:
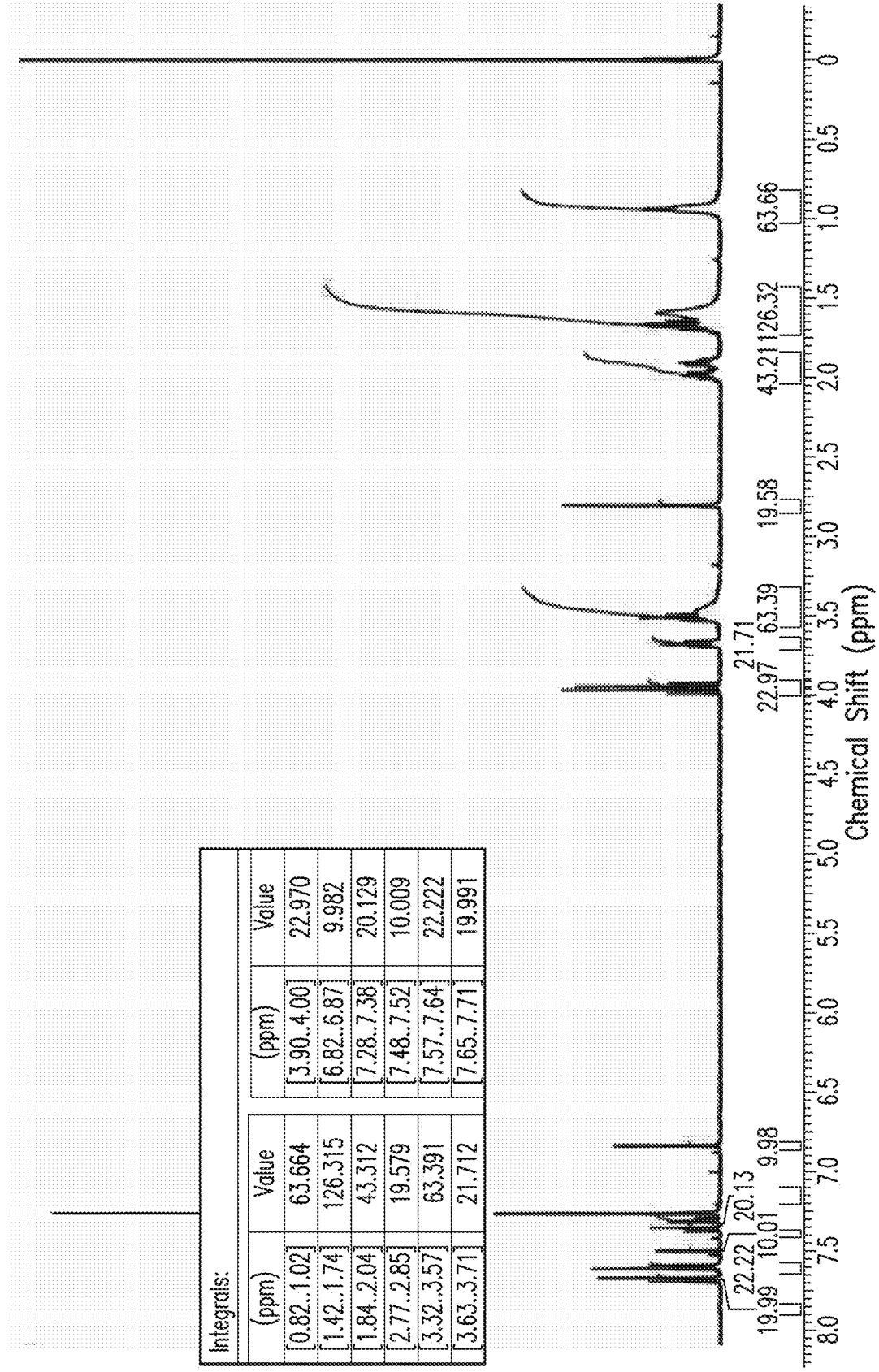
FIG. 33. Illustrates the ¹H NMR of form I.
Figure 34:
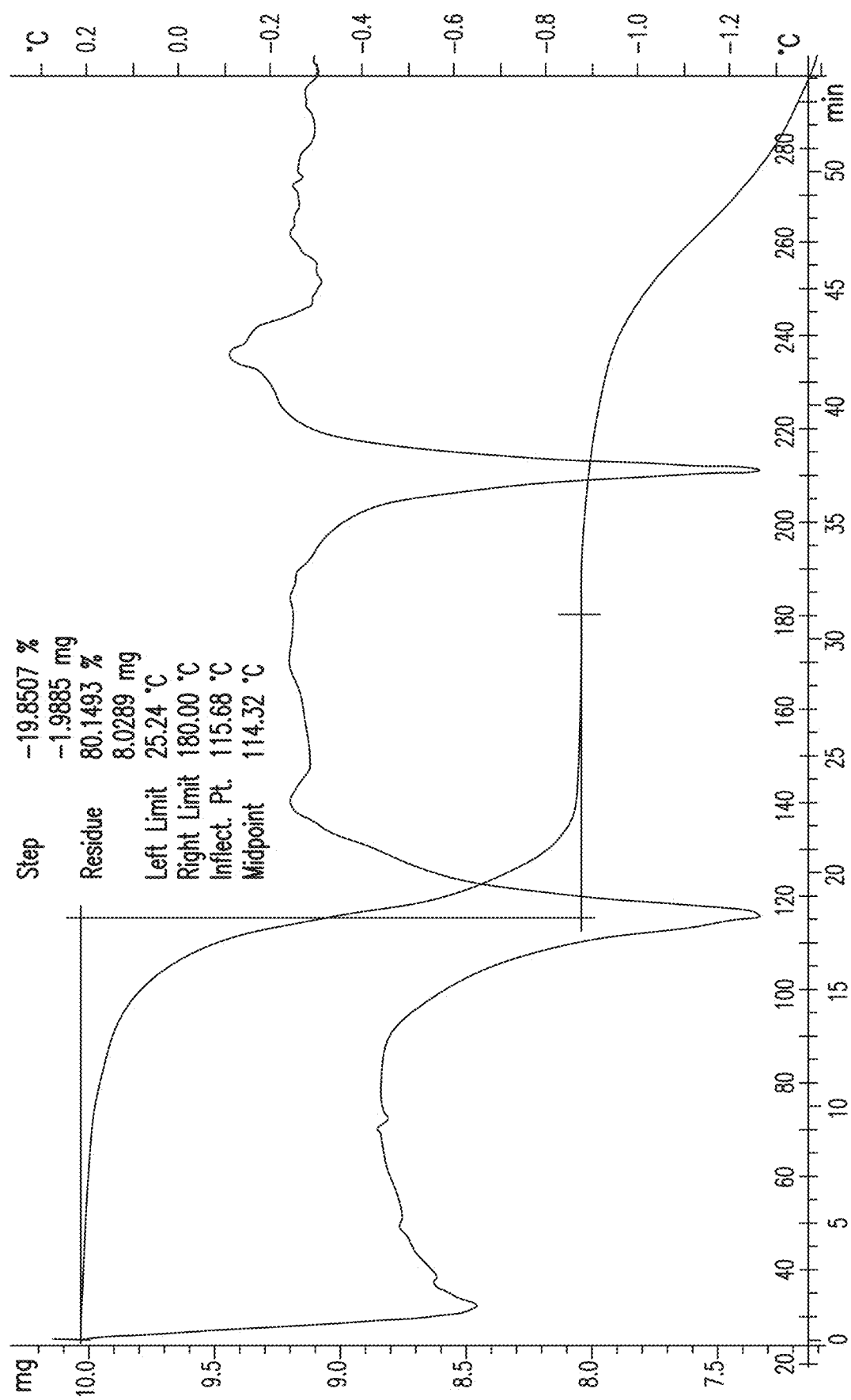
FIG. 34. Illustrates the DSC with SDTA curve of form I with an endotherm at around 110° C. corresponding to a weight loss of 19.8% w/w.

Form I is likely a mono trifluoroethanol solvate as indicated by NMR (FIG. 33) showing about 1.1 eq trifluoroethanol and by TGA (FIG. 34). Insufficient material hindered additional analytics.

Form J.

The exotherm event in DSC (FIG. 36) indicated a monotropic correlation to Form G which itself has an enantiotropic relation to Form A. Hence Form J is less stable than Form A.

Example 4: Form Stability Analysis

Stability of Forms.

For the examination of the stability of different forms the solvates were excluded. The identified solvates are:

Form B (1,4-dioxane)

Form D (dichloromethane)

Form E (chlorobenzene)

Form F (trifluoroethanol)

Form I (trifluoroethanol)

The following forms were regarded as potential real forms or could not be identified as real solvates:

Form A (obtained in most screening experiments)

Form C (Initially Form C appeared to be an ACN solvate)

Form G (present in starting material)

Form H (potentially a channel solvate)

Form J

Solubility data for Forms A and G was collected to determine the most stable form from 0 to 60° C. The screening results confirmed Form A to be more stable than Form G at 20° C. As the most stable form also shows the lowest solubility, data for both forms was collected in ethanol and MEK (at least two solvents were selected to exclude any solvent/solvate effect).

TABLE 4

Solubility of Forms A and G in [mg/mL] after 40 min stirring.

| ° C. | A/EtOH | G/EtOH | A/MEK | G/MEK |
|---|---|---|---|---|
| 0 | 4.7 | 7.6 | 1.8 | 2.6 |
| 22 | 11.7 | 15.8 | 2.4 | 3.1 |
| 60 | 32.1 | 36.9 | 3.7 | 4.6 |

As form conversions tend to happen faster at elevated temperature at 60° C., slurries were performed for the starting material used for the screening (A/G mixture) during 18 h at 60° C. Both isolated samples showed pure Form A. The difference in solubility at 60° C. was much smaller than at 0° C., and indicates either less difference in stability or quicker form conversion at elevated temperature.

Form J.

Forms J and C were identified as potential non-solvates and their stability was investigated. Form J could be eliminated as stable form because, in part, the DSC (FIG. 36) indicated an exothermic form conversion around 140° C. This leads to a form melting at 210° C., which likely represents Form G and therefore represents a monotropic relation.

Form C.

Form C was obtained by drying a Form C/J mixture. The XRPD pattern appeared to contain traces of reflexes of Form J. Slurries of Form C seeded with Form A (15% w/w) in ethanol and acetone were performed during 18 h. The resulting solid was pure Form A. This also confirmed the exothermic event observed in DSC (FIG. 16) which indicated a monotropic relation to the form formed in DSC around 130° C. (melting point 210° C., which, as described herein, is likely Form G).

Solubility of Form A.

To develop a Form A crystallization, a series of solubility data points was collected (Table 5). An amount of up to 15 mg was suspended in 150 μL and the mixture stirred for 2 days. Solubility was then determined by HPLC or by calculation if a solution was observed.

TABLE 5

Solubility of Form A at 20° C. and 40° C.

| | | Solubility [mg/mL] | | |
|---|---|---|---|---|
| Entry | Solvent | 20° C. | 40° C. | Comment |
| 1 | DMSO | 21.6 | 50.9 | — |
| 2 | DMSO/TBME 1:1 v/v | 17.2 | 44.6 | — |
| 3 | DMSO/EtOAc 1:1 v/v | 15.0 | 36.9 | — |
| 4 | THF | 3.7 | 7.7 | — |
| 5 | THF/H$_2$O 8:2 v/v | 38.6 | >100 | Clear solution with 10 vol of solvent mix @ 40° C. |
| 6 | THF/EtOH 8:2 v/v | 13.4 | 27.8 | — |
| 7 | 2-PrOH | 4.5 | 9.59 | — |
| 8 | EtOH | 8.50 | 24.0 | — |
| 9 | Toluene/MeOH 7:3 v/v | >100 | >100 | Clear solution with 10 vol of solvent mix. |
| 10 | Toluene/2-PrOH 7:3 v/v | 23.1 | 45.9 | — |

Example 5: Summary

The screening successfully identified 10 forms of which the following 5 forms were identified as solvates:
Form B (1,4-dioxane)
Form D (dichloromethane)
Form E (chlorobenzene)
Form F (trifluoroethanol)
Form I (trifluoroethanol)
The solubility and concurrent slurry experiments identified Form A as the most stable form from 0° C. to 60° C. Form G is an enantiotropic form of Form A (higher melting point than Form A but at least above melting point of Form A more stable than Form A) but the transition temperature is not known.

Form C and J are less stable than Forms A and G and are in a monotropic correlation to Forms A and G.

While examples of certain particular embodiments are provided herein, it will be apparent to those skilled in the art that various changes and modifications may be made. Such modifications are also intended to fall within the scope of the appended claims.

TABLE 6

XRPD of form A

| Sample: | 200672169 | File: | 305130227_CLGR14 | Date: Aug. 7, 2014 09:26:55 | Operator: BBO |
|---|---|---|---|---|---|
| Comment: | Rough | Memo: | Si Sample Holder: | No grinding | |
| Method: | 2$^{nd}$ differential | Typical width: | 0.250 deg. | Min. height: 150.00 cps | |

Intensity (cps)
2theta (deg.)

| Peak no. | 2theta | Flex Width | d-value | Intensity | I/Io |
|---|---|---|---|---|---|
| 1 | 8.660 | 0.188 | 10.2023 | 441 | 13 |
| 2 | 9.220 | 0.212 | 9.5838 | 798 | 23 |
| 3 | 10.800 | 0.188 | 8.1850 | 366 | 11 |
| 4 | 11.940 | 0.212 | 7.4060 | 2467 | 70 |
| 5 | 14.780 | 0.212 | 5.9887 | 615 | 18 |
| 6 | 15.520 | 0.188 | 5.7048 | 775 | 22 |
| 7 | 16.380 | 0.259 | 5.4071 | 3573 | 100 |
| 8 | 17.680 | 0.212 | 5.0124 | 617 | 18 |
| 9 | 18.520 | 0.188 | 4.7869 | 1159 | 33 |
| 10 | 19.900 | 0.235 | 4.4579 | 324 | 10 |
| 11 | 20.400 | 0.212 | 4.3498 | 826 | 24 |
| 12 | 20.920 | 0.165 | 4.2428 | 1646 | 47 |
| 13 | 21.240 | 0.188 | 4.1796 | 2303 | 65 |
| 14 | 21.680 | 0.212 | 4.0958 | 1183 | 34 |
| 15 | 22.040 | 0.141 | 4.0297 | 533 | 15 |

TABLE 6-continued

| | XRPD of form A | | | | |
|---|---|---|---|---|---|
| 16 | 22.360 | 0.212 | 3.9727 | 850 | 24 |
| 17 | 22.980 | 0.235 | 3.8669 | 1130 | 32 |
| 18 | 23.520 | 0.188 | 3.7794 | 1316 | 37 |
| 19 | 24.160 | 0.400 | 3.6807 | 1746 | 49 |
| 20 | 25.880 | 0.212 | 3.4398 | 1062 | 30 |
| 21 | 26.320 | 0.212 | 3.3833 | 512 | 15 |
| 22 | 26.820 | 0.141 | 3.3214 | 596 | 17 |
| 23 | 27.000 | 0.212 | 3.2996 | 832 | 24 |
| 24 | 27.380 | 0.235 | 3.2547 | 1147 | 33 |
| 25 | 28.040 | 0.259 | 3.1796 | 644 | 19 |
| 26 | 28.900 | 0.212 | 3.0869 | 430 | 13 |
| 27 | 29.840 | 0.212 | 2.9917 | 363 | 11 |

TABLE 7

XRPD of form B

| Sample: | 200664731 | File: | 305062109_CLGR14 | Date: Jun. 26, 2014 16:36:13 Operator: BBO |
|---|---|---|---|---|
| Comment: | Rough | Memo: | Si Sample Holder: | slightly grinded |
| Method: | $2^{nd}$ differential | Typical width: | 0.250 deg. | Min. height: 150.00 cps |

Intensity (cps)
2theta (deg.)

| Peak no. | 2theta | Flex Width | d-value | Intensity | I/Io |
|---|---|---|---|---|---|
| 1 | 6.260 | 0.188 | 14.1073 | 363 | 3 |
| 2 | 10.740 | 0.188 | 8.2306 | 2449 | 15 |
| 3 | 12.540 | 0.188 | 7.0530 | 394 | 3 |
| 4 | 15.240 | 0.165 | 5.8090 | 1061 | 7 |
| 5 | 15.520 | 0.235 | 5.7048 | 1876 | 12 |
| 6 | 15.860 | 0.165 | 5.5832 | 745 | 5 |
| 7 | 16.580 | 0.141 | 5.3424 | 357 | 3 |
| 8 | 17.480 | 0.165 | 5.0693 | 17038 | 100 |
| 9 | 18.160 | 0.188 | 4.8810 | 605 | 4 |
| 10 | 18.580 | 0.188 | 4.7716 | 1419 | 9 |
| 11 | 18.900 | 0.141 | 4.6915 | 626 | 4 |
| 12 | 19.700 | 0.188 | 4.5027 | 3186 | 19 |
| 13 | 20.900 | 0.212 | 4.2468 | 1290 | 8 |
| 14 | 21.820 | 0.212 | 4.1070 | 2602 | 16 |
| 15 | 22.260 | 0.259 | 3.9904 | 521 | 4 |
| 16 | 22.680 | 0.165 | 3.9174 | 428 | 3 |
| 17 | 23.080 | 0.212 | 3.8504 | 410 | 3 |
| 18 | 24.220 | 0.188 | 3.6717 | 2377 | 14 |
| 19 | 24.740 | 0.188 | 3.5957 | 1053 | 7 |
| 20 | 24.920 | 0.141 | 3.5701 | 814 | 5 |
| 21 | 25.320 | 0.188 | 3.5146 | 528 | 4 |
| 22 | 25.960 | 0.212 | 3.4294 | 876 | 6 |
| 23 | 26.380 | 0.188 | 3.3757 | 1505 | 9 |
| 24 | 27.180 | 0.282 | 3.2782 | 443 | 3 |
| 25 | 29.380 | 0.212 | 3.0375 | 650 | 4 |
| 26 | 30.020 | 0.235 | 2.9742 | 444 | 3 |
| 27 | 30.880 | 0.188 | 2.8933 | 356 | 3 |
| 28 | 31.820 | 0.141 | 2.8099 | 422 | 3 |
| 29 | 35.400 | 0.188 | 2.5335 | 736 | 5 |

TABLE 8

XRPD of form C

| Sample: | 200676519 | File: | 305164001_CLGR14 | Date: Aug. 27, 2014 16:51:03 Operator: BBO |
| --- | --- | --- | --- | --- |
| Comment: | Rough | Memo: | Si Sample Holder: | slightly ground |
| Method: | 2nd differential | Typical width: | 0.250 deg. | Min. height: 150.00 cps |

Intensity (cps)
2theta (deg.)

| Peak no. | 2theta | Flex Width | d-value | Intensity | I/Io |
| --- | --- | --- | --- | --- | --- |
| 1 | 5.620 | 0.329 | 15.7123 | 428 | 13 |
| 2 | 8.860 | 0.282 | 9.9724 | 990 | 31 |
| 3 | 9.580 | 0.212 | 9.2245 | 508 | 16 |
| 4 | 10.600 | 0.141 | 8.3390 | 542 | 17 |
| 5 | 10.980 | 0.353 | 8.0513 | 1002 | 31 |
| 6 | 13.500 | 0.471 | 6.5536 | 791 | 25 |
| 7 | 14.360 | 0.235 | 6.1829 | 664 | 21 |
| 8 | 14.880 | 0.282 | 5.9487 | 1101 | 34 |
| 9 | 15.340 | 0.282 | 5.7713 | 722 | 22 |
| 10 | 16.100 | 0.306 | 5.5006 | 769 | 24 |
| 11 | 16.860 | 0.188 | 5.2543 | 653 | 20 |
| 12 | 17.200 | 0.306 | 5.1512 | 779 | 24 |
| 13 | 18.020 | 0.235 | 4.9186 | 1283 | 39 |
| 14 | 19.120 | 0.447 | 4.6380 | 1070 | 33 |
| 15 | 20.320 | 0.282 | 4.3667 | 858 | 27 |
| 16 | 21.020 | 0.259 | 4.2229 | 3292 | 100 |
| 17 | 21.680 | 0.212 | 4.0958 | 893 | 28 |
| 18 | 22.120 | 0.306 | 4.0153 | 759 | 24 |
| 19 | 22.800 | 0.282 | 3.8971 | 1556 | 48 |
| 20 | 23.480 | 0.259 | 3.7857 | 706 | 22 |
| 21 | 23.940 | 0.188 | 3.7140 | 641 | 17 |
| 22 | 24.700 | 0.238 | 3.6014 | 687 | 21 |
| 23 | 26.760 | 0.141 | 3.3287 | 448 | 14 |
| 24 | 27.320 | 0.353 | 3.2817 | 569 | 18 |
| 25 | 29.060 | 0.212 | 3.0702 | 441 | 14 |

TABLE 9

XRPD of form D
2theta (deg.)

| Peak no. | 2theta | Flex Width | d-value | Intensity | I/Io |
| --- | --- | --- | --- | --- | --- |
| 1 | 6.560 | 0.282 | 13.4628 | 342 | 23 |
| 2 | 7.760 | 0.259 | 11.3834 | 752 | 50 |
| 3 | 9.020 | 0.329 | 9.7959 | 481 | 32 |
| 4 | 10.560 | 0.235 | 8.3705 | 389 | 26 |
| 5 | 13.740 | 0.306 | 6.4396 | 437 | 29 |
| 6 | 14.700 | 0.212 | 6.0211 | 379 | 25 |
| 7 | 15.620 | 0.306 | 5.6685 | 1368 | 90 |
| 8 | 16.280 | 0.165 | 5.4401 | 491 | 33 |
| 9 | 17.100 | 0.329 | 5.1811 | 462 | 31 |
| 10 | 18.060 | 0.141 | 4.9078 | 582 | 39 |
| 11 | 18.220 | 0.494 | 4.8650 | 651 | 43 |
| 12 | 18.780 | 0.188 | 4.7212 | 464 | 31 |
| 13 | 19.080 | 0.141 | 4.6476 | 415 | 28 |
| 14 | 19.680 | 0.471 | 4.5073 | 654 | 44 |
| 15 | 20.680 | 0.188 | 4.2915 | 791 | 53 |
| 16 | 21.180 | 0.165 | 4.1913 | 646 | 43 |
| 17 | 22.040 | 0.353 | 4.0297 | 1521 | 100 |
| 18 | 22.520 | 0.259 | 3.9449 | 842 | 56 |
| 19 | 23.700 | 0.635 | 3.7511 | 1321 | 87 |
| 20 | 25.000 | 0.141 | 3.5589 | 470 | 31 |
| 21 | 26.640 | 0.235 | 8.3494 | 418 | 28 |
| 22 | 27.620 | 0.400 | 3.2269 | 439 | 29 |
| 23 | 28.700 | 0.188 | 3.1079 | 409 | 27 |

TABLE 10

XRPD of form E
2theta (deg.)

| Peak no. | 2theta | Flex Width | d-value | Intensity | I/Io |
| --- | --- | --- | --- | --- | --- |
| 1 | 5.380 | — | 16.4127 | 316 | 14 |
| 2 | 8.820 | 0.165 | 10.0176 | 2381 | 100 |
| 3 | 9.340 | 0.165 | 9.4610 | 729 | 31 |
| 4 | 12.100 | — | 7.3084 | 269 | 12 |
| 5 | 13.380 | 0.188 | 6.6120 | 491 | 21 |
| 6 | 13.820 | — | 6.4025 | 250 | 11 |
| 7 | 18.020 | 0.165 | 6.5278 | 391 | 17 |
| 8 | 16.480 | 0.165 | 5.3810 | 325 | 14 |
| 9 | 17.740 | 0.188 | 4.9958 | 954 | 41 |
| 10 | 18.320 | 0.306 | 4.8387 | 383 | 16 |
| 11 | 18.860 | 0.188 | 4.6768 | 448 | 19 |
| 12 | 19.480 | 0.188 | 4.5531 | 529 | 23 |
| 13 | 21.440 | 0.165 | 4.1411 | 938 | 40 |
| 14 | 22.240 | 0.188 | 3.9939 | 743 | 32 |
| 15 | 22.600 | 0.235 | 3.8311 | 744 | 32 |
| 16 | 22.920 | 0.141 | 3.8769 | 375 | 16 |
| 17 | 23.300 | 0.141 | 3.6145 | 405 | 18 |
| 18 | 23.540 | 0.235 | 3.7762 | 352 | 15 |
| 19 | 24.400 | 0.235 | 3.6450 | 761 | 32 |
| 20 | 26.160 | 0.188 | 3.4036 | 270 | 12 |
| 21 | 26.800 | 0.212 | 3.3238 | 554 | 24 |
| 22 | 27.820 | 0.188 | 3.2042 | 278 | 12 |
| 23 | 29.320 | — | 3.0436 | 150 | 7 |

TABLE 11

XRPD of form F
2theta (deg.)

| Peak no. | 2theta | Flex Width | d-value | Intensity | I/Io |
|---|---|---|---|---|---|
| 1 | 4.580 | 0.235 | 19.2776 | 3884 | 100 |
| 2 | 4.820 | 0.188 | 18.3182 | 3087 | 80 |
| 3 | 7.320 | 0.250 | 12.0668 | 388 | 11 |
| 4 | 8.060 | — | 10.9604 | 286 | 8 |
| 5 | 9.700 | 0.308 | 9.1106 | 442 | 12 |
| 6 | 11.020 | — | 8.0221 | 306 | 8 |
| 7 | 12.240 | — | 7.2251 | 383 | 10 |
| 8 | 13.840 | 0.282 | 6.3933 | 437 | 12 |
| 9 | 14.800 | 0.212 | 5.9806 | 505 | 14 |
| 10 | 15.320 | 0.353 | 5.7788 | 1158 | 30 |
| 11 | 16.060 | 0.329 | 5.5142 | 896 | 24 |
| 12 | 16.600 | 0.424 | 5.3360 | 1290 | 34 |
| 13 | 17.460 | 0.282 | 5.0750 | 553 | 15 |
| 14 | 17.900 | 0.165 | 4.9513 | 473 | 13 |
| 15 | 18.520 | 0.259 | 4.7889 | 681 | 18 |
| 16 | 18.060 | 0.282 | 4.6525 | 1483 | 39 |
| 17 | 19.820 | 0.235 | 4.5209 | 709 | 19 |
| 18 | 20.200 | 0.259 | 4.3924 | 630 | 17 |
| 19 | 20.820 | 0.282 | 4.2830 | 631 | 17 |
| 20 | 21.520 | 0.259 | 4.1259 | 613 | 14 |
| 21 | 22.180 | 0.212 | 4.0048 | 488 | 13 |
| 22 | 22.880 | 0.353 | 3.8838 | 1372 | 38 |
| 23 | 23.380 | 0.282 | 3.8017 | 774 | 21 |
| 24 | 24.040 | 0.308 | 3.6968 | 443 | 12 |
| 25 | 24.840 | 0.282 | 3.6100 | 732 | 19 |
| 26 | 25.160 | 0.259 | 3.5366 | 554 | 15 |
| 27 | 25.800 | 0.400 | 3.4503 | 555 | 15 |
| 28 | 27.460 | 0.212 | 3.2454 | 418 | 11 |
| 29 | 27.880 | 0.259 | 3.1974 | 452 | 12 |
| 30 | 31.880 | 0.235 | 2.8048 | 427 | 12 |

TABLE 12

XRPD of form G
2theta (deg.)

| Peak no. | 2theta | Flex Width | d-value | Intensity | I/Io |
|---|---|---|---|---|---|
| 1 | 9.360 | 0.212 | 9.4408 | 673 | 23 |
| 2 | 10.240 | 0.235 | 8.6314 | 387 | 13 |
| 3 | 11.340 | 0.308 | 7.7965 | 606 | 20 |
| 4 | 12.020 | 0.259 | 7.3569 | 1071 | 38 |
| 5 | 12.920 | 0.212 | 6.8464 | 564 | 20 |
| 6 | 13.380 | 0.235 | 6.6120 | 1097 | 37 |
| 7 | 14.720 | 0.259 | 6.0130 | 822 | 31 |
| 8 | 15.740 | 0.235 | 5.6255 | 1178 | 39 |
| 9 | 16.440 | 0.259 | 5.3875 | 3038 | 100 |
| 10 | 17.140 | 0.212 | 5.1691 | 591 | 20 |
| 11 | 17.660 | 0.168 | 6.0180 | 739 | 25 |
| 12 | 18.360 | 0.235 | 4.8282 | 2105 | 70 |
| 13 | 19.000 | 0.235 | 4.6670 | 951 | 32 |
| 14 | 19.520 | 0.235 | 4.5439 | 1152 | 38 |
| 15 | 20.100 | 0.235 | 4.4140 | 739 | 25 |
| 16 | 20.520 | 0.212 | 4.3248 | 706 | 24 |
| 17 | 21.460 | 0.235 | 4.1373 | 1378 | 48 |
| 18 | 21.840 | 0.165 | 4.0681 | 592 | 20 |
| 19 | 22.440 | 0.308 | 3.9588 | 2180 | 73 |
| 20 | 22.800 | 0.235 | 3.8971 | 1455 | 48 |
| 21 | 23.460 | 0.329 | 3.7889 | 1954 | 65 |
| 22 | 24.200 | 0.212 | 3.6747 | 1123 | 37 |
| 23 | 25.140 | 0.353 | 3.5994 | 947 | 32 |
| 24 | 25.880 | 0.212 | 3.4398 | 558 | 19 |
| 25 | 26.220 | 0.282 | 3.3960 | 932 | 31 |
| 26 | 28.660 | 0.165 | 3.3409 | 640 | 22 |
| 27 | 27.240 | 0.141 | 3.2711 | 507 | 17 |
| 28 | 28.540 | 0.212 | 3.1250 | 402 | 14 |
| 29 | 29.300 | 0.282 | 3.0456 | 542 | 18 |
| 30 | 33.820 | 0.259 | 2.6408 | 420 | 14 |

TABLE 13

XRPD of form H
2theta (deg.)

| Peak no. | 2theta | Flex Width | d-value | Intensity | I/Io |
|---|---|---|---|---|---|
| 1 | 6.340 | 0.188 | 13.9295 | 465 | 8 |
| 2 | 11.000 | 0.188 | 8.0387 | 6647 | 100 |
| 3 | 12.700 | 0.212 | 6.9645 | 589 | 9 |
| 4 | 15.260 | 0.165 | 5.8014 | 1720 | 26 |
| 5 | 15.560 | 0.188 | 5.6902 | 2914 | 44 |
| 6 | 15.940 | 0.188 | 5.5554 | 728 | 11 |
| 7 | 17.540 | 0.212 | 5.0521 | 3708 | 56 |
| 8 | 18.200 | 0.165 | 4.8703 | 724 | 11 |
| 9 | 18.560 | 0.165 | 4.7718 | 804 | 13 |
| 10 | 18.880 | 0.188 | 4.8964 | 1852 | 28 |
| 11 | 19.960 | 0.212 | 4.4447 | 5860 | 89 |
| 12 | 21.080 | 0.141 | 4.2110 | 1011 | 16 |
| 13 | 22.080 | 0.188 | 4.0225 | 4809 | 73 |
| 14 | 22.580 | 0.141 | 3.9345 | 546 | 9 |
| 15 | 23.220 | 0.212 | 3.8275 | 594 | 9 |
| 16 | 24.180 | 0.165 | 3.6777 | 538 | 9 |
| 17 | 24.620 | 0.188 | 3.6129 | 3194 | 49 |
| 18 | 25.060 | 0.235 | 3.6505 | 1521 | 23 |
| 19 | 25.660 | 0.259 | 3.4688 | 541 | 9 |
| 20 | 26.520 | 0.188 | 3.3582 | 1249 | 19 |
| 21 | 27.040 | 0.188 | 3.2948 | 647 | 9 |
| 22 | 27.460 | 0.212 | 3.2454 | 600 | 10 |
| 23 | 29.480 | 0.235 | 3.0274 | 417 | 7 |
| 24 | 29.880 | 0.188 | 2.9878 | 887 | 14 |
| 25 | 30.500 | 0.188 | 2.9285 | 758 | 12 |
| 26 | 31.480 | 0.212 | 2.8395 | 449 | 7 |
| 27 | 32.180 | 0.188 | 2.7793 | 417 | 7 |
| 28 | 34.620 | 0.188 | 2.5888 | 427 | 7 |
| 29 | 35.120 | 0.235 | 2.5531 | 381 | 6 |
| 30 | 35.580 | 0.212 | 2.5211 | 548 | 9 |

TABLE 14

XRPD of form I
2theta (deg.)

| Peak no. | 2theta | Flex Width | d-value | Intensity | I/Io |
|---|---|---|---|---|---|
| 1 | 4.600 | 0.188 | 19.1938 | 447 | 8 |
| 2 | 8.740 | 0.165 | 13.1037 | 562 | 9 |
| 3 | 8.260 | 0.259 | 10.6954 | 433 | 7 |
| 4 | 9.100 | 0.212 | 9.7100 | 890 | 15 |
| 5 | 10.340 | 0.212 | 8.5481 | 804 | 13 |
| 6 | 11.020 | 0.188 | 8.0221 | 881 | 11 |
| 7 | 12.320 | 0.212 | 7.1784 | 1278 | 21 |
| 8 | 13.520 | 0.235 | 6.5438 | 528 | 9 |
| 9 | 13.980 | 0.235 | 6.3388 | 930 | 15 |
| 10 | 14.840 | 0.235 | 5.9646 | 1117 | 19 |
| 11 | 15.380 | 0.212 | 5.7564 | 923 | 15 |
| 12 | 16.360 | 0.212 | 5.4137 | 6268 | 100 |
| 13 | 17.080 | 0.235 | 5.1871 | 924 | 16 |
| 14 | 18.500 | 0.212 | 4.7920 | 2791 | 45 |
| 15 | 19.300 | 0.188 | 4.5952 | 1816 | 29 |
| 16 | 19.640 | 0.259 | 4.5164 | 1823 | 30 |
| 17 | 20.300 | 0.212 | 4.3710 | 1849 | 32 |
| 18 | 21.080 | 0.212 | 4.2110 | 2742 | 44 |
| 19 | 22.140 | 0.188 | 4.0117 | 3426 | 65 |
| 20 | 22.480 | 0.212 | 3.9518 | 6302 | 85 |
| 21 | 23.160 | 0.212 | 3.8373 | 3911 | 63 |
| 22 | 24.100 | 0.212 | 3.6897 | 2407 | 39 |
| 23 | 24.840 | 0.329 | 3.5814 | 945 | 16 |
| 24 | 25.380 | 0.235 | 3.5064 | 1097 | 18 |
| 25 | 27.160 | 0.235 | 3.2805 | 692 | 12 |
| 26 | 27.660 | 0.353 | 3.2224 | 902 | 15 |
| 27 | 28.240 | 0.212 | 3.1575 | 1030 | 17 |
| 28 | 29.360 | 0.259 | 3.0395 | 708 | 12 |
| 29 | 30.180 | 0.165 | 2.9588 | 707 | 12 |
| 30 | 37.180 | — | 2.4162 | 673 | 10 |

What is claimed is:

1. A solvated crystalline form of the compound of formula (I):

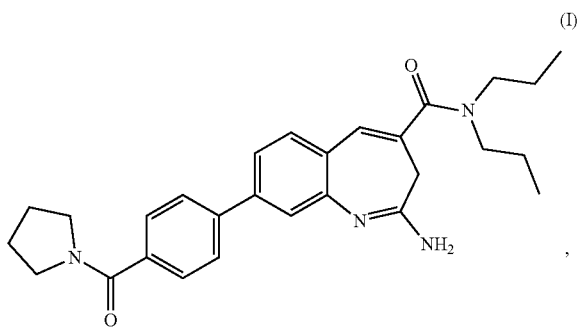 [SMILES: CCCN(CCC)C(=O)C1=Cc2ccc(-c3ccc(C(=O)N4CCCC4)cc3)cc2N=C(N)C1]

wherein said solvated crystalline form is selected from the group consisting of 1,4-dioxane solvate, dichloromethane solvate, chlorobenzene solvate, and trifluoroethanol solvate.

2. The solvated crystalline form of claim 1, wherein said crystalline form is the 1,4-dioxane solvate, characterized by an X-ray powder diffraction pattern comprising angle 2θ peaks at about 10.7±0.2, 15.2±0.2, 15.5±0.2, 17.5±0.2, 18.6±0.2, 19.7±0.2, 20.9±0.2, 21.8±0.2, 24.2±0.2, 24.7±0.2, and 26.4±0.2,
   wherein said x-ray powder diffraction spectrum is obtained using a Cu Kα radiation source (1.54 Å).

3. The solvated crystalline form of claim 2, characterized by an endothermic event with an onset temperature of about 94° C. and about 193° C. as determined by differential scanning calorimetry.

4. The solvated crystalline form of claim 1, wherein said crystalline form is the dichloromethane solvate, characterized by an X-ray powder diffraction pattern comprising angle 2θ peaks at about 15.6±0.2, 22.0±0.2, and 23.7±0.2,
   wherein said x-ray powder diffraction spectrum is obtained using a Cu Kα radiation source (1.54 Å).

5. The solvated crystalline form of claim 4, characterized by an endothermic event with an onset temperature of about 205° C. as determined by differential scanning calorimetry.

6. The solvated crystalline form of claim 1, wherein said crystalline form is the chlorobenzene solvate, characterized by an X-ray powder diffraction pattern comprising angle 2θ peaks at about 8.8±0.2, 17.7±0.2, and 21.4±0.2,
   wherein said x-ray powder diffraction spectrum is obtained using a Cu Kα radiation source (1.54 Å).

7. The solvated crystalline form of claim 1, wherein said crystalline form is the trifluoroethanol solvate, characterized by an X-ray powder diffraction pattern comprising angle 2θ peaks at about 4.6±0.2, 4.8±0.2, 15.3±0.2, 16.6±0.2, 18.1±0.2, and 22.9±0.2,
   wherein said x-ray powder diffraction spectrum is obtained using a Cu Kα radiation source (1.54 Å).

8. The solvated crystalline form of claim 7, characterized by an endothermic event with an onset temperature of about 206° C. as determined by differential scanning calorimetry.

9. The solvated crystalline form of claim 1, wherein said crystalline form is the trifluoroethanol solvate, characterized by an X-ray powder diffraction pattern comprising angle 2θ peaks at about 12.3±0.2, 14.8±0.2, 16.4±0.2, 18.5±0.2, 19.3±0.2, 19.6±0.2, 20.3±0.2, 21.1±0.2, 22.1±0.2, 22.5±0.2, 23.2±0.2, 24.1±0.2, 25.4±0.2, and 28.2±0.2,
   wherein said x-ray powder diffraction spectrum is obtained using a Cu Kα radiation source (1.54 Å).

10. The solvated crystalline form of claim 9, characterized by an endothermic event with an onset temperature of about 110° C. as determined by differential scanning calorimetry.

11. A pharmaceutical composition comprising the solvated crystalline form of claim 1 and a pharmaceutically acceptable excipient.

12. A method of treating head and neck cancer, said method comprising administering a therapeutically effective amount of the solvated crystalline form of claim 1 to a subject in need thereof, thereby treating said head and neck cancer.

13. A method of treating ovarian cancer, said method comprising administering a therapeutically effective amount of the solvated crystalline form of claim 1 to a subject in need thereof, thereby treating said ovarian cancer.

* * * * *

UNITED STATES PATENT AND TRADEMARK OFFICE
CERTIFICATE OF CORRECTION

PATENT NO. : 10,604,510 B2  
APPLICATION NO. : 16/570191  
DATED : March 31, 2020  
INVENTOR(S) : Hon-Wah Man et al.

Page 1 of 1

It is certified that error appears in the above-identified patent and that said Letters Patent is hereby corrected as shown below:

On the Title Page

Item (54):
"SOLID FORMS COMPRISING (1E, 4E)-2-AMINO-N,N-DIPROPYL-8-(4-(PYRROLIDINE-1-CARBONYL)PHENYL)-3H-BENZO[B]AZEPINE-4-CARBOXAMI, COMPOSITIONS THEREOF, AND USES THEREOF"

Should read:
--SOLID FORMS COMPRISING (1E, 4E)-2-AMINO-N,N-DIPROPYL-8-(4-(PYRROLIDINE-1-CARBONYL)PHENYL)-3H-BENZO[B]AZEPINE-4-CARBOXAMIDE, COMPOSITIONS THEREOF, AND USES THEREOF--

Signed and Sealed this  
Twenty-third Day of June, 2020

Andrei Iancu  
*Director of the United States Patent and Trademark Office*